(12) United States Patent
Lu et al.

(10) Patent No.: US 10,301,328 B2
(45) Date of Patent: May 28, 2019

(54) ORGANOBORON COMPOUNDS AND METHODS OF MAKING SAME

(71) Applicants: Jiasheng Lu, Kingston (CA); Suning Wang, Kingston (CA)

(72) Inventors: Jiasheng Lu, Kingston (CA); Suning Wang, Kingston (CA); Soo-Byung Ko, Kingston (CA); Sean Michael McDonald, Kingston (CA); Dengtao Yang, Kingston (CA)

(73) Assignee: Jiasheng Lu, Shanghai (CN)

( * ) Notice: Subject to any disclaimer, the term of this patent is extended or adjusted under 35 U.S.C. 154(b) by 472 days.

(21) Appl. No.: 14/779,601

(22) PCT Filed: Mar. 25, 2014

(86) PCT No.: PCT/CA2014/000297
§ 371 (c)(1),
(2) Date: Sep. 24, 2015

(87) PCT Pub. No.: WO2014/153648
PCT Pub. Date: Oct. 2, 2014

(65) Prior Publication Data
US 2016/0046652 A1    Feb. 18, 2016

Related U.S. Application Data

(60) Provisional application No. 61/804,952, filed on Mar. 25, 2013.

(51) Int. Cl.
*H01L 51/50* (2006.01)
*C07F 5/02* (2006.01)
(Continued)

(52) U.S. Cl.
CPC ............... *C07F 5/02* (2013.01); *C07F 5/022* (2013.01); *C07F 15/0086* (2013.01);
(Continued)

(58) Field of Classification Search
CPC .. H01L 51/0072; H01L 51/008; Y02P 70/521; C09K 11/025
See application file for complete search history.

(56) References Cited

PUBLICATIONS

International Search Report and Written Opinion for International Application No. PCT/CA2014/000297 filed on Mar. 25, 2014.
(Continued)

*Primary Examiner* — Gregory D Clark
(74) *Attorney, Agent, or Firm* — BCF LLP

(57) ABSTRACT

The invention provides organoboron precursors and facile photoirradiation and/or heating methods of making corresponding elimination products. Some elimination products are polycyclic aromatic molecules wherein a number of aromatic C—C moieties have been replaced by a B—N moiety to form azaborine compounds with interesting properties such as electronic, photophysical, luminescent, as well as chemical properties. Examples of polymer films that were doped with such compounds are shown wherein irradiated portions of the polymer film luminesce. The invention further provides methods of producing photoluminescence and electroluminescence, and uses of the compounds of the invention in luminescent probes, sensors, electroluminescent devices, hydrogen storage materials, optoelectronic materials, and bioactive molecules.

18 Claims, 17 Drawing Sheets

(51) Int. Cl.
| | |
|---|---|
| *C09K 11/06* | (2006.01) |
| *H01L 51/00* | (2006.01) |
| *G03G 5/06* | (2006.01) |
| *C07F 15/00* | (2006.01) |
| *C09K 11/02* | (2006.01) |
| *G03F 7/20* | (2006.01) |

(52) U.S. Cl.
CPC ............ *C09K 11/025* (2013.01); *C09K 11/06* (2013.01); *G03F 7/20* (2013.01); *G03G 5/0653* (2013.01); *G03G 5/0659* (2013.01); *H01L 51/008* (2013.01); *H01L 51/0071* (2013.01); *H01L 51/0072* (2013.01); *H01L 51/0087* (2013.01); *C09K 2211/104* (2013.01); *C09K 2211/107* (2013.01); *C09K 2211/1033* (2013.01); *C09K 2211/1037* (2013.01); *C09K 2211/1044* (2013.01); *C09K 2211/1048* (2013.01); *C09K 2211/1055* (2013.01); *C09K 2211/1085* (2013.01); *C09K 2211/1096* (2013.01); *C09K 2211/185* (2013.01); *H01L 51/5012* (2013.01); *H01L 51/5016* (2013.01); *Y02E 10/549* (2013.01); *Y02P 70/521* (2015.11)

(56) References Cited

PUBLICATIONS

International Preliminary Report for International Application No. PCT/CA2014/000297 filed on Mar. 25, 2014.
Lu, J.-S., et al., "Formation of azaborines by photoelimination of B,N-heterocyclic compounds", Angew. Chem. Int. Ed. Engl., Apr. 22, 2013, 52(13), 4544-4548.
Lu, J.-S., "N N-and N C chelate four-coordinate organoboron compounds: Synthesis, properties and application", Queen's University, Kingston, Canada Ph.D. Thesis, issued Apr. 24, 2013, Chapter 4, 165-253.
Biswas, S., "Boron-nitrogen derivatives of organic reactive intermediates", Universitat Tubingen, Germany, Ph.D. Thesis, Jan. 30, 2012.
Campbell, P.G. et al., "Recent advances in azaborine chemistry", Angew. Chem. Int. Ed., Engl., 2012, 51(25), 6074-6092.
Hudson, Z.M., et al., "Efficient and High Yield One-Pot Synthesis of Cyclometalated Platinum (II) B-Diketonates at Ambient Temperature", Organic Letters, vol. 14, No. 7, 2012, 1700-1703.
Rao, Y-L., et al., "Reversible Intramolecular C—C Bond Formation/ Breaking and Color Switching Mediated by a N,C-Chelate in (2-ph-py)BMes2 and (5-BMes2-2-ph-py)BMes2", JACS, vol. 130, 2008, 12896-12900.
Hachiya, H. et al., "Nickel-Cateized Direct Acylation of Azoles with Aryl Bromides" Organic Letters, vol. 11, No. 8, 2009, 1737-1740.
Pan, J., et al., "1,2-Azaboratabenzene: A Heterocyclic Ligand with an Adjustable Basicity at Nitrogen", Organometallics, vol. 23,2004, 5626-5629.
Sambursky, S., et al., "On the Fluorescence and Absorption Spectra of Anthracene and Phenanthrene in Solutions", Trans. Faraday Soc., 1940, 427-432.
Bosdet, M.J.D., et al., "10a-Aza-10b-borapyrenes: Heterocyclic Analogues of Pyrene with Internalized BN Moieties", Angew. Chem. Int. Ed., vol. 46, 2007, 4940-4943.
Taniguchi, T., et al., "'A Study of 1,2-Dihydro-1,2-azaborine in a Conjugated System", Organometallics, vol. 29, 2010, 5732-5735.
Bosdet, M.J.D., et al., "Blue Fluorescent 4a-Aza-4b-boraphenanthrenes", Organic Letters, vol. 9, No. 7, 2007, 1395-1398.
Dewar, M.J.S., et al., "New Heteroaromatic Compounds, XVI Compounds with Heteroatoms at Bridgeheads", J. Am. Chem. Soc., vol. 84, 1962, 4884-4887.
Lepeltier, M., et al., "New azaborine-thiopene heteroacenes", Chem. Commun., vol. 46, 2010, 7007-7009.
Dewar, M.J.S., et al., "New Heteroaromatic Compounds. Part 1. 9-Aza-10-bora-phenanthrene", J. Chem. Soc. 1958, 3073-3076.

ORGANOBORON COMPOUNDS AND METHODS OF MAKING SAME

CROSS-REFERENCE TO RELATED APPLICATIONS

This application claims the benefit of the filing date of U.S. Provisional Patent Application No. 61/804,952 filed on Mar. 25, 2013, the contents of which are incorporated herein by reference in their entirety.

FIELD OF THE INVENTION

The invention relates to methods of synthesizing organoboron compounds, and providing useful materials for a variety of optoelectronic devices.

BACKGROUND OF THE INVENTION

Organoboron compounds have broad applications in organic synthesis (*Boronic acids*, D. G. Hall, ed. Wiley-VCH, Weinheim, 2005), catalysis (P. A. Chase, et al., *Angew. Chem. Int. Ed.* 2007, 46, 8050; A. Staubitz et al., *Chem. Rev.* 2010, 110, 4079; W. E. Piers et al., *Inorg. Chem.* 2011, 50, 12252), optoelectronic devices (C. D. Entwistle et al., *Angew. Chem. Int. Ed.* 2002, 41, 2927; C. D. Entwistle et al., *Chem. Mater.* 2004, 16, 4574; Y. Shirota et al., *Chem. Rev.* 2007, 107, 953; F. Jäkle, *Chem. Rev.* 2010, 110, 3985; P. Chen, et al., *Angew. Chem. Int. Ed.* 2012, 51, 7994; C. Dou, et al., *Angew. Chem. Int. Ed.* 2012, 51, 12206; S. Saito, et al., *J. Am. Chem. Soc.* 2012, 134, 9130; Z. M. Hudson, et al., *Dalton Trans.* 2011, 40, 7805), sensors (C. R. Wade, et al., *Chem. Rev.* 2010, 110, 3958), and probes (G. Zhang, et al., *Nature Mater.* 2009, 8, 747; F. R. Kersey, et al., *ACS Nano* 2010, 4, 4989). Among π-conjugated organoboron compounds, azaborines (aromatic molecules wherein a C—C moiety has been replaced by a B—N moiety) have attracted much research interest. Such replacement of a C—C unit in an aromatic molecule with an isoelectronic B—N unit has been shown to impart interesting properties that are distinct from those of the C—C aromatic analogues. Such properties may include electronic, photophysical, luminescent, as well as chemical properties.

Examples of polycyclic π-conjugated azaborine molecules and derivatives remain rare, compared to the vast numbers of carbocyclic aromatic compounds and heterocyclic aromatic compounds. Known syntheses of azaborine compounds are challenging, and frequently involve multi-step reactions and/or use of transition metal catalysts. Development of efficient and simple synthetic methods for B—N substituted aromatic compounds is desirable to advance the chemistry and applications of this class of compounds. Photoelimination reactions are known for many organic compounds such as azo, azide and ketone compounds (W. H. Saunders, et al., *Mechanisms of Elimination Reactions*, John Wiley & Sons, New York, 1973; A. Gilbert, et al., *Photochemistry*, 1995, 26, 326). They are, however, rare for organoboron compounds (A. Pelter, et al., *Tetrahedron*, 2000, 56, 7339).

SUMMARY OF THE INVENTION

An aspect of the invention provides a method of making organoboron compounds, comprising photoirradiating and/or heating a reactant, and obtaining an elimination product, wherein the reactant comprises: (i) a boron atom that is bonded at least to a first moiety and a second moiety, the first moiety being a terminal moiety, and the second moiety being a Lewis base; and (ii) a carbon atom that is proximal to the boron and that is bonded to at least one hydrogen atom, wherein the elimination product differs from the reactant such that the elimination product: (a) has a bond between the boron and the carbon, which may be a single bond or an additional bond between the boron and the carbon; and (b) does not include the first (i.e., terminal) moiety.

In an embodiment of the above aspect, the carbon atom of the elimination product is bonded to at least one less hydrogen than the carbon of the reactant. In another embodiment of this aspect, the elimination product's boron atom can undergo one or more subsequent elimination reaction(s) involving the same carbon atom or a different carbon atom.

In an embodiment of this aspect, the reactant is photoirradiated or heated in solid state, in solution, or in a polymer matrix. In an embodiment of this aspect, the terminal moiety is a hydrogen atom, substituted or unsubstituted aliphatic, or substituted or unsubstituted aryl. In another embodiment of this aspect, the terminal moiety is methyl, unsubstituted phenyl, substituted phenyl, or mesityl. In another embodiment of this aspect, the invention provides a second moiety which is an aryl (which includes heteroaryl) moiety, an N-heterocyclic carbene, or comprises a heteroatom. In an embodiment of this aspect, the aryl moiety is substituted or unsubstituted pyridyl. In some embodiments, the N of the pyridyl ring is bonded to the boron.

In certain embodiments of this aspect, the invention provides a method comprising a reaction:

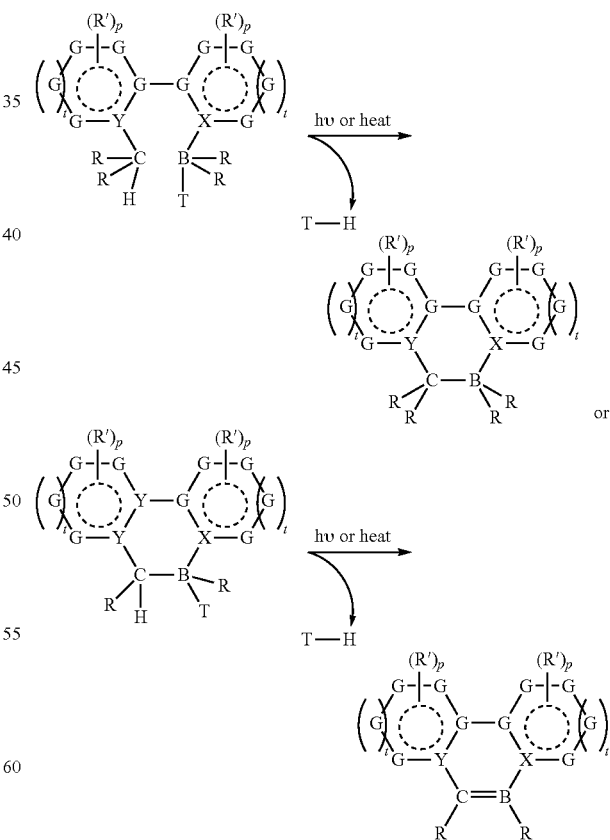

wherein G is independently carbon or a heteroatom (e.g., N, S, O, P), X and Y are independently carbon or nitrogen, T is a terminal moiety, R is hydrogen, a linear, branched or cyclic aliphatic moiety, or an aryl (which includes heteroaryl) moiety, and may be further substituted, R' is hydrogen, a linear, branched or cyclic aliphatic moiety, or an aryl (which includes heteroaryl) moiety, and may be further substituted, and is optionally a fused ring(s), t is independently 0 or 1, p is independently 0 to 10, and a dotted circle represents optional aromaticity, with the proviso that at least one moiety bonded to B, excluding the terminal moiety, is a Lewis base.

In an embodiment of this aspect, the ring comprising X is an N-heterocyclic carbene. In another embodiment of this aspect, the ring comprising X is pyridyl and wherein the N of the pyridyl ring is bonded to B. In another embodiment of this aspect, Y is carbon, X is nitrogen, and at least one G of the ring comprising X is a heteroatom. In an embodiment of this aspect, R' is further substituted by a transition metal or a main group metal. The metal may be chelated. In another embodiment, the transition metal is platinum or zinc. In another embodiment of this aspect, the main group metal is aluminum or boron. In another embodiment, the polymer is poly(methyl methacrylate) or poly(N-vinylcarbazole). In another embodiment of this aspect, the elimination product is photoluminescent or electroluminescent. In another embodiment of this aspect, the elimination product is an electron transport material. In another embodiment of this aspect, the elimination product is a hydrogen storage material. In another embodiment of this aspect, the elimination product is a solar cell material. In another embodiment of this aspect, R' is a fused aromatic ring that bridges the ring comprising X and the ring comprising Y. In another embodiment of this aspect, the elimination product is photoluminescent and/or is an electron transport material. In another embodiment of this aspect, the reactant is: BN-1, BN-2, BN-3, BN-4, BN-7, (BN2)-1, (BN2)-2, BC-1, BC-2, BC-3, BC-4, BN-bpy1, or BN-Bpy-Pt1. In another embodiment of this aspect, the elimination product is a diboron molecule. In another embodiment of this aspect, the elimination product is BN-5 or BN-6. In another embodiment of this aspect, the elimination product is BN-1a, BN-2a, BN-3a, BN-4a, (BN2)-1a, SM1-aza, DT1-aza, or BN-5b. In another embodiment of this aspect, a final product is a triboron compound or a conjugated polycyclic compound comprising B—N moieties. In another embodiment of this aspect, the product is a conjugated aromatic triboron compound or a 2D conjugated polyaromatic system comprising boron. In another embodiment of this aspect, the triboron compound is BN-5b, (BN)2-2a, BN-5c, BN-6c, BC-1b, BN-7b, BN-bpy1a, BN-bpy-Pt1a, or BC-1.

In another embodiment of this aspect, the elimination product has bound to the boron: a carbene ring, a mesityl, a pyridyl ring, a pyridyl that is part of a fused ring system, an unsaturated five-membered heterocycle comprising both S and N ring atoms, or an unsaturated five-membered heterocycle comprising both S and N ring atoms that is part of a fused ring system.

In another embodiment of this aspect, the photoirradiation is UV-irradiation. In another embodiment of the above method wherein R' comprises a transition metal, main group metal or rare earth metal, wherein the photoirradiation is exposing to visible light. In another embodiment of this aspect, a reactant is doped into polymeric film. In another embodiment of this aspect, the polymeric film's polymer comprises PMMA or PVK. Yet another aspect is a patterned fluorescent polymer film made by aspects and/or embodiments of the above methods. In an embodiment of this aspect the invention provides a patterned fluorescent polymer film, wherein the film is used in an optoelectronic device.

An aspect of the invention provides an article that comprises an elimination product made by a method of any of the above aspects, wherein the elimination product is doped in a polymer film. The article may be a manufacture, a machine, or a component thereof. In embodiments of the above aspects regarding a doped film, the film is fluorescent, phosphorescent, and/or electroluminescent. In certain embodiments, the film is patterned with luminescent and non-luminescent areas. In another embodiment of this aspect, photoirradiation is used to create patterns in solid state or in a polymer matrix. In another embodiment of this aspect, the elimination product is used in an optoelectronic device. In another embodiment of this aspect, the elimination product is a polycyclic π-conjugated compound. In yet another aspect, the invention provides a method of producing electroluminescence, comprising the steps of: providing the electroluminescent elimination product of any of the above aspects and/or embodiments and applying a voltage across the compound so that the compound electroluminesces.

In an aspect the invention provides a method of harvesting photons, comprising the steps of providing the elimination product of any of the above aspects and/or embodiments, and providing light such that photons strike the elimination product and charge separation occurs in the elimination product.

In an embodiment of this aspect, the separated charges recombine and photons are released. In an embodiment of this aspect, the separated charges migrate to respective electrodes to produce a potential difference. In another aspect the invention provides a method of separating charges, comprising the steps of: providing the elimination product of any of the above aspects and/or embodiments, and providing light such that photons strike the elimination product and charge separation occurs in the elimination product. In an embodiment of this aspect, the separated charges recombine and photons are released. In another embodiment of this aspect the separated charges migrate to respective electrodes to produce a potential difference. In an embodiment of this aspect the Lewis base comprises a pyridyl, a pyrimidinyl, a benzothiazolyl, or an imidazolyl. In an embodiment of this aspect, the reactant comprises a chelated metal.

In an embodiment of this aspect, the chelated metal is a transition metal, rare earth metal, or main group metal. In an embodiment of this aspect, the elimination product is BN-bpy-Pt1, or BN-bpy-Pt1a. In an embodiment of this aspect, the reactant's boron is bound to three hydrogens and undergoes eliminations so that the final elimination product is a triboron compound. In an embodiment of this aspect, the elimination product is a polycyclic compound. In an embodiment of this aspect, the elimination product is an aromatic polycyclic compound. In an embodiment of this aspect, the elimination product is a graphene wherein at least one C—C moiety has been replaced by a B—N moiety. Another aspect of the invention provides a method of making a patterned fluorescent film, comprising casting a polymer doped with the reactant of any of the above aspects and/or embodiments to form a polymeric film, positioning a patterned mask having solid areas and open areas between the film and a source of light, and exposing the mask-position film to the light, and obtaining a patterned film with non-luminescent areas corresponding to the solid areas of the mask, and luminescent areas corresponding to the open areas of the mask that allowed the light to strike the film. In an embodiment of this aspect, the light is UV light. In another aspect the invention provides a photocopier employing embodiments and/or aspects of the above method of harvesting photons or embodiments and/or aspects of the above method of separating charges.

In yet another aspect the invention provides a photovoltaic device employing embodiments and/or aspects of the above method of harvesting photons or embodiments and/or aspects of the above method of separating charges.

In an aspect the invention provides a photoreceptor employing embodiments and/or aspects of the above method of harvesting photons or embodiments and/or aspects of the above method of separating charges.

In another aspect the invention provides, the invention provides a solar cell employing embodiments and/or aspects of the above method of harvesting photons or embodiments and/or aspects of the above method of separating charges.

Another aspect provides a semiconductor employing embodiments and/or aspects of the above method of harvesting photons or embodiments and/or aspects of the above method of separating charges.

In an aspect, the invention provides an electroluminescent device for use with an applied voltage, comprising a first electrode, an emitter which is an electroluminescent elimination product of any of the above aspects and/or embodiments optionally in a host layer, and a second, transparent electrode, wherein voltage is applied to the two electrodes to produce an electric field across the emitter so that the emitter electroluminesces.

In another aspect, the invention provides an electroluminescent device for use with an applied voltage, comprising a first electrode, a second, transparent electrode, an electron transport layer adjacent the first electrode, a hole transport layer adjacent the second electrode, and an emitter which is an electroluminescent elimination product of any of the above aspects and/or embodiments optionally in a host layer, interposed between the electron transport layer and the hole transport layer, wherein voltage is applied to the two electrodes to produce an electric field across the emitter so that the emitter electroluminesces.

In another aspect, the invention provides a light emitting device comprising an anode, a cathode, and an emissive layer disposed between the anode and the cathode, wherein the emissive layer comprises the elimination product of any of the above aspects and/or embodiments. In an embodiment of this aspect, the emissive layer further comprises a host. Another aspect provides a consumer product comprising the above aspect and embodiment regarding a light emitting device. In yet another aspect, an optoelectronic device is provided that comprises the elimination product made by any of the above aspects or embodiments thereof.

An aspect of the invention provides a compound made by the method of any one of the above methods of making aspects or embodiments.

In another aspect the invention provides, the invention provides a compound of general formula:

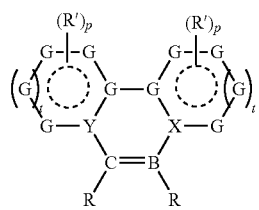

wherein G is independently carbon or a heteroatom (e.g., N, S, O, P), X and Y are independently carbon or nitrogen, R is an aliphatic or aryl (which includes heteroaryl) moiety that may be further substituted, R' is an aliphatic or aryl (which includes heteroaryl) moiety that may be further substituted and is optionally a fused ring(s), t is independently 0 or 1, p is independently 0 to 10, and a dotted circle represents optional aromaticity. In an embodiment of this aspect, the invention provides the compound of the previous aspect, wherein for the ring comprising X, t is zero and at least one ring atom is a heteroatom, so that ring is a five-membered heterocycle. In another embodiment of the previous aspect and its embodiments, X is nitrogen and Y is carbon. In an embodiment, the ring comprising Y is substituted phenyl. In another embodiment of this aspect, wherein the R substituent on B is mesityl. In another embodiment of this aspect, the compound is BN-1a, BN-2a, BN-3a, BN-4a, (BN2)-1a, BN-5b, SM1-aza, or DT1-aza. In an embodiment of this aspect, the compound is a hydrogen storage material, optoelectronic material, sensor, bioactive molecule, and/or electroluminescent material.

In another aspect the invention provides, the invention provides a compound which comprises a structure of general formula:

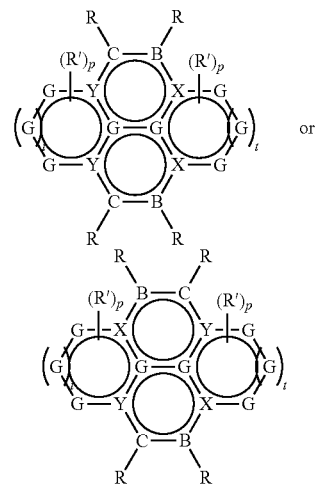

wherein G, R, R', p, t, X, and Y are as defined previously.

In another aspect the invention provides, the invention provides a compound which comprises a structure of general formula:

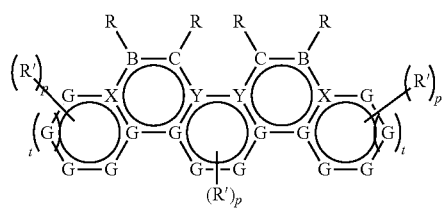

wherein G, R, R', t, p, X, and Y are as defined previously, and wherein rings may be substituted or unsubstituted.

In yet another aspect, the invention provides a compound which comprises a structure of general formula:

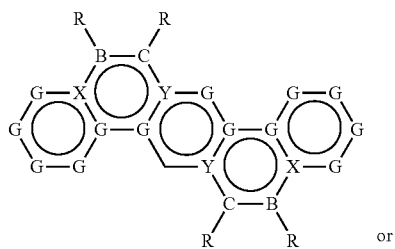

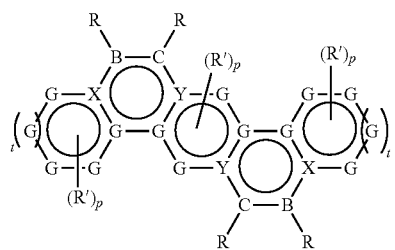

wherein G, R, R', p, t, X, and Y are as defined previously, and wherein rings may be substituted or unsubstituted.

In another aspect the invention provides, the invention provides a compound which comprises a structure of general formula:

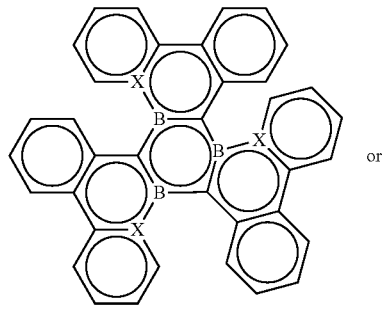

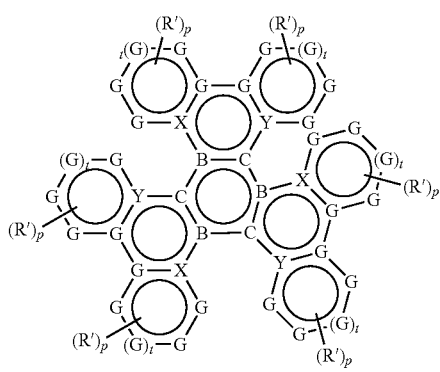

wherein G, R, R', t, p, X, and Y are as defined previously, and wherein rings may be substituted or unsubstituted.

In an aspect the invention provides a compound which comprises a structure of general formula:

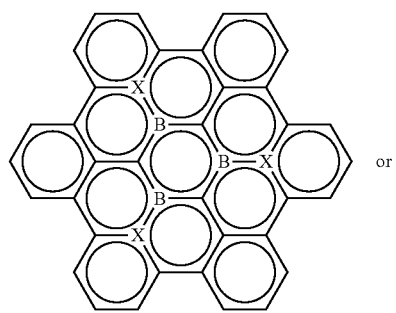

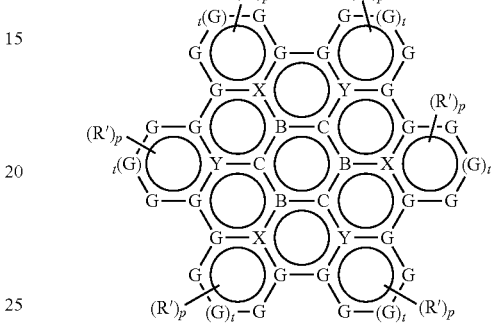

wherein G, R, R', t, p, X, and Y are as defined herein, and wherein rings may be substituted or unsubstituted. In other embodiments of the invention relating to compounds, a compound is provided which is: (BN)2-2, BN-5b, (BN)2-2a, BN-5c, BN-6c, BC-1b, BN-7b, BN-bpy1a, BN-bpy-Pt1a, BC-1, (BN)2-2b, BN-5, BN-6, BN-1a, BN-2a, BN-3a, BN-4a, (BN2)-1a, BN-5b, BN-5b, (BN)2-2a, BN-5c, BN-6c, BC-1b, BN-7b, BN-bpy1a, BN-bpy-Pt1a, BC-1, SM1-aza, or DT1-aza.

In yet another aspect, the invention provides a method of making organoboron compounds, comprising photoirradiating a reactant, and obtaining an elimination product, wherein the reactant comprises (i) a boron atom that is bonded at least to a first ligand and a second ligand, the first ligand being a terminal moiety, and the second ligand being a Lewis base, and (ii) a carbon atom that is proximal to the boron and that is bonded to at least one hydrogen atom, wherein the elimination product differs from the reactant in that in the elimination product (a) there is a bond between the boron and the carbon, which may be a new linkage or an additional bond between previously linked atoms, (b) the boron atom is no longer bonded to the terminal ligand, and (c) the carbon atom is no longer bonded to the hydrogen, and optionally, the elimination product's boron atom can undergo one or more subsequent elimination reaction(s) involving the same carbon atom or a different carbon atom.

BRIEF DESCRIPTION OF THE DRAWINGS

For a better understanding of the present invention and to show more clearly how it may be carried into effect, reference will now be made by way of example to the accompanying drawings, which illustrate aspects and features according to preferred embodiments of the present invention, and in which:

FIG. 4A shows the crystal structure of compound BN-3a;

DETAILED DESCRIPTION OF THE INVENTION

Definitions

Figure 1A:
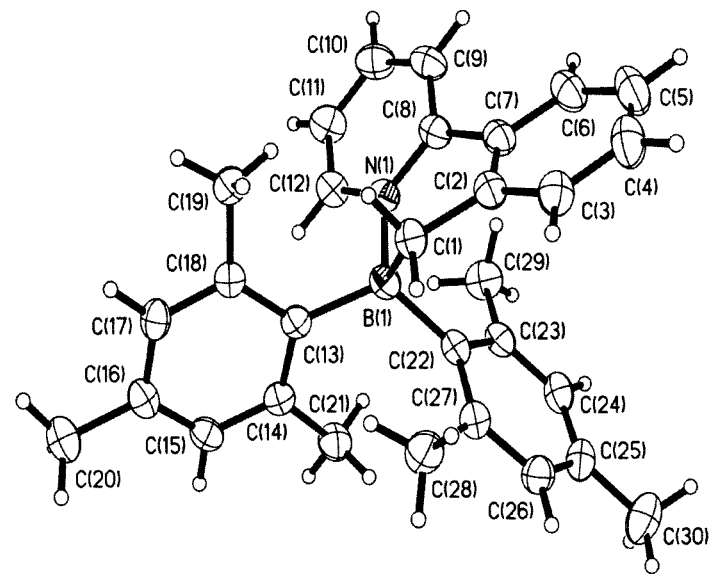
FIG. 1A shows the crystal structure of BN-1.

As used herein, the term "azaborine" refers to a compound comprising at least one boron atom and at least one nitrogen atom. Although not meant to be limiting, "azaborine" may describe a compound that comprises a B—N moiety.

As used herein, the term "TfOH" means trifluoromethanesulfonic acid, which is also known as triflic acid or $CF_3SO_3H$. The term "TsOH" means p-toluenesulfonic acid. The term "TFA" means trifluoroacetic acid. The term "PA" means picolinic acid.

As used herein, the terms "N^C" chelate, "P^C" chelate and "C^C" chelate indicate chelation ligands wherein the atoms indicated are those that are bonded to the central atom. As used herein the term "aliphatic" includes alkanyl, alkenyl and alkynyl moieties. An aliphatic group may be substituted or unsubstituted. It may be straight chain, branched chain or cyclic.

As used herein the term "Mes" means mesityl, which is also known as 2,4,6-trimethylphenyl.

As used herein the term "aryl" includes aromatic carbocycles and aromatic heterocycles, and aryl moieties may be substituted or unsubstituted.

As used herein, the term "unsubstituted" refers to any open valence of an atom being occupied by hydrogen. Also, if an occupant of an open valence position on an atom is not specified then it is hydrogen.

As used herein "substituted" refers to the structure having one or more substituents.

As used herein "heteroatom" means a non-carbon, non-hydrogen atom. In some cases, a heteroatom may have a lone pair of electrons available to form dative or coordinate bonds (e.g., N, O, S, P).

As used herein, the term "HSQC" refers to Heteronuclear Single Quantum Coherence, which is a Nuclear Magnetic Resonance (NMR) method to determine chemical shifts that are difficult to determine by typical NMR.

As used herein, the term "dative bond" refers to a coordination bond formed when one molecular species serves as a donor and the other as an acceptor of an electron pair to be shared.

As used herein, the term "Lewis base" refers to a molecular entity able to provide a pair of electrons (IUPAC Gold Book).

As used herein, the term "isoelectronic" means two or more molecular entities that have the same number of valence electrons and the same structure, i.e. number and connectivity of atoms, but differ in some of the elements involved (IUPAC Gold Book).

As used herein, the term "ligand" refers to a chemical species or moiety that is capable of bonding an atom of interest (e.g., boron).

As used herein, the term "moiety" refers to an indefinite portion (i.e., a segment or part of a whole) of a molecule.

As used herein, the term "terminal ligand" describes an atom or group of atoms (charged or uncharged) that is non-bridging, i.e., does not connect to another part of the molecule, but rather ends. In this context, in specified reactions described herein, the terminal ligand of a reactant leaves and is absent from the consequent product. Also as used herein, the term "terminal moiety" describes an atom or group of atoms (charged or uncharged) that is non-bridging, i.e., does not connect to another part of the molecule, but rather ends. In this context, in specified reactions described herein, the terminal moiety of a reactant leaves and is absent from the consequent product.

As used herein, the term "proximal" when used in relation to chemical reactivity, means that chemical moieties that are proximal are close enough to one another to influence each other's reactivity. Although not strictly required, in some instances, proximal groups are three bonds away from one another. In other instances, proximal groups are bonded to one another. In certain embodiments, proximal groups are several bonds from one another (e.g., 5 bonds), but they can be positioned close enough in space to influence each other's reactivity.

As used herein, the term "main group metal" refers to elements in groups whose lightest members are helium, lithium, beryllium, boron, carbon, nitrogen, oxygen, and fluorine as arranged in columns of the periodic table of the elements. Main group elements include elements (except hydrogen) in groups 1 and 2 (s-block), and groups 13 to 18 (p-block).

As used herein, the term "rare earth metal" refers to a set of seventeen chemical elements in the periodic table, specifically, fifteen lanthanides plus scandium and yttrium.

As used herein, the term "luminescence" refers to emission of light by a substance not resulting from heat; it is thus a form of cold body radiation. "Electroluminescence" refers to luminescence as a result of an electric current passing through a substance. "Photoluminescence" refers to luminescence as a result of absorption of photons. "Fluorescence" refers to photoluminescence as a result of singlet-singlet electronic relaxation (typical lifetime: nanoseconds). "Phosphorescence" refers to photoluminescence as a result of triplet-singlet electronic relaxation (typical lifetime: milliseconds to hours).

As used herein, the term "optoelectronics" refers to study and application of electronic devices that source, detect and control light. Optoelectronic devices are electrical-to-optical or optical-to-electrical transducers, or instruments that use such devices in their operation.

Embodiments

A new and facile photoelimination synthetic method has been discovered. This method provides a synthesis for forming one or more bonds between carbon and boron. In certain embodiments, a reactant compound that is suitable for this synthetic method comprises a boron that is bonded to a terminal ligand and that is also bonded to a Lewis base (i.e., a moiety having a lone pair of electrons) through a dative bond. Such suitable compound also includes a carbon located proximal to the boron, wherein the carbon is bonded to at least one hydrogen atom. Upon irradiation with light, the reactant undergoes an elimination reaction. After this elimination reaction, the hydrogen and the terminal ligand are no longer bonded to the carbon and boron, respectively, and may be bonded to one another. Also after this elimination reaction, the product has a newly-formed bond between the carbon and the boron. In some embodiments, the newly-formed bond is a single bond between the carbon and the boron. In other embodiments, the newly-formed bond is an additional bond between these two atoms that were previously bonded by a lesser number of bonds (e.g., a double bond where previously there had been a single bond).

In some embodiments, the boron is bonded to a carbon atom or nitrogen atom that is a ring atom of an aromatic ring. In some embodiments, the boron is a substituent of a fused aromatic ring system. In certain embodiments, the boron is a substituent of a carbocycle that may be aromatic or non-aromatic. In certain embodiments, the boron is a substituent of a heterocycle that may be aromatic or non-aromatic. In certain embodiments, the boron is a substituent of a heterocycle and is bonded to the heterocycle through at least one of its heteroatom(s). In other embodiments, the boron is a substituent of a heterocycle and is bonded to the heterocycle through a carbon ring atom.

A schematic is provided below as a simplified example of this new synthetic method.

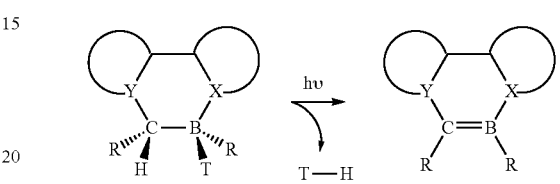

wherein X and Y are independently carbon or nitrogen;
T is a terminal ligand (e.g., H, aliphatic, aryl, $CH_3$, mesityl);
R is a aliphatic or aryl moiety that may be further substituted;
a circular moiety represents an aromatic, non-aromatic, saturated, or unsaturated cyclic moiety.

Acceptable substituents include any chemical moiety that does not interfere with the desired reaction and may include, for example: a non-aromatic carbocycle or heterocycle, an aryl group (which includes a heteroaryl) that is attached as a fused ring or as a substituent, a hydroxy group, alkoxo, nitro, amino, halo, $BR_2$, $B(aryl)_2$, aryl-$B(aryl)_2$, O, $NR_2$, OR, a nitrile group, —$C(halo)_3$ which includes —$CF_3$, and R, where R is a substituted or unsubstituted aliphatic group having 1-24 carbon atoms which may be straight, branched or cyclic (e.g., adamantyl). A substituent may be further substituted.

In addition, through this new synthetic method, new organoboron (aromatic and non-aromatic) compounds have been prepared and characterized. In certain embodiments, such compounds have a B—N moiety as a replacement for a C—C unit in an aromatic molecule. This is possible because a B—N moiety is isoelectronic to C—C (see Campbell, P. G. et al., *Angew. Chem. Int. Ed.* 2012, 51, 6074-6092). Such replacements lead to new compounds with interesting new properties. Hence, such compounds may be useful in a variety of fields such as: hydrogen storage materials (P. G. Campbell, et al., *J. Am. Chem. Soc.* 2010, 132, 18048), optoelectronic materials (T. Agou, et al., *Org. Lett.* 2006, 8, 2241; R. Kwong, G. Kottas, International Patent, WO 2011/143563 A2), sensors (T. Agou, et al., *Chem. Commun.* 2009, 1894; M. Lepeltier, et al., *Chem. Commun.* 2010, 46, 7007), and bioactive molecules (L. Liu, et al., *Angew. Chem. Int. Ed.* 2009, 48, 6817). Examples of organoboron compounds that display photochemical reactivity are known previously (W. H. Saunders, et al., *Mechanisms of Elimination Reactions*, John Wiley & Sons, New York, 1973; A. Gilbert, et al., in *Photochemistry*, 1995, 26, 326; A. Pelter, et al., *Tetrahedron*, 2000, 56, 7339; Y. L. Rao, et al., *Coord. Chem. Rev.* 2012, 256, 759; R. L. Rao, et al., *J. Am. Chem. Soc.* 2008, 130, 12898; K. Ansorg, et al. *Angew. Chem. Int. Ed.* 2011, 50, 2833; J. D. Wilkey, et al., *J. Am. Chem. Soc.* 1988, 110, 7569).

However, the present photoelimination reaction is unusual. In certain embodiments, a C—H bond is cleaved and a B—C bond is formed. Furthermore, the present photoelimination method provides a general method to produce N-heterocyclic compounds, where ring heteroatoms comprise B and N, optionally bonded to each other. Such compounds may be, for example, fused ring systems. (One might imagine a graphene in which one or more C—C moiety is replaced by a corresponding one or more B—N moiety). The photoelimination reaction product may comprise, for example, a pyridyl, pyrimidinyl, benzothiazolyl, or imidazolyl moiety. In addition, the present photoelimination reaction also applies to N-heterocyclic carbenes (NHCs) functioning as the Lewis base that forms a dative bond with boron (see Scheme 4), enabling generation of boron-substituted aromatic compounds. Furthermore, the present photoelimination method can be applied in the synthesis of polycyclic aromatic compounds such as B—N replaced graphenes and related extended π-conjugated materials, which are an important class of materials for organic electronics and organic optoelectronic devices (Geim, A. K. et al. Nature Materials, 2007, 6, 183).

Importantly, it has been shown that this photoelimination reaction may also occur readily in a polymer matrix or in solid state. As described herein, initial studies have shown that precursor compounds (i.e., reactants from which there will be elimination) BN-1, BN-2, BN-3 and BN-4 can undergo quantitative photoelimination in a polymer film (e.g. PMMA) in the same manner as seen in solution. Such polymer films studies generated luminescent aromatic azaborine compounds (see UV-Vis spectra and fluorescence spectra in FIGS. 6A to 6D). Preliminary tests also confirmed that the photoelimination can occur in neat film of these precursors. This property enabled facile generation of polycylic aromatic compounds using the photoelimination method described herein. Such macromolecular elimination products are emissive (e.g., highly emissive) and/or conductive (e.g., highly conductive) in the solid state (e.g., on a surface of an electrode layer such as, for example, Indium-Tin-Oxide) or in a conducting polymer matrix such as PVK. Thus, by using light, and highly soluble and readily sublimable precursor molecules, it was possible to pattern optoelectronic devices (see FIG. 6E, and inset photographs in FIGS. 6A-D. Patterning may enhance the performance of optoelectronic devices such as such as OLEDs and photovoltaic devices. An advantage of certain compounds of this invention is their good solubility in hydrophobic solvents. Insolubility or poor solubility of polycarbocyclic aromatic compounds such as graphenes has limited their incorporation for electrode surfaces and/or active layers of optoelectronic devices. For this reason, polycyclic aromatic compounds that have a number of B—N moieties in place of C—C aromatic ring atoms may have broad uses in the field of optoelectronic devices.

Precursors suitable as reactants for this photoelimination or thermoelimination reaction include compounds that comprise a structure of one or more formulae set forth below. Their corresponding elimination products are provided as the products of the reactions set forth below.

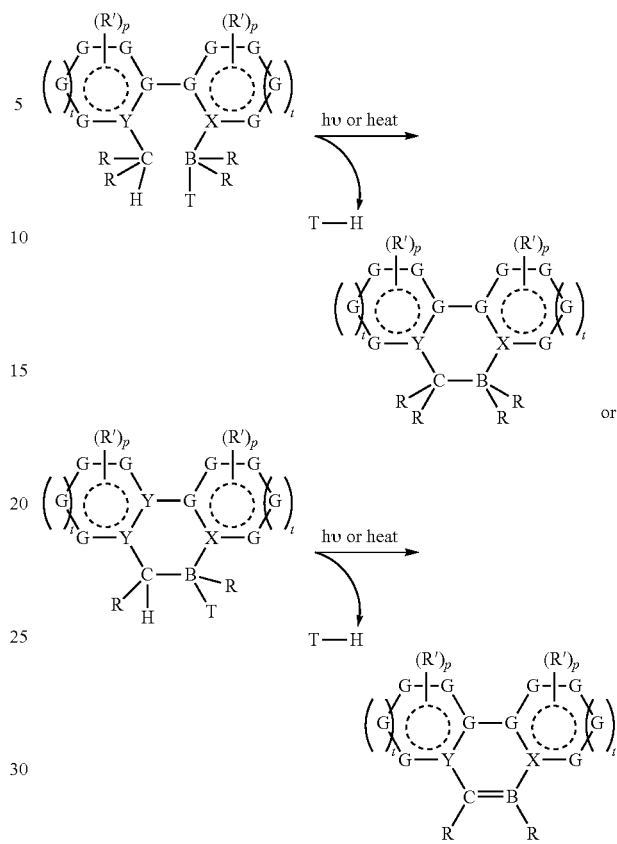

wherein G is independently carbon or a heteroatom (e.g., N, S, O, P)

X and Y are independently carbon or nitrogen;

T is a terminal ligand;

R is hydrogen, an aliphatic, or aryl (which includes heteroaryl) moiety that may be further substituted;

R' is hydrogen, an aliphatic or aryl (which includes heteroaryl) moiety that may be further substituted and is optionally a fused ring(s);

t is independently 0 or 1;

p is independently 0 to 10;

a dotted circle represents optional aromaticity, with the proviso that at least one moiety bonded to B, excluding the terminal ligand T, is a Lewis base that has donated a lone pair of electrons and is bonded to boron through a dative bond.

Examples of several reactants having the above general formulas, known herein as precursors, are provided herein. Structural formulae for specific examples are provided in Tables 1 and 2 and Schemes 1-8d, photophysical properties of selected elimination products are shown in Table 3, and synthetic information and characterization are provided in the Working Examples. In addition, details of successful elimination reactions of many exemplary precursors are provided. Structural formulae for the elimination products are also provided in Table 1, and synthetic information and characterization are provided in the Working Examples.

A person of skill in the art of the invention will recognize that in certain embodiments, elimination products can themselves be precursors, and photoelimination can continue if the conditions (e.g., substituents) are suitable. Accordingly, the inventors provide below general structures for monomer (i.e., monoboron), dimer (i.e., diboron) and trimer compound (i.e., triboron) compounds that may be formed by photoelimination reactions described herein. The inventors have demonstrated formation of dimer and trimer compounds by photoelimination of appropriate precursors, and have confirmed the products by high resolution mass spectroscopic methods.

Furthermore, dimer or trimer compounds formed by photoelimination can undergo further reactions to form tetramer and greater compounds, such as polycyclic molecules (e.g., aromatic polycycles, polycyclic π-conjugated azaborine molecules). Thus, it is appropriate to state that certain compounds according to the invention comprise the general monomer, dimer, or trimer structures set forth below, meaning that such a compound includes the selected structure, but is not limited to it, and may include additional structure(s). For example, certain compounds according to the invention may include multiple such dimer structures, or multiple such trimer structures. Monomer, dimer, trimer and other multimer compounds may be useful in the creation of films, particularly photo-patterned films. Such compounds may additionally or alternatively be useful for hydrogen storage, reversible hydrogenation applications, and/or conductive/charge transport/luminescent materials for optoelectronic devices.

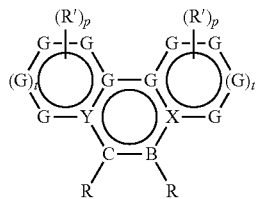

Monomer, where G, Y, X, t, p and R are as described above.

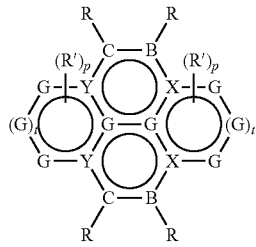

Dimer A

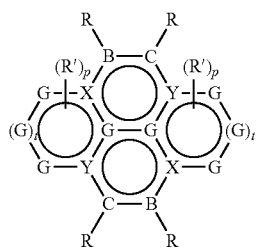

Dimer B

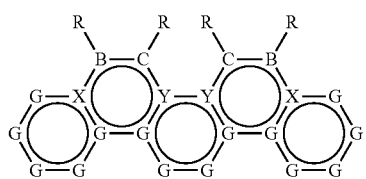

Dimer C.

For clarity, the top general formula of each pair depicted hereinabove has been shown in a simplified form with six-membered aromatic rings, and unsubstituted, but a person of skill in the art of the invention will recognize that five-membered rings, substituents, and/or larger numbers of heteroatoms are encompassed by aspects of the invention. This is more apparent from the bottom general formula of each pair.

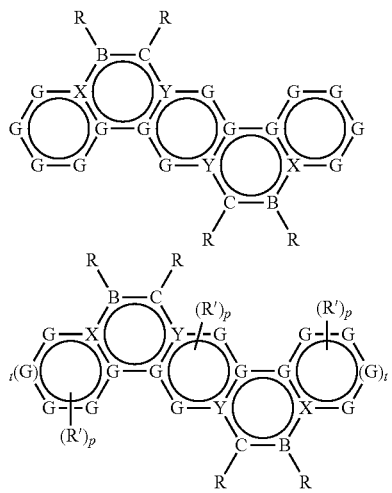

Dimer D

For clarity, the top general formula of each pair depicted hereinabove has been shown in a simplified form with six-membered aromatic rings, and unsubstituted, but a person of skill in the art of the invention will recognize that five-membered rings, substituents, and/or larger numbers of heteroatoms are encompassed by aspects of the invention. This is more apparent from the bottom general formula of each pair.

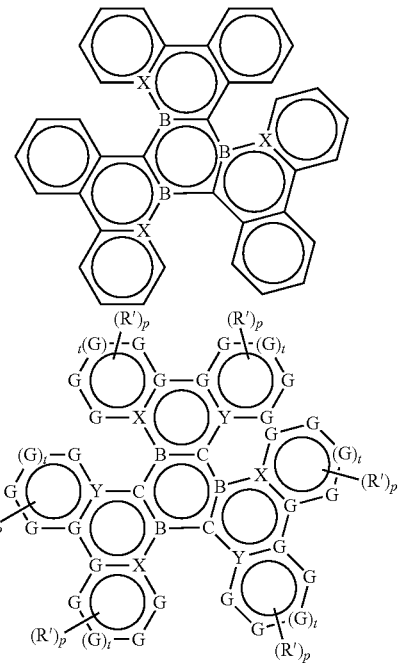

Trimer.

For clarity, the top general formula of each pair depicted hereinabove has been shown in a simplified form with six-membered aromatic rings, and unsubstituted, but a person of skill in the art of the invention will recognize that five-membered rings, substituents, and/or larger numbers of heteroatoms are encompassed by aspects of the invention. This is more apparent from the bottom general formula of each pair.

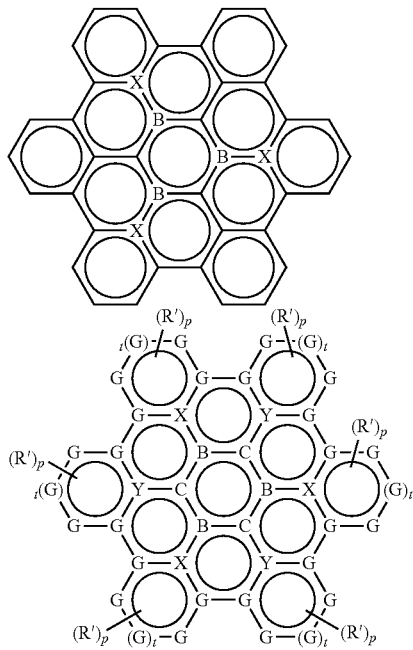

Fully Conjugated Trimer.

For clarity, the top general formula of each pair depicted hereinabove has been shown in a simplified form with six-membered aromatic rings, and unsubstituted, but a person of skill in the art of the invention will recognize that five-membered rings, substituents, and/or larger numbers of heteroatoms are encompassed by aspects of the invention. This is more apparent from the bottom general formula of each pair. Notably, Dimers A-D can also trimerize, forming 2D conjugated boron-containing polyaromatic systems.

Precursor compounds that were prepared as described herein were observed to be colourless except for BN-3 and BN-bpy-Pt1, which were light yellow in solution and in the solid state. They were air and thermally stable and did not show any appreciable change in toluene, when heated to 110° C. They were fully characterized by $^1$H, $^{13}$C, and $^{11}$B NMR, and/or high resolution mass spectra (HRMS) and/or elemental analysis data as described in the Working Examples. Crystal structures of BN-1, BN-3, BN-4, BN-4a, BN-bpy1, BC-1, SM1-aza, and DT1-aza were determined by single-crystal X-ray diffraction analysis as shown in FIGS. 1A to 1D, FIGS. 2, 4A, 11 and 12.

The synthesized precursors underwent elimination reactions either via the photoirradiation method described herein or via the pyrolysis method described herein and their corresponding elimination products were characterized as described in the Working Examples. Structural formulae of certain compounds of the invention are shown in the Schemes and Tables.

All of the precursor compounds are not fluorescent in the visible region of the spectra while their corresponding new azaborine analogues display bright green or yellow-green fluorescence in both solution and solid state (see FIGS. 3a-3d, 6a, 6b and Tables 1 and 2). Thus, the photoelimination reaction can also be followed conveniently by fluorescence spectroscopy. Compared to the previously reported BN-phenanthrene isomers 1-3, and phenanthrene (M. J. D. Bosdet, et al., Org. Lett. 2007, 9, 1395; M. J. S. Dewar, et al., J. Am. Chem. Soc. 1962, 84, 4884; M. J. S. Dewar, et al., J. Chem. Soc. 1958, 3073; M. J. D. Bosdet, et al., Angew. Chem. Int. Ed. 2007, 46, 4960; Sambursky, et al., Trans. Faraday Soc. 1940, 35, 427), the absorption spectra of BN-1a, BN-2a and BN-4a are red-shifted by 50-100 nm. The fluorescence spectra of the new BN-phenanthrene isomers are red-shifted by ~150-160 nm, relative to phenanthrene, 170-180 nm to BN-phenanthrene 1 (R'=H, R=Ph or H), and 40-50 nm to BN-phenanthrene 3 (R'=H, R=H, n-Bu, Ph, SiMe$_3$) (M. J. D. Bosdet, et al., Org. Lett. 2007, 9, 1395). The fluorescent quantum efficiency $\Phi_{FL}$ was determined to be 0.27, ~1.00, 0.16, ~1.00 for BN-1a, BN-2a, BN-3a, and BN-4a, respectively. The BN-2a and BN-4a compounds are the brightest emitters among all known BN-phenanthrene compounds.

BN-1a, BN-2a, BN-3a and (BN)2-1a are stable for days in the solid state and slowly degrade in solution upon exposure to air. In contrast, BN-4a decomposes rapidly in solution and in the solid state under air, presumably because of the reaction with oxygen (A. N. Lamm, et al., Mol. BioSyst. 2009, 5, 1303). The greater chemical stability of BN-1a to BN-3a and (BN)2-1a is clearly provided by the bulky mesityl group. Compounds BN-1a, BN-2a and BN-4a are previously unknown isomers of BN-phenanthrenes while compound (BN)2-1a is a new BN-replaced pyrene. Three other isomers of BN-phenanthrene and their derivatives (1-3) (R. Kwong, G. Kottas, International Patent, WO 2011/143563 A2; M. J. D. Bosdet, et al., Org. Lett. 2007, 9, 1395; M. J. S. Dewar, et al., J. Am. Chem. Soc. 1962, 84, 4884; M. J. S. Dewar, V. P. Kubba, R. Pettit, J. Chem. Soc. 1958, 3073; and M. J. D. Bosdet, et al., Angew. Chem. Int. Ed. 2007, 46, 4960) and one isomer of BN-pyrene (4) (M. J. D. Bosdet, et al., Angew. Chem. Int. Ed. 2007, 46, 4960) were reported previously and are shown below.

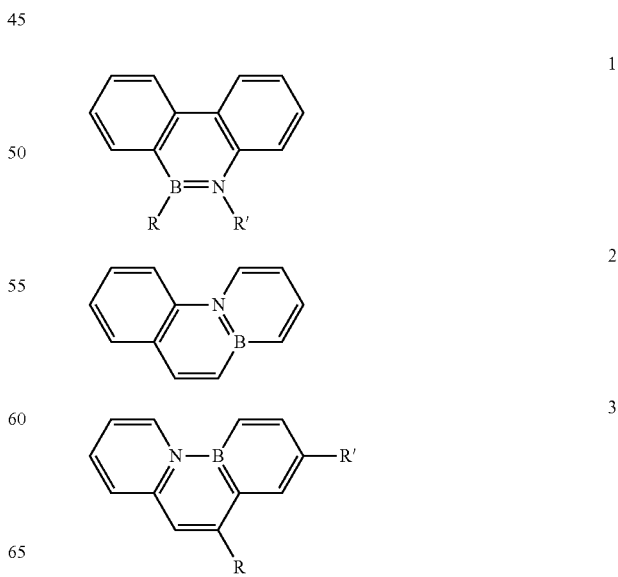

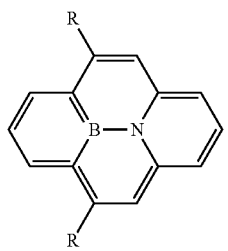

Structures of Previously Known BN-Phenanthrene and BN-Pyrene Compounds

Solution Phase Conversion of Precursors of Scheme 1 and 3 to Form Corresponding Azaborine Compounds by Photoelimination The precursor compounds shown in Scheme 1 Scheme 2a and Scheme 3 were converted to their corresponding aromatic azaborine monomer compounds by photoelimination reaction as illustrated by examples in Scheme 3. For example, when excited at 300 nm in dry toluene or benzene under nitrogen, the solutions of BN-1, BN-2 and BN-4 changed from colourless to bright yellow. In the UV-Vis spectra, a distinct new absorption band appeared at the 360 to 520 nm region and grew in intensity with increasing irradiation time, which accounts for the solution colour change (FIGS. 3a-3d). To elucidate the structural change, the photo-reaction was monitored by $^1$H and $^{11}$B NMR spectra (for examples, see FIG. 5a-5d). Upon irradiation, a free mesitylene molecule was observed and the $^1$H NMR spectra of BN-1 and BN-2 underwent a clean and distinct change to those of BN-1a and BN-2a (Scheme 3). The most distinct chemical shift change was the methylene protons that shifted from 3.02 ppm in BN-1 and 2.76 ppm in BN-2 to 7.35 ppm in BN-1a and BN-2a, along with the total integration change from 2 to 1 proton. The $^{11}$B chemical shift also experienced a distinct change from 1.6 ppm in BN-1 and 1.2 ppm in BN-2, typical for tetrahedral boron centres, to 35.5 ppm in BN-1a and 35.0 ppm in BN-2a, similar to some of the previously reported $^{11}$B chemical shifts in 1,2-azaborine compounds (M. Lepeltier, et al., Chem. Commun. 2010, 46, 7007; T. Taniguchi, et al., Organometallics, 2010, 29, 5732; and J. Pan, et al., Organometallics, 2004, 23, 5626). BN-1a and BN-2a were fully characterized by NMR and HRMS analyses. Quantum efficiency for the BN-2→BN-2a conversion was determined to be ~4.4%, which is fairly efficient for photochemical reactions. Elimination of methane and formation of BN-4a from BN-4 were confirmed by NMR and HRMS data. However, the BN-4 reaction was not as clean as BN-1 and BN-2. With prolonged irradiation, side products other than BN-4a were evident in the $^1$H NMR spectra, which have not yet been fully characterized. Benzothiazole compound BN-3 underwent a similar photoelimination as BN-1, upon irradiation of BN-3 at 350 nm, compound BN-3a formed as the major product with the elimination of one mesitylene (Scheme 3). NMR and HRMS data established that BN-3a is an analogue of BN-1a and BN-2a. The structures of BN-1a, BN-2a, BN-3a and BN-4a are shown in Scheme 3. Bright yellow-orange crystals of BN-3a were obtained and the crystal structure of BN-3a was successfully determined by X-ray diffraction analysis and shown in FIG. 4b. The mesityl ring was shown to be approximately perpendicular to the azaborine ring (the dihedral angle between the two rings is 102.1°). The B—N, B—C and C—C bond lengths of the azaborine ring in BN-3a from the X-ray data were found to be similar to those in the previously reported azaborine compounds (H. Braunschweig, et al., Angew. Chem. Int. Ed. 2012, 51, 10034; T. Taniguchi, et al., Organometallics, 2010, 29, 5732; E. R. Abbey, et al., J. Am. Chem. Soc. 2008, 130, 7250; and M. J. D. Bosdet, et al., Org. Lett. 2007, 9, 1395).

Diboron compound (BN)2-1 underwent a similar photoelimination reaction, forming the diboron azaborine compound (BN)2-1a as shown in Scheme 3a. (BN)2-1a displays a red color and was characterized by HRMS spectroscopy. Solid Phase Conversion of Precursors in Scheme 1 and 3 to the Corresponding Azaborine Compounds by Photoelimination in a Polymer Matrix.

As described above, in certain embodiments, precursor compounds may readily undergo the photoelimination reaction described herein in the solid state or in a polymer film such as, for example, poly(methyl methacrylate) (PMMA) or poly(N-vinylcarbazole) (PVK). UV-Vis spectra of the precursor compounds in PMMA films undergo similar changes upon irradiation by UV light to those recorded for the same compounds in solution (e.g., in toluene), supporting that the same azaborine species were formed. UV-Vis spectra showing conversion of BN-2 to BN-2a, and BN-4 to BN-4a in PMMA film (10 wt %) with UV irradiation are shown in FIGS. 6A-6D.

Patterned fluorescent films can be prepared using compounds of the embodiments of the invention. This patterning is possible because of the contrasting non-emissive and emissive properties of the precursor compounds relative to their corresponding elimination products. Some examples were prepared of patterned fluorescent films and the resultant films had high contrast. Such films can be made by casting a precursor doped PMMA film on a glass substrate, positioning a mask between the film and a light source (e.g., covering the film with a mask), and exposing it to UV light. The masked areas remained non-luminescent, and the areas that were exposed to UV light were glowing a yellowing-green colour. Examples of such patterned films are shown in FIGS. 6A-6D.

A prototype electroluminescent device with the structure of ITO/PVK:3 wt % of BN-3/Ca has been fabricated. BN-3 was converted to BN-3a, after BN-3/PVK was spin-cast to the ITO substrate, by irradiation at 265 nm. This device emitted a yellow-green color after it was turned on, see photograph in FIG. 6E. This demonstrates that the photoelimination reaction described herein can be used to generate fluorescent dopants in conducting or semiconducting polymers for applications in electroluminescent devices or other optoelectronic devices.

Absorption and fluorescence spectra of BN-1a, BN-2a and BN-4a are similar, despite the different substituent groups. This similarity is an indication that the low energy electronic transitions in these molecules are most likely dictated by the BN-phenanthrene unit. This idea has been confirmed by computational studies. HOMO and LUMO levels of BN-1a, BN-2a, BN-4a and BN-5a are localized on the BN-phenanthrene ring with no or little contributions from substituent groups. Similarly, for the benzothiazolyl BN-3a compound, the HOMO and LUMO levels are localized at the BN-substituted arene ring. Thus, the fluorescence of the new azaborine compounds can be attributed to a π→π* transition of the π-conjugated azaborine unit. An impact of BN replacement in phenanthrene was narrowing the HOMO-LUMO gap and decreasing the π→π* transition energy. This finding is in agreement with the general trend observed previously for azaborine compounds (M. J. D. Bosdet, et al., *Org. Lett.* 2007, 9, 1395; A. Chrostowska, et al., *J. Am. Chem. Soc.* 2012, 134, 10279; M. J. D. Bosdet, et al., *Angew. Chem. Int. Ed.* 2007, 46, 4940), with the exception of BN-phenanthrene 1 (R=R'=H) that has a higher HOMO-LUMO transition energy than phenanthrene (M. J. D. Bosdet, et al., *Org. Lett.* 2007, 9, 1395; M. J. S. Dewar, et al., *J. Chem. Soc.* 1958, 3073).

Conversion of the Precursors in Scheme 4 to the Corresponding Azaborine Trimer Compounds by Photoelimination According to Scheme 2.

Precursor compounds that comprise a $BH_3$ moiety are shown in Schemes 2 and 4. Such precursors can undergo quantitative photoelimination of hydrogen molecules, forming trimer compounds. Presumably, the monomer shown in Scheme 2 was formed first, which subsequently converted to the trimer by eliminating 3 more equivalents of hydrogen molecules per trimer. Several such trimer products have been synthesized, and characterized by HRMS spectroscopy (FIGS. 7B and 7C). Examples of such trimers that have been fully characterized are shown in Scheme 5. Formation of hydrogen molecules was confirmed by $^1H$ NMR spectra. Trimer products may have poor solubility in organic solvents unless a higher aliphatic substituent group is present.

Figure 7A:
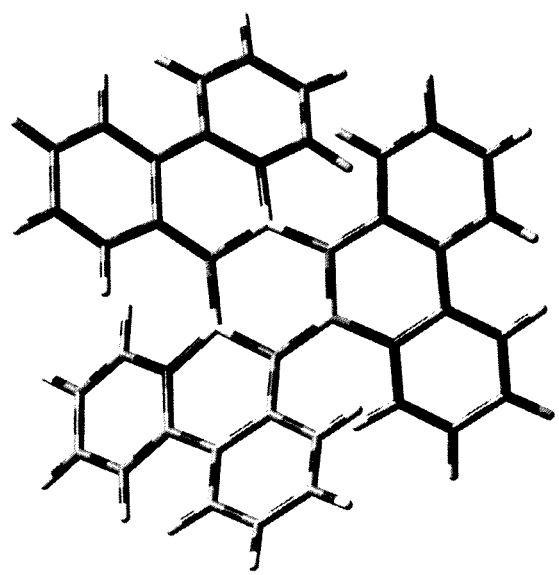
FIG. 7A shows a calculated structure of BN-5b optimized by DFT computation.

A calculated structure of BN-5b optimized by DFT (discrete Fourier transform) computation is shown in FIG. 7a. For diboron compounds such as (BN)2-2, photoelimination of hydrogen molecules can lead to polyboron species such as (BN)2-2a shown in Scheme 5a.

Conversion of Azaborine Trimers to Fully Conjugated BN- or B-Substituted Polyaromatic Molecules Some of the azaborine trimer compounds (e.g. BN-5b in Scheme 5 and (BN)2-2a in Scheme 5a can undergo oxidative dehydrogenation reactions readily forming a fully conjugated species such as BN-5c and BN-6c shown in Scheme 6. Oxidative dehydrogenation is a well-established synthetic method for converting hexa-phenyl substituted benzene and its derivatives to fully conjugated graphenes (M. D. Watson, et al., *Chem. Rev.* 2001, 101, 1207; and A. Stabel, et al., *Angew. Chem. Int. Ed.*, 1995, 34, 1609). The same procedure has been shown to work well for the BN-replaced molecules. Other potential BN-replaced graphenes or B-replaced fully conjugated polyaromatic molecules are provided in Table 2.

Embodiments Having Metal-Functionalized Azaborine Compounds

The backbone of BN-azaborine compounds may be modified by attaching metal-chelate units (e.g., main-group metal chelate units, transition metal chelate units, or rare earth metal chelate units). Two examples are illustrated in Scheme 7. Modification of the backbone by such metal chelates can effectively tune the colors of the precursor molecules. In some embodiments, the presence of metal-substituents shifts the excitation energy of the precursor to the visible region, making it possible to drive the photoelimination reaction using visible light. In addition, the presence of metal-substituents introduces properties such as phosphorescence and electron transport to the molecule. Oxidative dehydrogenation of the metal modified compounds could lead to the formation of fully conjugated metal-functionalized molecules such as the one example shown in Scheme 7b. Additional examples of such compounds with metal chelate units can be found in Table 2.

In summary, an unprecedented photoelimination reaction has been discovered, which can be used effectively in constructing, for example, π-conjugated polycyclic azaborine compounds. In some embodiments this is done by eliminating a R—H molecule from a $BR_2$—$CH_2$ unit. This photoelimination is applicable to solid substrates such as, for example, B,N-heterocycle doped PMMA or PVK films. This solid phase reaction makes possible a simple and convenient method for in-situ generation of polycyclic azaborine compounds in polymer substrates and for creating patterned fluorescent polymer films by light, which may find applications in fabrication of optoelectronic devices.

In some embodiments of the invention, an EL device includes one or more charge transport layers interposed between an emitter comprising a luminescent compound as described herein and one or both of the electrodes. Such charge transport layer(s) are employed in prior art systems with inorganic salt emitters to reduce the voltage drop across the emitter. In a first example of such a device, layers are arranged in a sandwich in the following order: first electrode, charge transport layer, emitter and host, second charge transport layer, and second transparent electrode. In an embodiment of this type, a substrate of glass, quartz or the like is employed. A reflective metal layer (corresponding to the first electrode) is deposited on one side of the substrate, and an insulating charge transport layer is deposited on the other side. The emitter layer including a compound of the invention is deposited on the charge transport layer, preferably by vacuum vapor deposition, though other methods may be equally effective. A transparent conducting electrode (e.g., ITO) is then deposited on the emitter layer. An effective voltage is applied to produce electroluminescence of the emitter.

In a second example of an EL device of the invention, a second charge transport layer is employed, and the sandwich layers are arranged in the following order: first electrode, first charge transport layer, emitter and host, second charge transport layer and second, transparent electrode.

Electroluminescent devices of the invention may include one or more of the emitting compounds described herein. In some embodiments of the invention, an electroluminescent device such as a flat panel display device may include not only an emitting compound as described herein, but may be a multiple-color display device including one or more other emitters. The other emitters may emit in other light ranges, e.g., red, green, and/or be stacked relative to each other. Convenient materials, structures and uses of electroluminescent display devices are described in Rack, P. D. et al., "Materials used in electroluminescent displays" MRS Bulletin (1996) 21(3): 49-58.

The invention further provides methods employing compounds of the invention to harvest photons, and corresponding devices for such use. Spectroscopic studies have demonstrated that compounds of the invention have high efficiency to harvest photons and produce luminescence. In general, when such compounds are excited by light, a charge separation occurs within the molecule; a first portion of the molecule has a negative charge and a second portion has a positive charge. Thus the first portion acts as an electron donor and the second portion as an electron acceptor. If recombination of the charge separation occurs, a photon is produced and luminescence is observed. In photovoltaic devices, recombination of the charge separation does not occur; instead the charges move toward an anode and a cathode to produce a potential difference, from which current can be produced.

Molecules with the ability to separate charges upon light initiation are useful for applications such as photocopiers, photovoltaic devices and photoreceptors. Photoconductors provided by the present invention are expected to be useful in such applications, due to their stability and ability to be spread into thin films. Related methods are encompassed by the invention.

Organic semiconducting materials can be used in the manufacture of photovoltaic cells that harvest light by photo-induced charge separation. To realize an efficient photovoltaic device, a large interfacial area at which effective dissociation of excitons occurs must be created; thus an electron donor material is mixed with an electron acceptor material. (Here, an exciton is a mobile combination of an electron and a hole in an excited crystal, e.g., a semiconductor.) Luminescent compounds as semiconductors are advantageous due to their long lifetime, efficiency, low operating voltage and low cost. Photocopiers use a light-initiated charge separation to attract positively-charged molecules of toner powder onto a drum that is negatively charged.

Certain embodiments of the invention provide compounds suitable for use in biological and/or medical imaging. For example, the compounds' luminescent properties may be useful in vivo or in vitro in visualizing cell substructures or tissue superstructures, such as tumours or other anomalies.

Figure 1B:
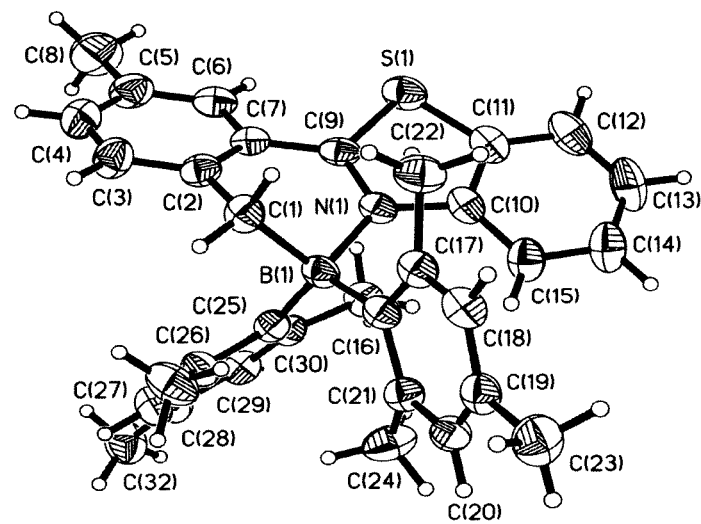
FIG. 1B shows the structure of BN-3.
Figure 1C:
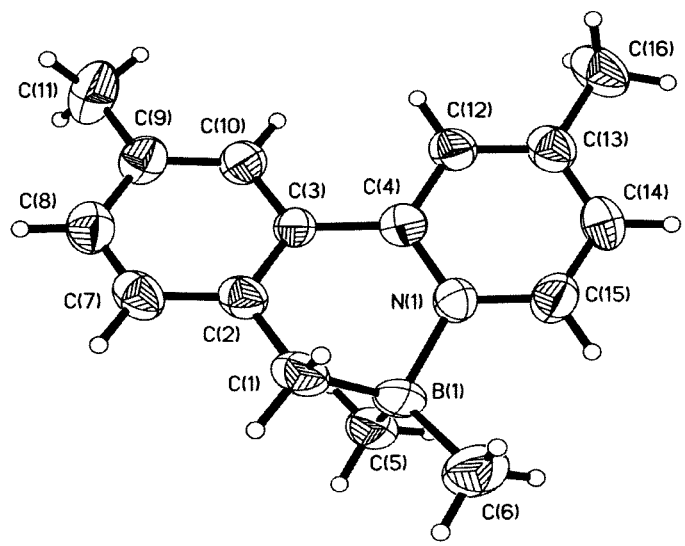
FIG. 1C shows the crystal structure of BN-4.
Figure 1D:
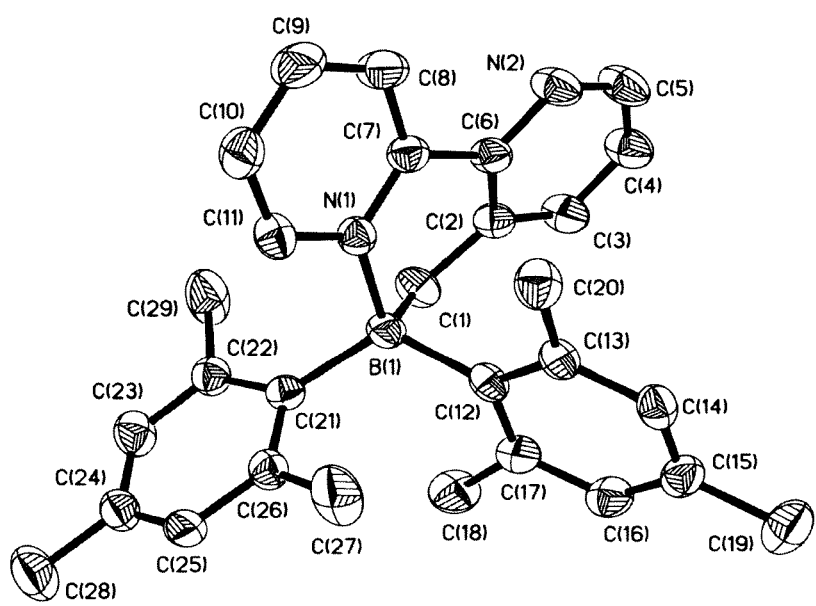
FIG. 1D shows the crystal structure of BN-bpy1.
Figure 2:
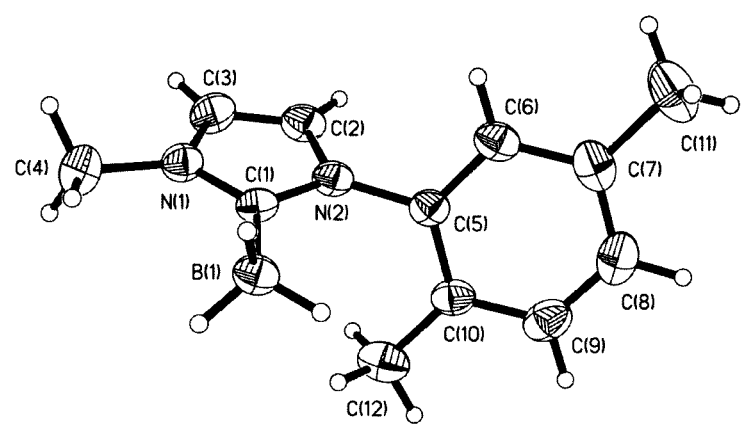
FIG. 2 shows the crystal structure of BC-1, where R=Me.
Figure 3A:
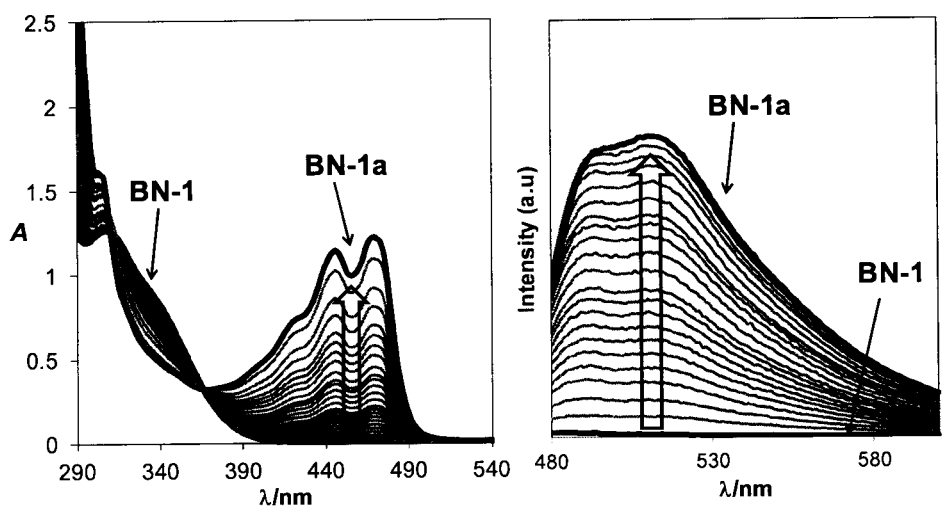
FIG. 3A displays absorption (left) and fluorescence (right) spectra showing the quantitative conversion of BN-1 to BN-1a upon irradiation by light (300 nm) in toluene.
Figure 3B:
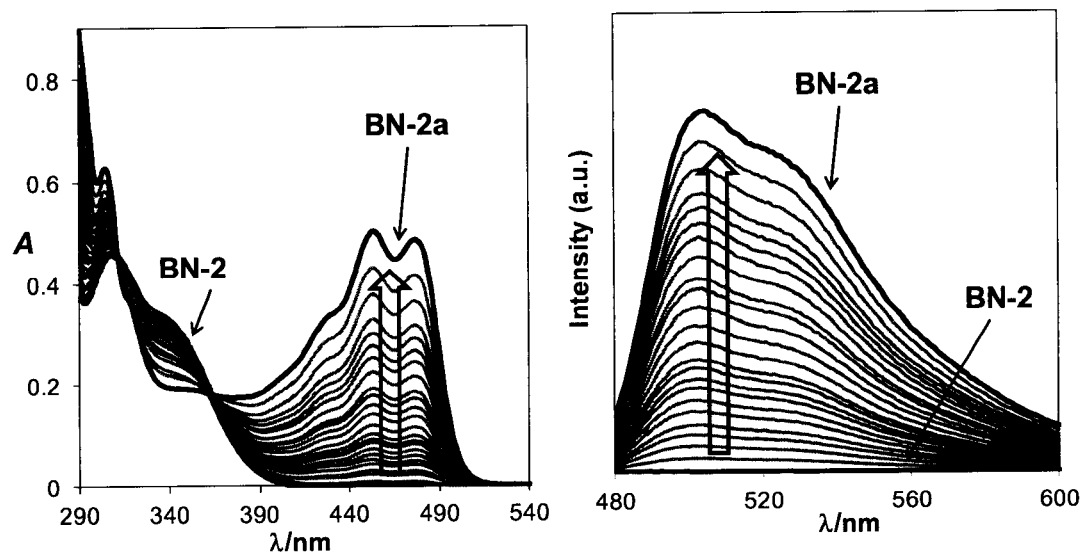
FIG. 3B displays absorption (left) and fluorescence (right) spectra showing the quantitative conversion of BN-2 to BN-2a upon irradiation by light (300 nm) in toluene.
Figure 3C:
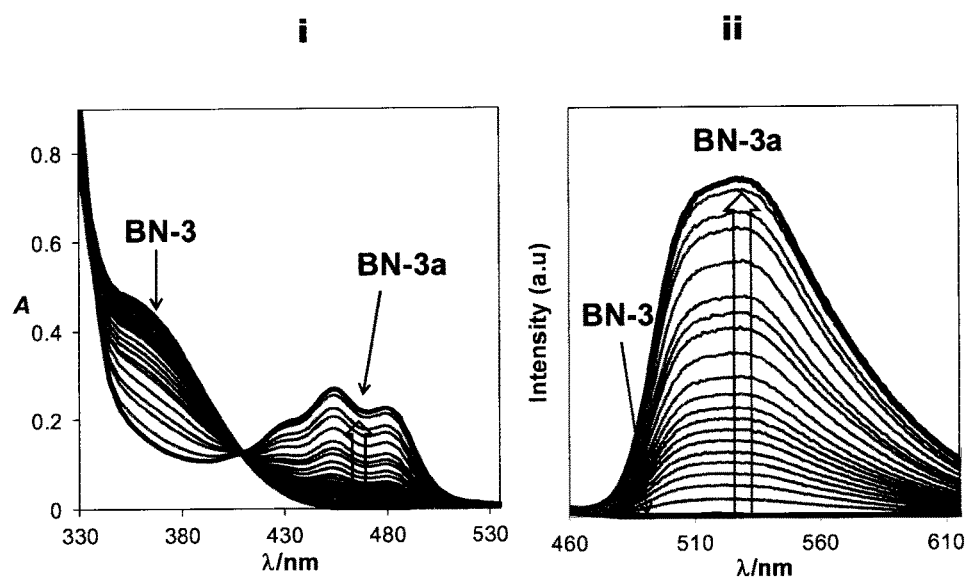
FIG. 3C displays absorption (left) and fluorescence (right) spectra showing the quantitative conversion of BN-3 to BN-3a upon irradiation by light (350 nm) in toluene.
Figure 3D:
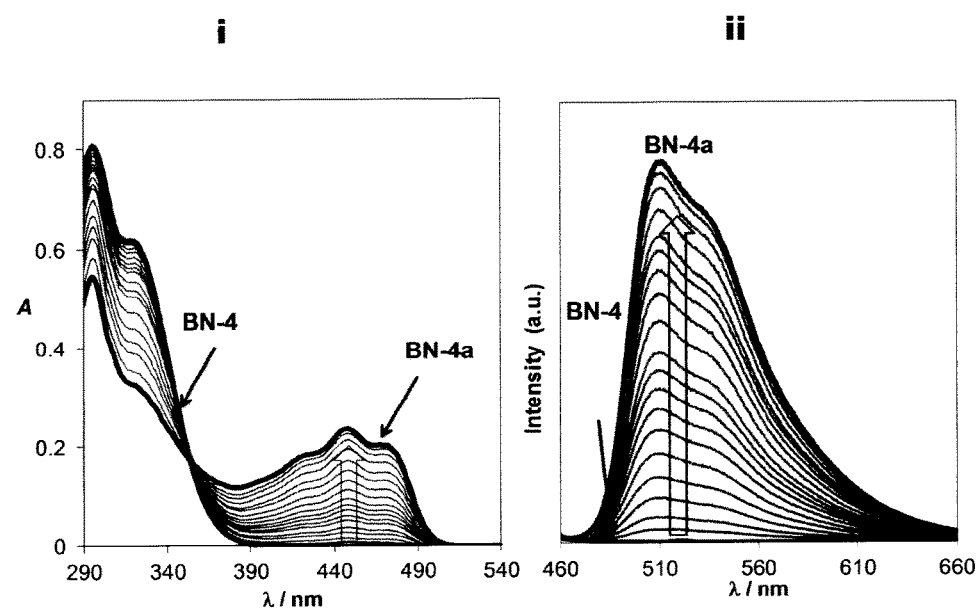
FIG. 3D displays absorption (left) and fluorescence (right) spectra showing the quantitative conversion of BN-4 to BN-4a upon irradiation by light (300 nm) in toluene.
Figure 3E:
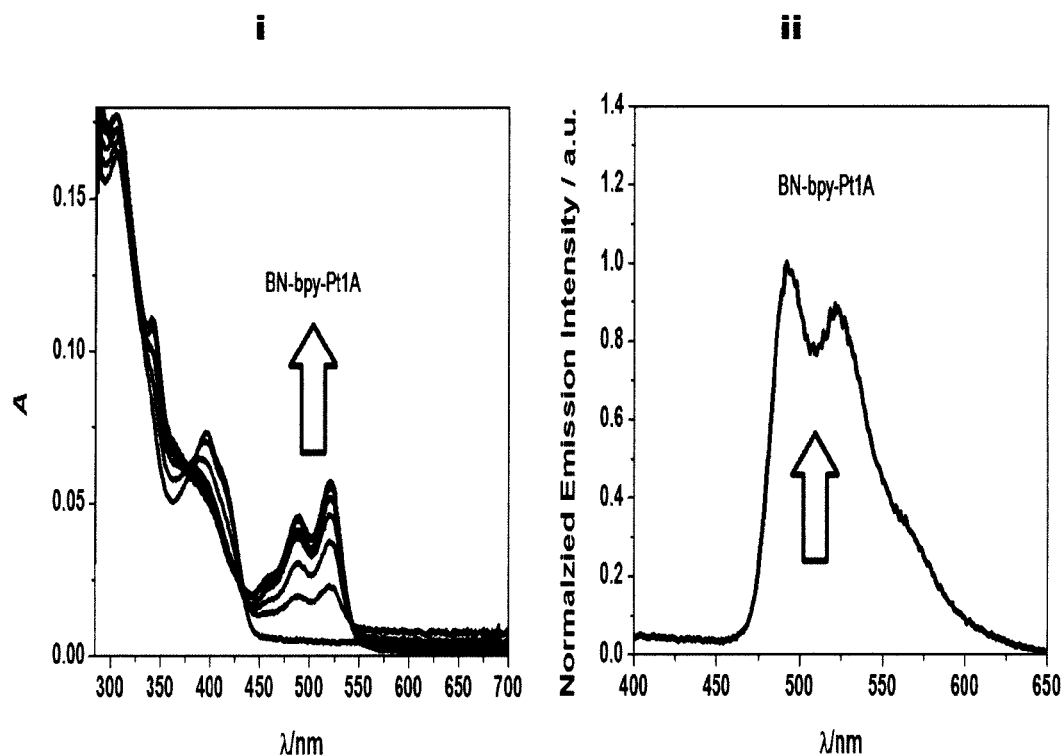
FIG. 3E displays absorption (left) and phosphorescent (right) (right) showing the quantitative conversion of BN-bpy-Pt1 to BN-bpy-Pt1a upon irradiation by light (350 nm) in toluene.
Figure 4A:
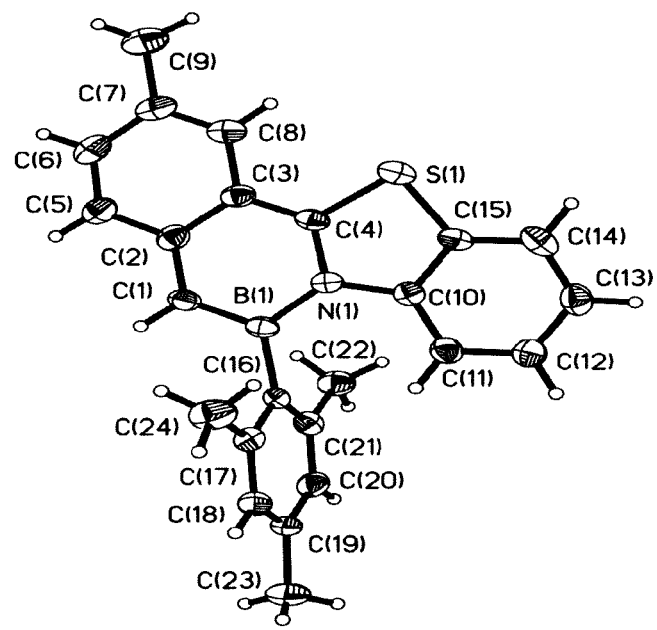
Figure 5A:
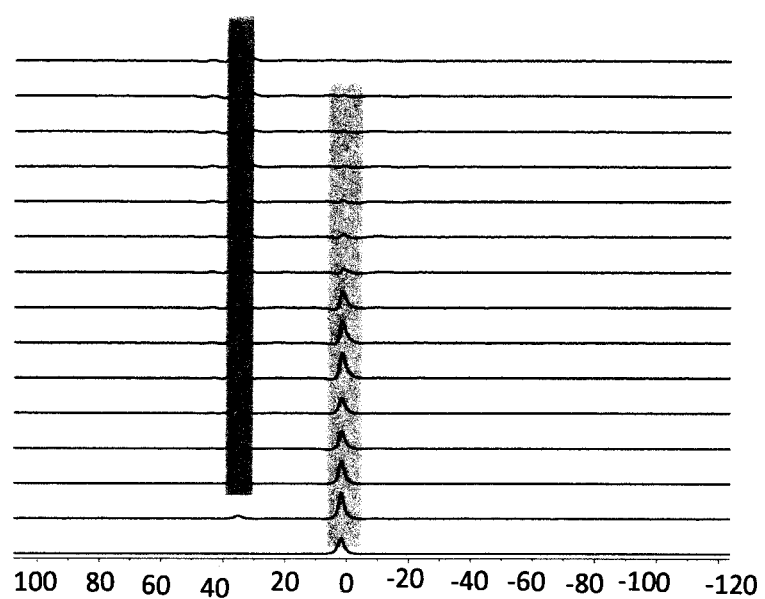
FIG. 5A displays $^{11}$B NMR spectra showing clean conversion of BN-2 (bottom) to BN-2a (top) in $C_6D_6$ at ambient temperature and 300 nm irradiation.
Figure 5B:
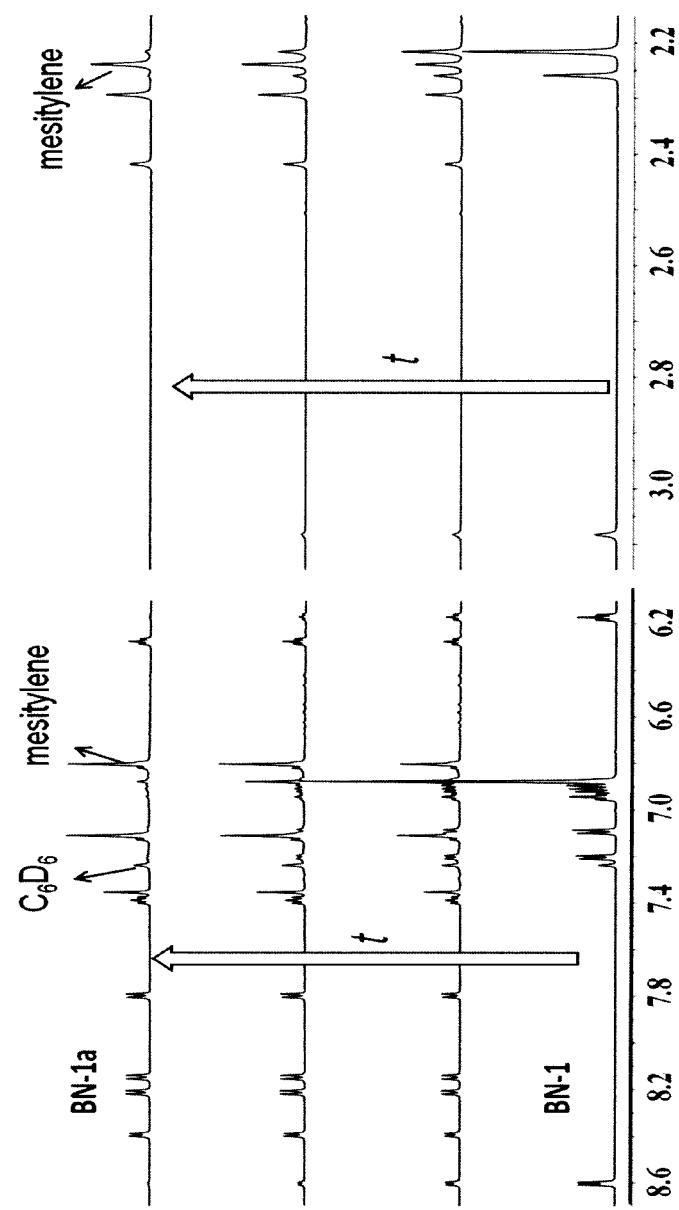
FIG. 5B displays $^1$H NMR spectra showing clean conversion of BN-1 to BN-1a and the appearance of mesitylene, in $C_6D_6$ at ambient temperature and 300 nm irradiation.
Figure 5C:
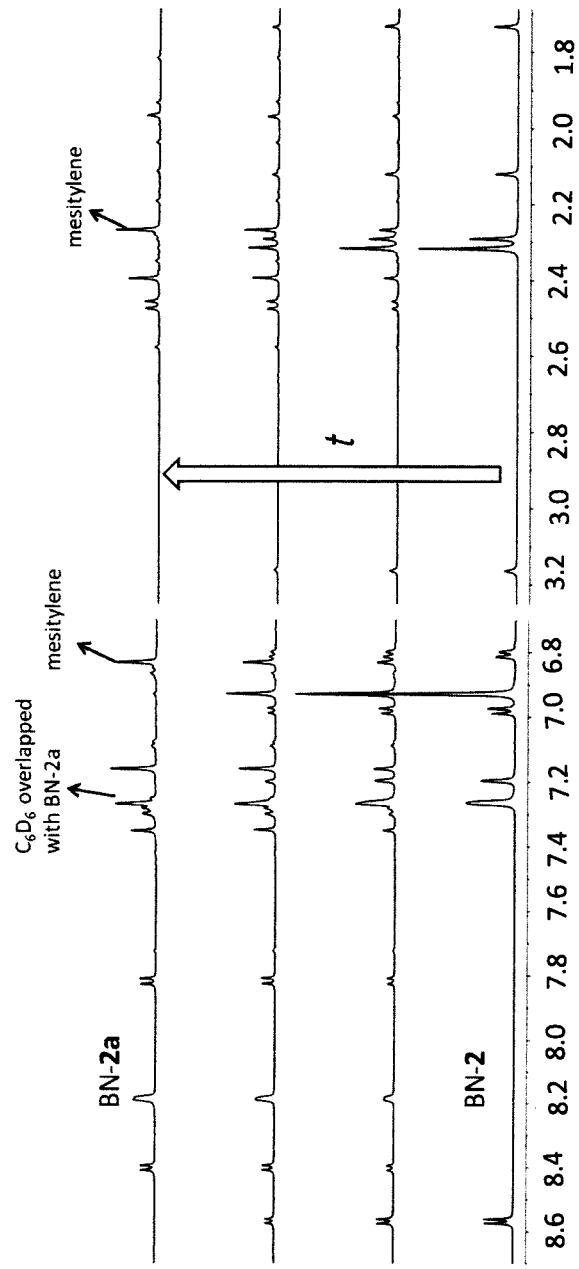
FIG. 5C displays $^1$H NMR spectra showing clean conversion of BN-2 to BN-2a and the appearance of mesitylene, in $C_6D_6$ at ambient temperature and 300 nm irradiation.
Figure 5D:
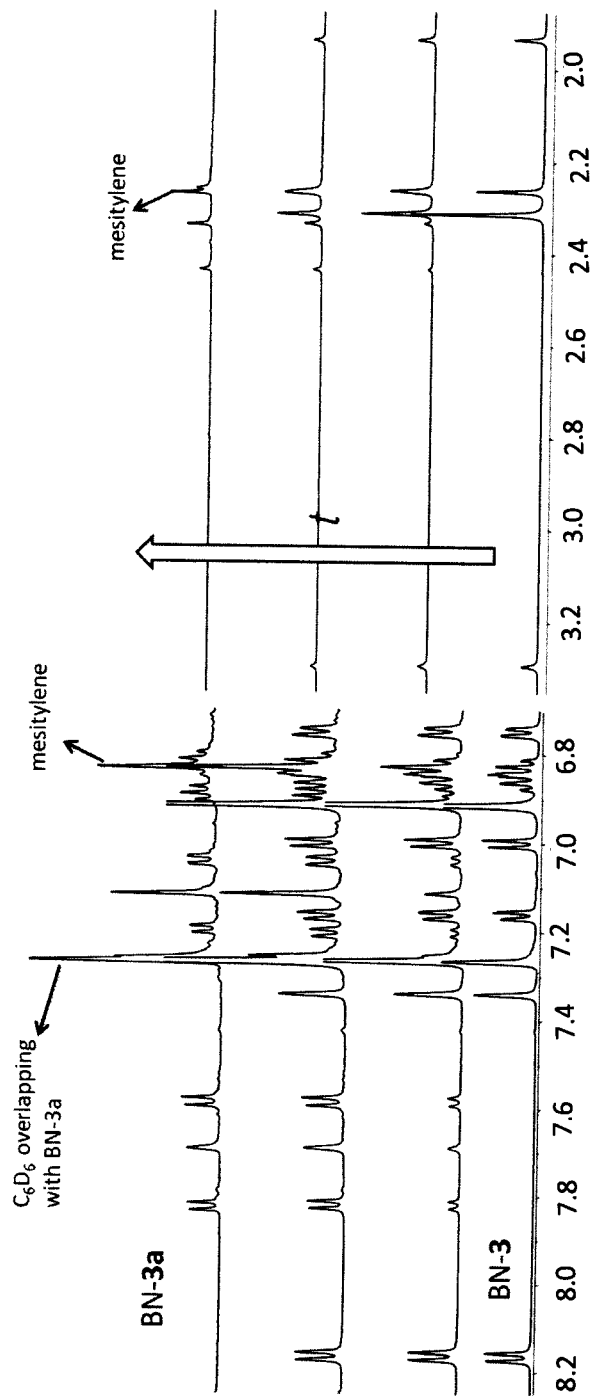
FIG. 5D displays $^1$H NMR spectra showing clean conversion of BN-3 to BN-3a and the appearance of mesitylene, in $C_6D_6$ at ambient temperature and 300 nm irradiation.
Figure 6A:
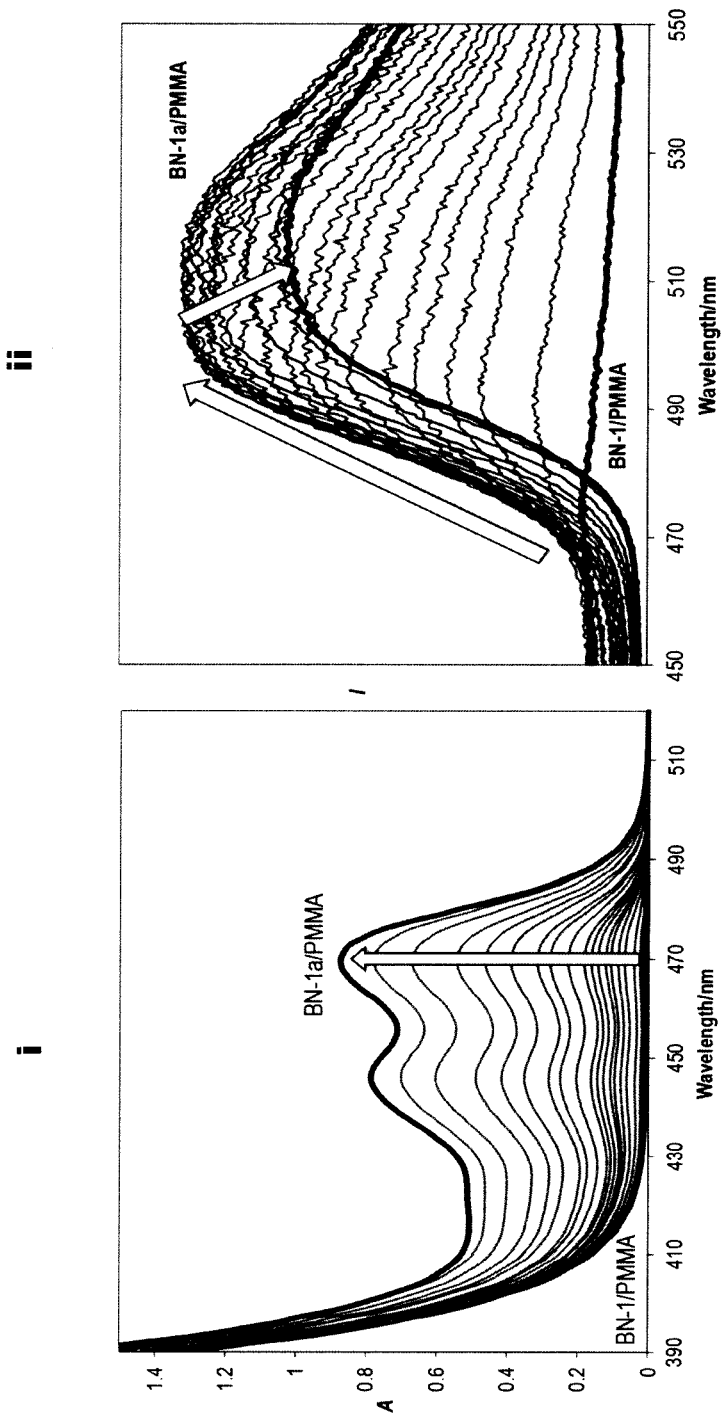
FIG. 6A displays absorption (left) and fluorescence spectra (right) showing the quantitative conversion of BN-1 to BN-1a upon irradiation by light (350 nm) in PMMA (10 wt %)
Figure 6B:
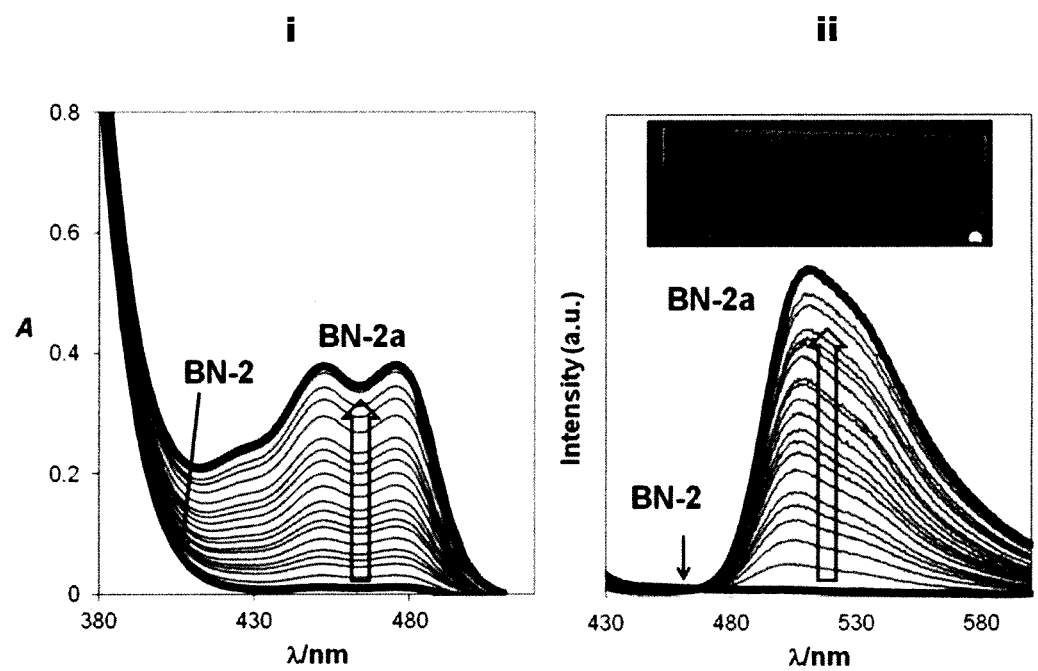
FIG. 6B displays absorption (left) and fluorescence spectra (right) showing the quantitative conversion of BN-2 to BN-2a upon irradiation by light (350 nm) in PMMA (10 wt %). An inset photograph shows a patterned fluorescent film of BN-2a in PMMA film on a glass slide (the dark area is BN-2/PMMA film that was not irradiated).
Figure 6C:
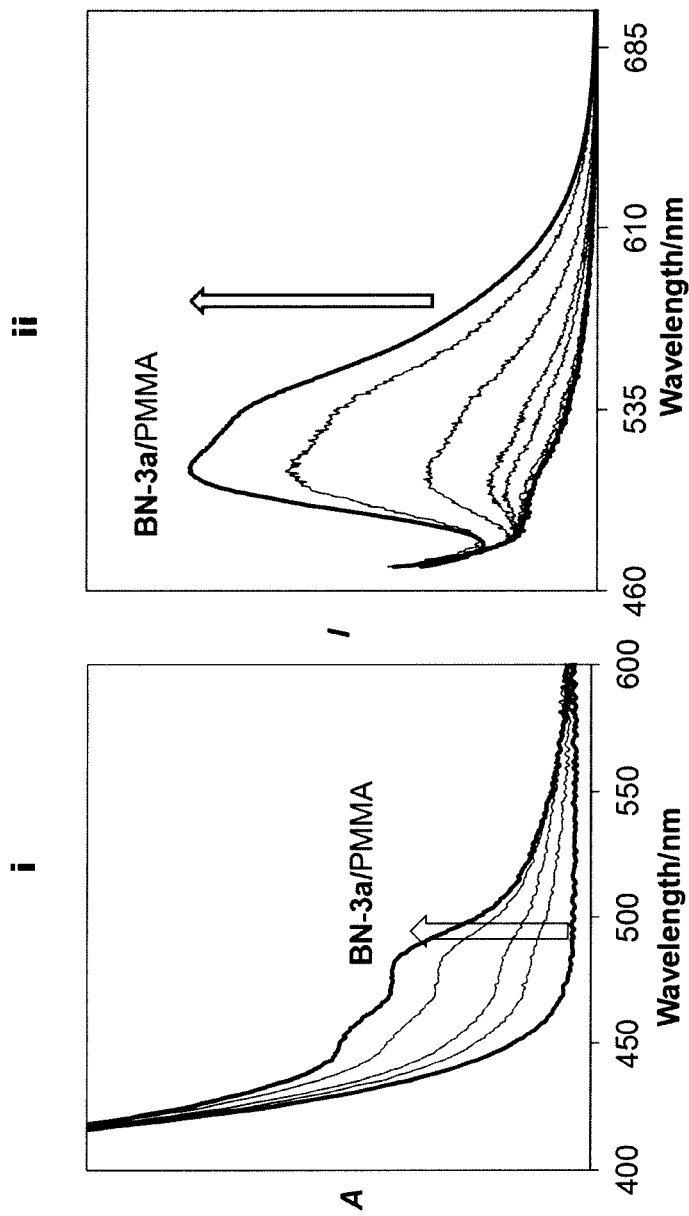
FIG. 6C displays absorption (left) and fluorescence spectra (right) showing quantitative conversion of BN-3 to BN-3a upon irradiation by light (350 nm) in PMMA (10 wt %)
Figure 6D:
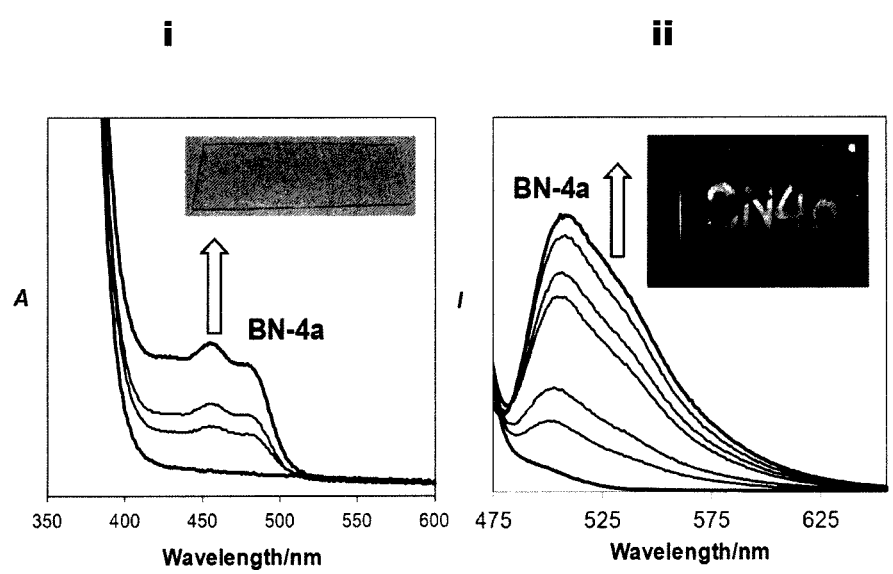
FIG. 6D displays absorption (left) and fluorescence spectra (right) showing quantitative conversion of BN-4 to BN-4a upon irradiation by light (350 nm) in PMMA (10 wt %). An inset photograph shows a patterned fluorescent film of BN-4a in PMMA film on a glass slide (the dark area is BN-4/PMMA film that was not irradiated)
Figure 6E:
FIG. 6E displays a photograph showing a yellowish-green emission color of an electroluminescent device based on a single-layer PVK:3 wt % BN-3a, generated by photoelimination of PVK:3 wt % BN-3 on an ITO substrate.
Figure 8:
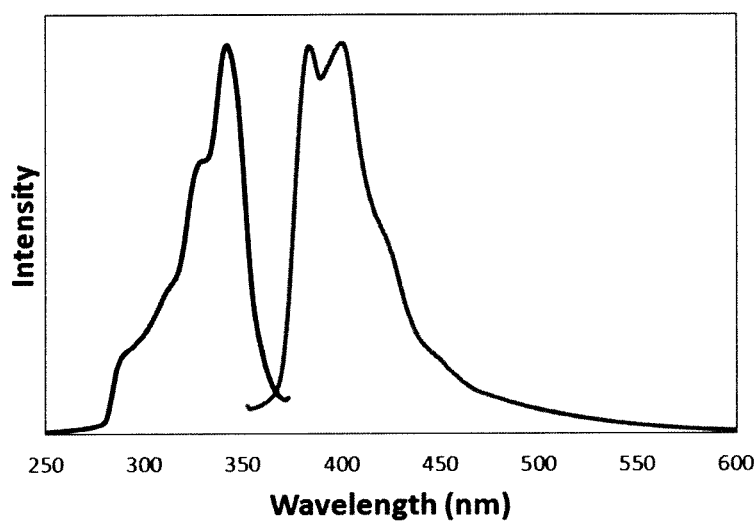
FIG. 8 shows excitation (left) and emission (right) spectra of azaborine compound SM1-aza at $5 \times 10^{-6}$M in toluene.
Figure 9:
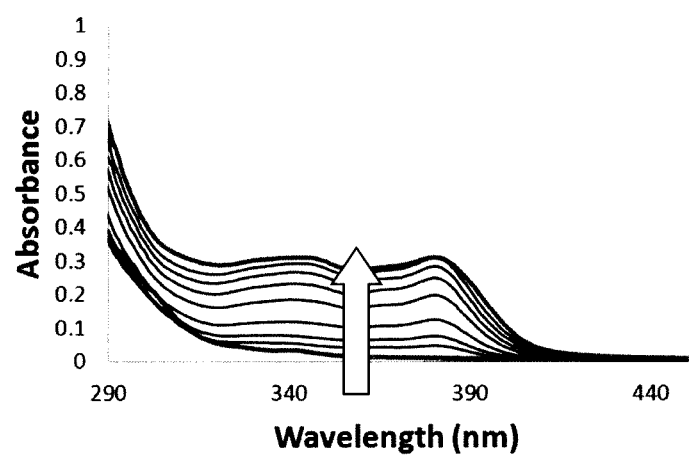
FIG. 9 shows Absorption spectra following the photoreaction of SM1 for a 5 hour irradiation period at $1 \times 10^{-3}$M in toluene.
Figure 10:
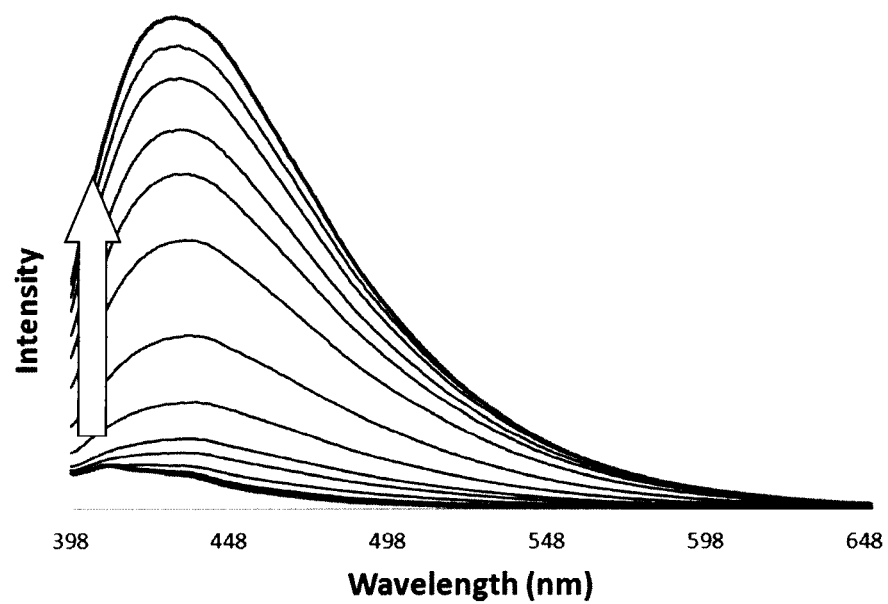
FIG. 10 shows a fluorescence spectra following a photoreaction of SM1 for a 5 hour irradiation period at $1 \times 10^{-4}$ M in toluene.
Figure 11:
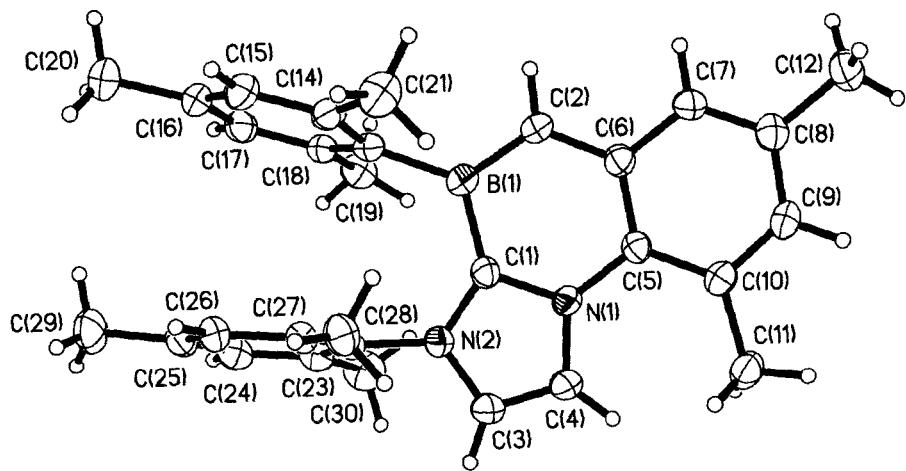
FIG. 11 shows the crystal structure of SM1-aza.
Figure 12:
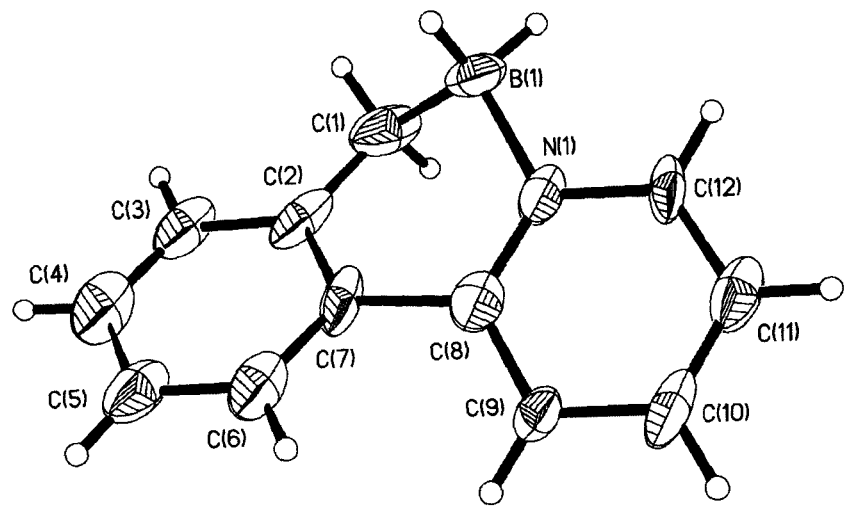
FIG. 12 shows the crystal structure of DT1.

Referring to FIG. 1A, a crystal structure of BN-1 is shown. Referring to FIG. 1B, a crystal structure of BN-3 is shown. Referring to FIG. 1C, a crystal structure of BN-4 is shown. Referring to FIG. 1D, a crystal structure of BN-bpy1 is shown. Referring to FIG. 2, a crystal structure of BC-1, where R=Me, is shown. Referring to FIG. 3A, an absorption spectra and fluorescence spectra are shown indicating that quantitative conversion of BN-1 to BN-1a upon irradiation by light (300 nm) in toluene was achieved. Referring to FIG. 3B, absorption and fluorescence spectra are shown indicating quantitative conversion of BN-2 to BN-2a upon photoirradiation. Referring to FIG. 3C, absorption and fluorescence spectra are shown indicating quantitative conversion of BN-3 to BN-3a upon photoirradiation. Referring to FIG. 3D, absorption and fluorescence spectra are shown indicating quantitative conversion of BN-4 to BN-4a upon photoirradiation. Referring to FIG. 3E, absorption and phosphorescent spectra are shown indicating quantitative conversion of BN-bpy-Pt1 to BN-bpy-Pt1a upon photoirradiation. Referring to FIG. 4A, a crystal structure of compound BN-3a is shown. Referring to FIG. 5A, a $^{11}$B NMR spectra is provided showing clean conversion of BN-2 (bottom) to BN-2a (top) in $C_6D_6$ at ambient temperature and 300 nm irradiation. Referring to FIG. 5B, $^1$H NMR the appearance of a peak for mesitylene. Referring to FIG. 5C, $^1$H NMR spectra are shown indicating clean conversion of BN-2 to BN-2a upon photoirradiation and showing the appearance of a peak for mesitylene. Referring to FIG. 5D, $^1$H NMR spectra are shown indicating clean conversion of BN-3 to BN-3a upon photoirradiation and showing the appearance of a peak for mesitylene. Referring to FIG. 6A, absorption and fluorescence spectra are shown indicating quantitative conversion of BN-1 to BN-1a upon photoirradiation in PMMA. Referring to FIG. 6B, absorption and fluorescence spectra are shown indicating quantitative conversion of BN-2 to BN-2a upon photoirradiation in PMMA. Also, an inset photograph is provided showing a patterned fluorescent film of BN-2a in PMMA film on a glass slide where the dark area is BN-2/PMMA film that was not photoirradiated. Referring to FIG. 6C, absorption and fluorescence spectra are shown indicating quantitative conversion of BN-3 to BN-3a upon photoirradiation in PMMA. Referring to FIG. 6D, absorption and fluorescence spectra are shown indicating quantitative conversion of BN-4 to BN-4a upon photoirradiation in PMMA. An inset photograph shows a patterned fluorescent film of BN-4a in PMMA film on a glass slide where the dark area is BN-4/PMMA film that was not photoirradiated. Referring to FIG. 6E, a photograph is displayed showing a yellowish-green emission color of an electroluminescent device based on a single-layer PVK:3 wt % BN-3a, generated by photoelimination of PVK:3 wt % BN-3 on an ITO substrate. Referring to FIG. 7A, a DFT optimized structure of BN-5b is provided. In conducted studies, the actual high resolution mass spectroscopy (HRMS) spectrum of BN-5b showed identical peaks to those of a calculated pattern based on the displayed DFT optimized structure of FIG. 7A. Referring to FIG. 8, excitation and emission spectra are provided of azaborine compound SM1-aza. Referring to FIG. 9, an absorption spectra is provided which follows a photoreaction of SM1 for a 5 hour irradiation period. Referring to FIG. 10, fluorescence spectra is shown which follows a photoreaction of SM1 for a 5 hour irradiation period. Referring to FIG. 11, a crystal structure of SM1-aza is shown. Referring to FIG. 12, a crystal structure of DT1 is provided.

The following working examples further illustrate embodiments of the present invention and are not intended to be limiting in any respect.

WORKING EXAMPLES

All experiments were performed under a nitrogen atmosphere unless otherwise noted. Toluene, THF, diethyl ether, hexanes and benzene-$d_6$ were dried using sodium and benzophenone (as an indicator) and were freshly distilled. $CH_2Cl_2$ was distilled over $P_2O_5$. $^1$H, $^{13}$C, $^{11}$B 2D-COSY, 2D-NOESY, 2D-HSQC and 2D-HMBC NMR spectra were recorded on Bruker Avance 500 or 600 MHz spectrometers. Excitation and emission spectra were recorded using a Photon Technologies International QuantaMaster Model 2 spectrometer. HRMS were measured by Micromass/Waters GCT Time of Flight (TOF) mass spectrometer (MS) and Thermo Scientific Orbitrap Velos Pro mass spectrometer. Elemental analyses were performed at an elemental analysis laboratory, University of Montreal, Montreal, Quebec, Canada. UV-Visible spectra were recorded using a Varian Cary 50 UV-visible absorbance spectrophotometer (available from Varian, Inc. of Agilent Technologies, Mississauga, ON, Canada). Cyclic voltammetry experiments were performed using a BAS CV-50W analyzer. The electrochemical cell was a standard three-compartment cell composed of a Pt working electrode, a Pt auxiliary electrode, and an Ag/AgCl reference electrode. CV measurements were carried out at room temperature with ~0.1 M tetrabutylammonium hexafluorophosphate (TBAP) as the supporting electrolyte, with ferrocene/ferrocenium as internal standard (E°=0.55 V). A solvent mixture of $CH_3CN$ and THF was used for CV measurements. Fluorescence quantum efficiencies were measured using $Ir(ppy)_3$ as a standard in toluene (T. Sajoto, et al., *J. Am. Chem. Soc.* 2009, 131, 9813). Photoelimination quantum efficiency was determined using a ferrioxalate as a standard chemical actinometer using previously reported procedures (C. G. Hatchard, et al., *Proc. R. Soc. Lond. A,* 1956, 235, 518).

Example 1. Synthesis and Characterization of Reactants for Photoirradiation

Synthesis of 2-(2-methylphenyl)-pyridine
2-(2-methylphenyl)-pyridine was prepared using $Pd(PPh_3)_4$ (5 mol %) and $K_2CO_3$ (3 equiv) at 80° C. as typical conditions for Suzuki-coupling reactions. After completion, the reaction mixture was purified by column chromatography on silica gel using $CH_2Cl_2$ and hexane as eluent. $^1H$ NMR and $^{13}C$ NMR data for the product agrees with that previously reported for 2-(2-methylphenyl)-pyridine (C. Liu, et al., *Eur. J. Org. Chem.* 2010, 29, 5548).

Synthesis of 2-(2,5-dimethylphenyl)-4-methylpyridine 2,5-Dimethylbenzenboronic acid (1.0 g, 6.6 mmol), 4-methyl-2-Bromopyridine (1.1 g, 6.6 mmol), $Pd(PPh_3)_4$ (0.38 g, 0.33 mmol) and $K_3PO_4$ (4.2 g, 19.8 mmol) were dissolved in degassed THF and water (3:1) mixture (250 mL). The mixture was refluxed under $N_2$ for 18 hours. After removal of the solvent, the residue was extracted with $CH_2Cl_2$ and water. The organic phase was dried over magnesium sulfate and filtered. The filtrate was purified by column chromatography on silica gel to afford 2-(2,5-dimethylphenyl)-4-methylpyridine as a white solid (0.99 g, 75% yield). $^1H$ NMR ($CDCl_3$, 600 MHz): δ 8.53 (d, J=5.0 Hz, 1H), 7.20 (s, 1H), 7.19 (s, 1H), 7.14 (d, J=7.6 Hz, 1H), 7.09 (d, J=7.6 Hz, 1H), 7.05 (d, J=5.0 Hz, 1H), 2.39 (s, 3H), 2.34 (s, 3H), 2.30 (s, 3H).

Synthesis of Precursor Compounds of Scheme 1 and Scheme 2a.

The precursor compounds shown in Scheme 1 were prepared by the general procedure shown in Scheme 3. Representative examples of BN-1, BN-2, BN-3 and BN-4 are also shown in Scheme 3. The starting materials or ligands 2-(2-methylphenyl)-pyridine for BN-1, 2-(2,5-dimethylphenyl)-4-methylpyridine for BN-2 and BN-4, and 2-(2,5-dimethylphenyl)-benzothiazole for BN-3 were prepared using Suzuki-Miyaura coupling methods with $Pd(PPh_3)_4$ as the catalyst and $K_2CO_3$ as the base. Compound BN-1 was synthesized in good yield by the reaction of n-BuLi with 2-(2-methylphenyl)pyridine at −78° C., followed by the addition of $BMes_2F$. The dimethyl analogue BN-2 and the benzothiazolyl B,N-heterocyclic compound BN-3 were obtained using the same procedure in good yields. For BN-4, $BMes_2F$ was replaced by $BMe_2Br$ in the synthesis. The presence of tetramethylethylenediamine (TMEDA) in the lithiation step is necessary to ensure that the lithiation takes place mostly at the methyl site and not at the ortho-H atom of the phenyl ring, which can lead to the formation of the undesired N^C-chelate $BMes_2$ compounds that are analogues of $B(ppy)Mes_2$ (ppy=phenylpyridine) (R. L. Rao, et al., *J. Am. Chem. Soc.* 2008, 130, 12898) with a five-membered B,N-heterocycle as side product. The yield of BN-4 was poor, which may be caused by the reaction of $BMe_2Br$ with TMEDA.

Diboron precursor compounds shown in Scheme 2a with R=Aryl or aliphatic (alkyl) can be obtained by double-lithiation of the appropriate ligands. An example, (BN)2-1, is shown in Scheme 3a.

Synthesis of Precursor Compounds of Scheme 2.

The precursor compounds shown in Scheme 2 were synthesized by the general procedure shown in Scheme 4. Representative examples of the precursor compounds obtained by this procedure are also shown in Scheme 4. For BC-1 and BC-3, the R group can be an aliphatic, aryl, —$(CH_2O)_n$—R' (n=1-24, R'=alkyl), silyl (e.g. $SiR'_3$) groups. Selected examples of the precursor compounds in Scheme 4 have been fully characterized by NMR spectroscopy. The crystal structure of BC-1 (R=Me) has been determined by X-ray diffraction analysis and is shown in FIG. 2. The same procedure can also be used for reactions of $BH_3(L)$ with ligands shown in Scheme 5a to form diboron compounds. An example (BN)2-2 is shown in Scheme 5a.

Synthesis of BN-1 n-BuLi (0.41 mL, 0.66 mmol) was added to a mixture solution of 2-(2-methylphenyl)-pyridine (100 mg, 0.59 mmol) and TMEDA (0.18 mL, 1.18 mmol) in THF (50 mL) at −78° C. After stirring at this temperature for 2 h, $BMes_2F$ (190 mg, 0.71 mmol) was added. The mixture was stirred for another hour at −78° C., then allowed to warm slowly to room temperature and stirred for 16 hrs. After removal of the solvent, the residue was extracted with $CH_2Cl_2$ and water. The hydrophobic phase was dried over magnesium sulfate and filtered. The resultant filtrate was purified by column chromatography on silica gel to afford BN-1 as a white solid (111 mg, 45% yield). $^1H$ NMR ($C_6D_6$, 600 MHz): δ 8.60 (d, J=6.0 Hz, 1H), 7.20 (d, J=7.3 Hz, 1H), 7.09 (d, J=8.1 Hz, 1H), 6.94 (m, 1H), 6.91 (m, 2H), 6.88 (s, 4H), 6.17 (m, 1H), 3.08 (s, 2H), 2.26 (s, 6H), 2.22 (s, 12H); $^{13}C$ NMR ($CD_2Cl_2$, 125 MHz): δ 156.31, 147.73, 147.70, 146.79, 141.70, 141.09, 133.44, 130.77, 130.46, 129.67, 128.39, 126.14, 124.31, 123.56, 123.04, 77.50, 24.61, 20.24; $^{11}B$ NMR ($CD_2Cl_2$, 160 MHz): δ 1.62; HR-EIMS (m/z): [M$^+$] calcd. for $C_{30}H_{32}BN$, 417.2633; found 417.2614. Elemental analysis, calcd: C, 86.33, H, 87.73, N, 3.36; found: C, 86.33, H, 7.78, N, 3.38.

Synthesis of BN-2 n-BuLi (0.35 mL, 0.56 mmol) was added to a mixture solution of 2-(2,5-dimethylphenyl)-4-methylpyridine (100 mg, 0.51 mmol) and TMEDA (0.14 mL, 1.02 mmol) in THF (50 mL) at −78° C. After stirring at this temperature for 2 hrs, $BMes_2F$ (164 mg, 0.61 mmol) was added. The mixture was stirred for 1 hour at −78° C., then allowed to warm slowly to room temperature and was stirred for 16 hrs. After removal of the solvent, the residue was extracted with $CH_2Cl_2$ and water. The hydrophobic phase was dried over magnesium sulfate and filtered. The resultant filtrate was purified by column chromatography on silica gel to afford BN-2 as a white solid (124 mg, 55% yield). $^1H$ NMR ($CD_2Cl_2$, 500 MHz): δ 8.44 (d, J=6.2 Hz, 1H), 7.81 (s, 1H), 7.48 (s, 1H), 7.14 (d, J=6.2 Hz, 1H), 6.97 (d, J=7.6 Hz, 1H), 6.80 (d, J=7.6 Hz, 1H), 6.60 (s, 4H), 2.76 (s, 2H), 2.58 (s, 3H), 2.36 (s, 3H), 2.18 (s, 6H), 1.87 (s, 12H); $^{13}C$ NMR ($CD_2Cl_2$, 125 MHz): δ 155.64, 153.50, 147.57, 147.23, 144.42, 141.75, 133.56, 133.26, 131.42, 130.29, 129.61, 128.52, 126.56, 124.03, 123.79, 77.50, 24.65, 21.25, 20.73, 20.24; $^{11}B$ NMR ($CD_2Cl_2$, 160 MHz): δ 1.15; HR-EIMS (m/z): [M$^r$] calcd. for $C_{32}H_{36}BN$, 445.2946; found 445.2953. Elemental analysis, calcd: C, 86.28, H, 8.15, N, 3.14; found: C, 86.24, H, 8.26, N, 3.15.

Synthesis of BN-3

Starting material 2-(2,5-dimethylphenyl)-benzothiazole was prepared by the reaction of 1-chlorobenzothiazole with 2,5-dimethylphenylboronic acid using Suzuki-Miyaura coupling methods with $Pd(PPh_3)_4$ (5 mol %) as the catalyst and $K_2CO_3$ (3 equiv) as the base in degassed THF and water (3:1) mixture. $^1H$ NMR and $^{13}C$ NMR data agreed with those previously reported for this compound (H. Hachiva, et al. *Org. Lett.* 2009, 11, 1737). n-BuLi (0.57 mL, 0.92 mmol) was added to a mixture solution of 2-(2,5-dimethylphenyl)benzothiazole (200 mg, 0.84 mmol) and TMEDA (0.25 mL, 1.67 mmol) in THF (50 mL) at −78° C. After stirring the mixture at −78° C. for 2 hrs, $BMes_2F$ (268 mg, 1.00 mmol) was added. After being stirred for 1 hr at −78° C., the mixture was allowed to warm up to room temperature and stirred for another 16 hrs. After the removal of the solvent, the residue was washed with water and extracted with $CH_2Cl_2$. After the hydrophobic phase was dried over $MgSO_4$ and filtered, it was purified by column chromatography on silica gel to afford BN-3 as a white solid (285 mg, 70% yield). $^1H$ NMR ($C_6D_6$, 500 MHz): δ 8.17 (d, J=8.2 Hz, 1H), 7.34 (s, 1H), 7.16 (m, 1H), 7.00 (d, J=7.7 Hz, 1H), 6.92 (s, 4H), 6.86 (m, 2H), 6.75 (d, J=7.8 Hz 1H), 3.29 (s, 2H), 2.31 (s, 12H), 2.28 (s, 6H), 1.94 (s, 3H). $^{13}$C NMR (CD$_2$Cl$_2$, 125 MHz): δ 172.31, 149.66, 147.93, 144.67, 141.87, 134.44, 134.25, 133.45, 130.56, 129.88, 129.64, 128.20, 127.25, 126.86, 126.08, 122.00, 121.98, 77.51, 24.65, 20.50, 20.30. $^{11}$B NMR (CD$_2$Cl$_2$, 160 MHz): δ 2.09; HR-EIMS (m/z): [MH$^+$] calcd. for C$_{33}$H$_{34}$BNS, 488.25778; found 488.25654. Elemental analysis, calcd: C, 81.30, H, 7.03, N, 2.87, S, 6.58; found: C, 81.29, H, 7.13, N, 2.87, S, 6.57.
Synthesis of BN-4:

n-BuLi (0.35 mL, 0.56 mmol) was added to a mixture solution of 2-(2,5-dimethylphenyl)-4-methylpyridine (100 mg, 0.51 mmol) and TMEDA (0.14 mL, 1.02 mmol) in THF (50 mL) at −78° C. After stirring at this temperature for 2 hrs, BMe$_2$Br (0.60 mL, 0.61 mmol) was added. The mixture was stirred for 3 hours at −78° C., then allowed to warm slowly to room temperature and stirred for another 16 hrs. After removal of the solvent, the residue was extracted with CH$_2$Cl$_2$ and water. The hydrophobic phase was dried over magnesium sulfate and filtered. The resultant filtrate was purified via column chromatography on silica gel to afford BN-4 as a white solid (12 mg, 10% yield). $^1$H NMR (C$_6$D$_6$, 500 MHz): δ 8.33 (d, J=6.0 Hz, 1H), 7.42 (d, J=7.6 Hz, 1H), 7.29 (s, 1H), 7.14 (d, J=7.6 Hz, 1H), 7.13 (s, 1H), 6.28 (d, J=7.6 Hz, 1H), 2.34 (s, 2H), 2.30 (s, 3H), 1.73 (s, 3H), 0.56 (s, 6H); $^{13}$C NMR (C$_6$D$_6$, 125 MHz): δ 153.06, 150.41, 144.61, 143.04, 133.23, 131.82, 131.06, 130.27, 128.07, 127.18, 123.12, 122.70, 20.92, 20.46; $^{11}$B NMR (C$_6$D$_6$, 160 MHz): δ −2.65. HR-EIMS (m/z): [MH$^+$] calcd. for C$_{16}$H$_{20}$BN, 238.17616; found 238.17557.
Synthesis of (BN)2-1.

n-BuLi (1.6 mL, 2.5 mmol) was added to a mixture solution of 3,3'-Dimethyl-2,2'-bipyridine (184 mg, 1 mmol) and TMEDA (0.57 mL, 4.0 mmol) in THF (250 mL) at −78° C. After stirring at this temperature for 2 hrs, BMes$_2$F (590 mg, 2.2 mmol) was added. The mixture was stirred for 1 hour at −78° C., then allowed to warm slowly to room temperature and stirred for 16 hrs. After removal of the solvent, the residue was extracted with CH$_3$Cl and water. The hydrophobic phase was dried over magnesium sulfate and filtered. The resultant filtrate was purified by column chromatography on silica gel to afford the product as a white solid (136 mg, 20% yield). $^1$H NMR (C$_6$D$_6$, 600 MHz): δ 8.35 (d, 1H), 6.94 (d, 1H), 6.60 (s, 4H), 5.78 (t, 1H), 3.06 (s, 2H), 2.26 (s, 6H), 2.02 (s, 12H) HR-EIMS (m/z): [M+] calcd. for C$_{48}$H$_{54}$B$_2$N$_2$, 680.4489; found 680.4457.
Synthesis of BC-1.

Preparation of 3-methyl-1-(2,5-dimethyl)phenyl-2,3-dihydro-H1-imidazol-2-ylidene.BH$_3$ (BC-1)

BC-1 was prepared according to the Scheme 8a. 0.785 g (2.50 mmol) of 3-methyl-1-(2,5-dimethyl)phenylimidazolium iodide was loaded into a 50 mL Schlenk flask with 30 mL of dry degassed THF. The solution was cooled to 0° C. and 2.5 mL of KOtBu (1.0 M in THF) was added dropwise, and the solution was allowed to stir for 45 minutes then 45 more minutes at room temperature, resulting in the slurry turning orange. The reaction mixture was re-cooled to 0° C. and 2.5 mL of BH$_3$.THF (1.0 M in THF) was then added dropwise, resulting in the slurry turning pale peach. The mixture was stirred for 30 minutes, then allowed to warm to room temperature and stirred for 2 hours further. Volatiles were then removed under vacuum and the resultant residue was extracted in CH$_2$Cl$_2$ and filtered. Slow evaporation of the resultant filtrate resulted in 0.23 g (46%) of pale yellow crystals which was identified as the target compound. $^1$H NMR (400.3 MHz, CDCl$_3$): δ=7.20 (d, $^3$J$_{HH}$=8.0 Hz, 1H, ArH), 7.17 (d, $^3$J$_{HH}$=8.0 Hz, 1H, ArH), 7.00 (br. s, 1H, ArH), 6.96 (d, $^3$J$_{HH}$=8.0 Hz, 1H, NCH=CHN), 6.86 (d, $^3$J$_{HH}$=8.0 Hz, 1H, NCH=CHN), 3.83 (s, 3H, NCH$_3$), 2.53 (s, 3H, ArCH$_3$), 2.05 (s, 3H, ArCH$_3$), 0.83 (1:1:1:1 q, $^2$J$_{HB}$=88.1 Hz, 3H, BH$_3$). $^{13}$C{$^1$H} NMR (100.7 MHz, CDCl$_3$): δ=~174 (NCN located via HMBC), 137.7 (ArC), 136.4 (ArC), 131.9 (ArC), 130.6 (ArC), 130.0 (ArC), 127.7 (ArC), 120.3 (NCH=CHN), 120.1 (NCH=CHN), 36.0 (NCH$_3$), 20.7 (ArCH$_3$), 17.2 (ArCH$_3$). $^{11}$B{$^1$H} NMR (128.4 MHz, CDCl$_3$): δ=−37.1 (q, $^2$J$_{BH}$=84.7 Hz).

Synthesis of 3-butyl-1-(2,5-dimethyl)phenyl-2,3-dihydro-H1-benzimidazol-2-ylidene.BH$_3$ (BC-3-Bu) (see Scheme 8b)

0.450 g (1.33 mmol) of N-2,5-dimethylphenyl-N-butyl-benzimidazolium iodide was loaded into a 50 mL Schlenk flask with 25 mL of dry degassed THF. The resulting solution was cooled to 0° C. and 1.6 mL of KOtBu (1.0 M in THF) was added dropwise. During this addition, a green colour was present which ceased once a full equivalent was added, and a yellow slurry was observed. The mixture was allowed to stir for 45 minutes, then 45 more minutes at room temperature. The reaction mixture was cooled again to 0° C. and 1.6 mL of BH$_3$.THF (1.0 M in THF) was then added dropwise, no visual change occurred. The mixture was stirred for 30 minutes, then allowed to warm to room temperature and stirred for 2 hours further. The volatiles were then removed under vacuum and the residue was extracted in CH$_2$Cl$_2$ and filtered. The remaining residue was purified by column chromatography, eluting with 50:50 CH$_2$Cl$_2$:hexanes. The combined fractions gave 0.276 g (71%) of a clear, colourless oil, identified as the desired compound by NMR spectra. $^1$H NMR (400.3 MHz, CDCl$_3$): δ=7.50 (d, $^3$J$_{HH}$=4.0 Hz, 1H, ArH), 7.38 (t, $^3$J$_{HH}$=4.0 Hz, 1H, ArH), 7.28-7.23 (m, 3H, ArH), 7.06 (s, 1H, ArH), 6.98 (d, $^3$J$_{HH}$=4.0 Hz, 1H, ArH), 4.50 (t, 2H, $^3$J$_{HH}$=8.0 Hz, NCH$_2$), 2.37 (s, 3H, ArCH$_3$), 1.95 (tt, 2H, $^3$J$_{HH}$=8.0 Hz, NCH$_2$CH$_2$), 1.94 (s, 3H, ArCH$_3$), 1.49 (qt, 2H, $^3$J$_{HH}$=8.0 Hz, NCH$_2$CH$_2$CH$_2$), 1.01 (t, 3H, $^3$J$_{HH}$=8.0 Hz, NCH$_2$CH$_2$CH$_2$CH$_3$), 1.00 (1:1:1:1 q, $^2$J$_{HB}$=88.1 Hz, 3H, BH$_3$). $^{13}$C{$^1$H} NMR (100.7 MHz, CDCl$_3$): δ=(NCN not located), 136.8 (ArC), 135.0 (ArC), 133.8 (ArC), 132.8 (ArC), 132.4 (ArC), 130.9 (ArC), 130.4 (ArC), 128.5 (ArC), 123.9 (ArC), 123.9 (ArC), 111.7 (ArC), 110.7 (ArC), 45.8 (NCH$_2$), 31.0 (NCH$_2$CH$_2$), 20.8 (ArCH$_3$), 20.1 (NCH$_2$CH$_2$CH$_2$), 17.0 (ArCH$_3$), 13.8 (NCH$_2$CH$_2$CH$_2$CH$_3$). $^{11}$B{$^1$H} NMR (128.4 MHz, CDCl$_3$): δ=−36.7 (q, $^2$J$_{BH}$=86.9 Hz).
Synthesis of BN-5

BH$_3$—SMe$_2$ (5.9 ml, 11.8 mmol, 2 eq) was added to a solution of 2-(2-methylphenyl)-pyridine (1 g, 5.9 mmol) in 20 mL of toluene. The mixture was stirred overnight. After removal of solvent and excess BH$_3$—SMe$_2$ under vacuum, white solid of pure product was obtained in 99% yield. $^1$H NMR (THF-d8, 600 MHz): δ 8.85 (d, 1H), 8.05 (dd, 1H), 7.59 (dd, 1H), 7.44 (d, 1H), 7.29 (dd, 1H), 7.28 (m, 2H), 7.17 (d, 1H), 2.48 (s, 3H, broad), 2.06 (s, 3H).
Synthesis of BN-7

2-(2,5-dimethylphenyl)-benzothiazole (1.013 g, 4.23 mmol) was dissolved in dry toluene and the mixture was reduced to −78° C. in a dry ice/acetone bath. To the mixture was added (CH$_3$)$_2$S.BH$_3$ in THF (4 mL, 8.0 mmol) dropwise over a period of 30 min. After stirring for 1 hr, the mixture was allowed to warm to room temperature and was stirred for an additional 10 hrs. The solvent was removed under vacuum and the product mixture was washed by dry hexanes (3×5 mL) to afford a colorless solid of BN-7. $^1$H NMR ($C_6D_6$, 500 MHz): δ 8.81 (d, 1H), 7.14 (m, 1H), 6.99 (d, 1H), 6.94 (m, 1H), 6.93 (m, 2H), 6.84 (s, 1H), 2.18 (s, 3H), 2.02 (s, 3H). HRMS: C15H16BNS: Calc: 253.1099; observed: 253.1105.

Synthesis of BN-bpy1 n-BuLi (0.41 mL, 0.66 mmol) was added to a mixture solution of 3-methyl-2,2'-bipyridine (472 mg, 2.77 mmol) and TMEDA (830 μL, 5.54 mmol) in diethyl ether (15 mL) at −78° C. under $N_2$ atmosphere. After stirring at this temperature for 1 h, BMes$_2$F (800 mg, 2.98 mmol) was added. The mixture was stirred for a further one hour at −78° C., then allowed to warm slowly to room temperature and stirred for 18 h. After removal of the solvent, the residue was extracted with ethyl acetate and water. The hydrophobic phase was dried over magnesium sulfate and filtered. The filtrate was purified by column chromatography on silica gel to obtain BN-bpy1 as a white solid (92 mg, 8% yield). $^1$H NMR (CDCl$_3$, 400 MHz): δ 8.62 (d, $^3$J=8.0 Hz, 1H), 8.58 (d, $^3$J=6.0 Hz, 1H), 8.29 (d, $^3$J=4.4 Hz, 1H), 8.09 (t, $^3$J=7.6 Hz, 1H), 7.39 (t, $^3$J=6.4 Hz, 1H), 7.12 (d, $^3$J=7.6 Hz, 1H), 6.95 (dd, $^3$J=7.2 Hz, $^4$J=4.4 Hz, 1H), 6.59 (s, 4H), 2.81 (s, 2H), 2.16 (s, 6H), 1.86 (s, 12H). $^{13}$C NMR (CDCl$_3$, 100 MHz): δ 155.70, 147.71, 147.50, 145.72, 143.26, 141.78, 141.22, 136.68, 133.94, 129.96, 125.48, 124.67, 124.52, 77.55, 24.95, 20.80. $^{11}$B NMR (CDCl$_3$, 128 MHz): δ 1.75. HR-EIMS (m/z): [M$^+$] calcd. for $C_{29}H_{31}BN_2$, 418.2580; found 418.2597.

Synthesis of BN-bpy-Pt1 and Others

Boron and Pt functionalized compounds BN-bpy-Pt1, BN-bpy-Pt2 and BN-bpy-B1 can be obtained by previously established procedures as shown in Scheme 8c (R. L. Rao, et al., *J. Am. Chem. Soc.* 2008, 130, 12898; Z. M. Hudson, et al., *Org. Lett.*, 2012, 14, 1700). Details for BN-bpy-Pt1 are provided below as a representative example.

Synthesis of BN-bpy-Pt1

[PtMe$_2$(SMe$_2$)$_2$] (62 mg, 0.108 mmol) and BN-bpy1 (90 mg, 0.215 mmol) were dissolved in THF (3 mL) under $N_2$ atmosphere. The reaction mixture is allowed to stir 1 h at room temperature, then a solution of p-toluenesulfonic acid (41 mh, 0.215 mmol) in THF (1 mL) was slowly added dropwise. After 0.5 h, a solution of sodium acetylacetonate (52 mg, 0.430 mmol) in methanol (2 mL) was added to the mixture. The reaction was further stirred for 10 h. After removal of the solvent, the resulting mixture was extracted with dichloromethane and water. The hydrophobic phase was dried over magnesium sulfate, filtered, and concentrated. The residue was recrystallized by dichloromethane and n-hexane to obtain BN-bpy-Pt1 complex as yellow solid (125 mg, 0.176 mmol) in 82% yield. $^1$H NMR (CDCl$_3$, 400 MHz): δ 8.71 (d, $^3$J=5.6 Hz, 1H), 8.17-8.15 (m, 2H), 7.53 (d, $^3$J=7.2 Hz, 1H), 7.13 (t, $^3$J=7.6 Hz, 2H), 6.65 (s, 4H), 5.54 (s, 1H), 2.83 (s, 2H), 2.19 (s, 6H), 2.05 (s, 3H), 2.03 (s, 3H), 1.83 (s, 12H); $^{11}$B NMR (CDCl$_3$, 128 MHz): δ 1.40.

Synthesis of IMes-BMes$_2$ Chelate SM1

IMesHCl (0.503 g, 1.47 mmol) was loaded into an oven-dried 100 mL Schlenk flask and placed under a nitrogen atmosphere. Dry degassed THF (50 mL) was added to the flask via cannula and a white slurry formed. The slurry was chilled to −78° C. in a dry ice/acetone bath and 1.00 mL of 1.6M nBuLi in hexane (1.6 mmol) was added drop-wise. This reaction mixture was stirred for 30 minutes in the cold bath followed by 2 hours out of the bath to generate free carbene. The flask was then cooled a second time to −78° C. followed by addition of freshly distilled TMEDA (0.97 mL; 6.47 mmol) and 1.00 mL of 1.6 M nBuLi. The reaction mixture was stirred for 2 hours at −78° C. followed by addition of Mes$_2$BF (0.473 g, 1.76 mmol). The reaction mixture was stirred for 3 hours while at −78° C. before warming to room temperature and stirring overnight. The resulting mixture was quenched with water and extracted with diethyl ether. An organic extract was dried over MgSO$_4$ followed by removal of volatiles in vaccuo. A resulting solid was dissolved in a minimum of diethyl ether and was precipitated by addition of hexane. The solid was collected by vacuum filtration and 0.723 g (89%) of the chelate product SM1 was collected. X-ray quality crystals were grown using a saturated solution of THF layered with hexanes. $^1$H NMR ($C_6D_6$): δ=1.67 (s, 3H, ArCH$_3$), 1.68 (s, 3H, ArCH$_3$), 1.85 (s, 3H, ArCH$_3$), 2.04 (s, 3H, ArCH$_3$), 2.07 (s, 3H, ArCH$_3$), 2.08 (s, 3H, ArCH$_3$), 2.08 (s, 3H, ArCH$_3$), 2.13 (s, 3H, ArCH$_3$), 2.17 (s, 3H, ArCH$_3$), 2.46 (s, 3H, ArCH$_3$), 2.84 (d, 1H, $^3$J$_{HH}$=12.0 Hz, B—CH$_2$), 2.88 (s, 3H, ArCH$_3$), 3.06 (d, 1H, $^3$J$_{HH}$=12.0 Hz, B—CH$_2$), 5.78 (d, 1H, $^3$J$_{HH}$=4.0 Hz, Imidazole-CH), 5.97 (s, 1H, ArH), 6.18 (s, 1H, ArH), 6.48 (s, 1H, ArH), 6.52 (s, 1H, ArH), 6.52 (s, 1H, ArH), 6.62 (d, 1H, $^3$J$_{HH}$=4.0 Hz, Imidazole-CH), 6.72 (s, 1H, ArH), 6.73 (s, 1H, ArH), 6.73 (s, 1H, ArH). $^{11}$B[$^1$H] NMR ($C_6D_6$): δ=−11.2. $^{13}$C {$^1$H} NMR ($C_6D_6$): δ=19.1 (ArCH$_3$), 19.1 (ArCH$_3$), 20.0 (ArCH$_3$), 20.8 (ArCH$_3$), 20.8 (ArCH$_3$), 21.0 (ArCH$_3$), 21.0 (ArCH$_3$), 24.0 (ArCH$_3$), 24.9 (ArCH$_3$), 27.7 (ArCH$_3$), 27.9 (ArCH$_3$), 33.5 (located by HSQC, B—CH$_2$), 120.0 (Imidazole-CH), 121.3 (Imidazole-CH), 125.3 (ArC), 125.7 (ArC), 6 ArCH located under the solvent signal via HSQC, 129.0 (ArCH), 130.3 (ArC), 130.8 (ArCH), 131.5 (ArC), 131.9 (ArC), 133.0 (ArC), 133.1 (ArC), 134.4 (ArC), 135.9 (ArC), 137.0 (ArC), 138.3 (ArC), 138.7 (ArC), 141.3 (ArC), 141.9 (ArC), 143.1 (ArC), 145.4 (ArC), 207.4 (N—C—N). Anal. Calcd. for $C_{39}H_{45}N_2B$: C, 84.77; H, 8.21; N, 5.07.

Synthesis of DT1

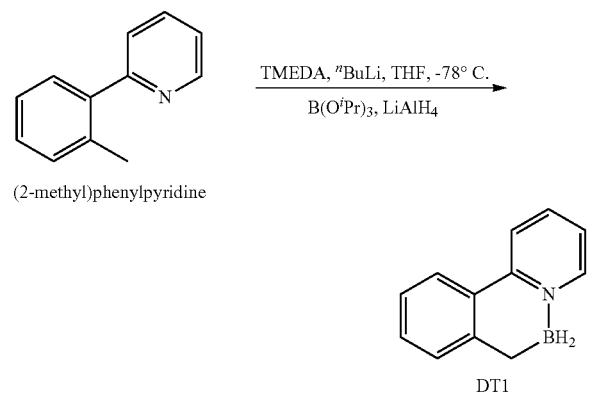

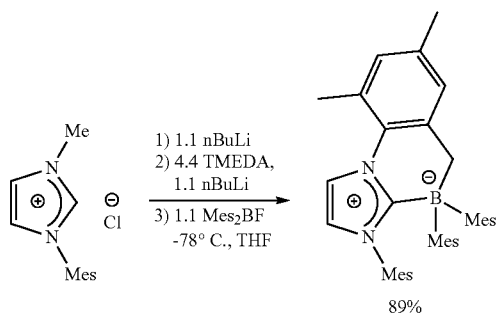

To a stirred solution of (2-methyl)phenylpyridine (200 mg, 1.18 mmol), and TMEDA (0.35 mL, 2.36 mmol) in THF (10 mL) at −78° C., a solution of $^n$BuLi (2.5 M, 0.95 mL, 2.36 mmol) was added dropwise. After 1.5 hours at −78° C., B(O$^i$Pr)$_3$ (0.44 mL, 1.9 mmol) was added dropwise and the solution stirred for 1 hour at this temperature. After this time the mixture was warmed to 0° C. and LiAlH$_4$ (179 mg, 4.72 mmol) added in one portion and the resulting milky mixture stirred for 1 hour at 0° C. and warmed up to room temperature and stirred for overnight. Water was added dropwise to quench the reaction, ether was used to extract the reaction. The organic layers were combined and dried by MgSO$_4$, the solvent was removed in vaccuo and the crude was purified by silica column chromatography, white solid DT1 was obtained (39 mg, 0.21 mmol, 18% yield).

$^1$H NMR (400 MHz, C$_6$D$_6$) δ=8.39 (d, J=5.6 Hz, 1H), 7.45 (d, J=7.8 Hz, 1H), 7.29 (m, 2H), 7.09 (m, 2H), 6.81 (t, J=7.8 Hz, 1H), 6.24 (t, J=5.6 Hz, 1H), 4.24-3.19 (m, 2H), 2.56 (t, J=5.2 Hz, 2H). $^{11}$B NMR (128 MHz, C$_6$D$_6$) δ=−7.53 (J=94.6 Hz).

Example 2. Synthesis of Elimination Products Via Photoelimination

General Procedure for the Generation of Elimination Products (e.g., Azaborine Compounds) by Photoelimination Photolysis was carried out in Norell quartz NMR tube using a Rayonet Photochemical Reactor. Samples were dissolved in freshly distilled C$_6$D$_6$ (0.5 mL) and sealed under N$_2$. The reaction time was dependent on the concentration of the solution. For a sample concentration of about 1.0 mg in 0.5 mL solvent, precursor compounds were converted to elimination products under irradiation for 12 hrs. For a sample concentration at ~1.0×10$^{-5}$ M, full conversion required about 30-40 minutes of UV irradiation, as established by UV-Vis and fluorescence data. After the removal of solvent, mesitylene was isolated from the elimination product by subjecting the residue to vacuum at 90° C. for a few days, or by column chromatograph. Conversion of precursor compounds to their corresponding products was monitored by $^1$H NMR/$^{11}$B NMR spectra. Details of this procedure are illustrated with BN-3a as a representative example.

Representative Example of Solution State Conversion: Photoelimination of BN-3 to Form BN-3a Compound BN-3 was dissolved in freshly distilled C$_6$D$_6$ (0.5 mL) in a Norell quartz NMR tube and sealed under nitrogen. The NMR tube was placed inside a Rayonet Photochemical Reactor (available from Southern New England Ultraviolet Company, Branford, Conn., USA), and irradiated with 350 nm UV lamps. Progression of the elimination reaction was monitored by $^1$H NMR spectroscopy. Photolysis time was dependent on the concentration of the solution. For a sample concentration of about 1.0 mg in 0.5 mL solvent, BN-3 was converted to BN-3a in ~70% yield with ~12 hrs irradiation. For a large preparative scale photolysis, this reaction may be carried out in a quartz flask. The photolysis can also be carried in a sealed quartz cuvette in toluene and monitored by UV-Vis and fluorescence spectroscopy. For a sample concentration of ~1.0×10$^{-5}$ M, full conversion required about 30 minutes. Compound BN-3a can be isolated by first removing the solvent under vacuum at ambient temperature, then heating the residue under vacuum at 90° C. for 3 days to remove mesitylene. Recrystalization from hexane produced bright yellow crystals of BN-3a. $^1$H NMR (500 MHz, C$_6$D$_6$): δ 7.82 (d, J=8.4 Hz, 1H), 7.69 (s, 1H), 7.59 (d, J=8.7 Hz, 1H), 7.26 (s, 1H), 7.20 (d, J=7.9 Hz 1H), 7.12 (s, 2H), 7.04 (m, 2H), 6.89 (m, 1H), 6.81 (m, 1H), 2.43 (s, 3H), 2.34 (s, 6H), 2.26 (s, 3H). $^{13}$C NMR (C$_6$D$_6$, 125 MHz): δ 148.25, 144.73, 144.04, 139.74, 137.08, 132.21, 129.96, 129.06, 128.56, 128.07, 127.88, 127.69, 126.44, 125.78, 124.42, 121.92, 118.78, 117.67, 22.93, 21.26, 21.22. $^{11}$B NMR (C$_6$D$_6$, 160 MHz): δ 35.4; HR-EIMS (m/z): [M$^+$] calcd. for C$_{24}$H$_{22}$BNS, 367.1577; found 367.1570. See Table 3 for photophysical properties of BN-3a.

Representative Example of Solid State Conversion: Photoelimination of BN-3 to Form BN-3a in a PMMA Film PMMA (Poly(methyl methacrylate)) was purified by dissolving it in THF, followed by suspending it in water, then filtering and drying the polymer under vacuum for 3 days. About 10 mg of the purified PMMA powder and 1 mg of BN-3 were mixed and dissolved in 2 mL of dry THF in a glove box under a nitrogen atmosphere. This solution was used to cast a thin film on either a quartz glass slide or one side of a quartz cuvette. After the film was dried, it was subjected to UV irradiation by either a hand-held UV lamp at 365 nm or a UV reactor at 350 nm. To record the UV-Vis spectra, the cuvette was sealed under nitrogen. The formation of BN-3a was observed after a few minutes of exposure to UV light and the full conversion was achieved after about 1.0 hr exposure, based on UV-Vis spectra.

The above solution state and solid state procedures can be used for other precursor compounds such as BN-1, BN-2, BN-4 etc.

Characterization Data for Azaborine Compounds

BN-1a $^1$H NMR (C$_6$D$_6$, 600 MHz): δ 8.39 (d, J=7.0 Hz, 1H), 8.21 (d, J=8.8 Hz, 1H), 8.15 (d, J=9.0 Hz, 1H), 7.80 (d, J=8.4 Hz, 1H), 7.39 (m, 1H), 7.36 (s, 1H), 7.12 (d, J=8.4 Hz, 1H), 7.11 (s, 2H), 6.81 (m, 1H), 6.28 (m, 1H), 2.42 (s, 3H), 2.30 (s, 6H); $^{13}$C NMR (C$_6$D$_6$, 125 MHz): δ 145.33, 142.48, 140.53, 137.35, 136.93, 136.46, 128.82, 128.72, 128.26, 127.10, 124.71, 121.78, 119.86, 118.99, 115.91, 22.56, 21.05; $^{11}$B NMR (C$_6$D$_6$, 160 MHz): δ 35.52; HR-EIMS (m/z): [M$^+$] calcd. C$_{21}$H$_{20}$BN, for 297.1693; found 297.1695. See Table 3 for photophysical properties of BN-1a.

BN-2a $^1$H NMR (C$_6$D$_6$, 600 MHz): δ 8.38 (d, J=7.0 Hz, 1H), 8.16 (s, 1H), 8.15 (s, 1H), 7.80 (d, J=8.5 Hz, 1H), 7.34 (s, 1H), 7.27 (d, J=8.5 Hz, 1H), 7.13 (s, 2H), 6.20 (d, J=7.0 Hz, 1H), 2.45 (s, 3H), 2.43 (s, 3H), 2.37 (s, 6H) 1.93 (s, 3H); $^{13}$C NMR (C$_6$D$_6$, 125 MHz): δ 144.17, 142.15, 140.60, 139.12, 137.35, 136.79, 136.19, 131.24, 128.86, 128.24, 127.10, 123.41, 120.81, 118.42, 118.15, 116.86, 22.66, 21.68, 21.20, 20.88; $^{11}$B NMR (C$_6$D$_6$, 160 MHz): δ 34.97. HR-EIMS (m/z): [M$^+$] calcd. for C$_{23}$H$_{24}$BN, 325.2006; found 325.1997. See Table 3 for photophysical properties of BN-2a.

BN-4a $^1$H NMR (C$_6$D$_6$, 500 MHz): δ 8.18 (d, J=7.0 Hz, 1H), 8.13 (s, 2H), 7.82 (d, J=8.5 Hz, 1H), 7.33 (s, 1H), 7.26 (d, J=8.5 Hz, 1H), 6.33 (d, J=7.0 Hz, 1H), 2.45 (s, 3H), 2.00 (s, 3H), 1.35 (s, 3H); $^{13}$C NMR (C$_6$D$_6$, 125 MHz): δ 143.98, 143.41, 141.58, 135.05, 131.18, 128.99, 128.49, 123.40, 120.68, 117.66, 116.0, 29.97, 22.79, 21.71; $^{11}$B NMR (C$_6$D$_6$, 160 MHz): δ 35.03; HR-ESIMS (m/z): [MH$^+$] calcd. for C$_{15}$H$_{16}$BN, 222.14486; found 222.14420. See Table 3 for photophysical properties of BN-4a.

(BN)2-1a

This compound was obtained in the same manner as that of BN-1a. It was an insoluable solid and was characterized by HRMS. Calculated Mass for intermediate (one side reacted) (C$_{39}$H$_{42}$B$_2$N$_2$): 560.3547; Observed: 560.3352. Calculated Mass for (BN)2-1a the product (C$_{30}$H$_{30}$B$_2$N$_2$): 440.2606; observed: 440.2611.

BN-bpy-Pt1a and BN-bpy-B1 can be obtained by the same procedure as that used for BN-1a. (See FIG. 3E for the conversion of BN-bpy-Pt1 to BN-bpy-Pt1a, monitored by UV-Vis and phosphorescent spectra)

BN-5b 10 mg of BN-5 was dissolved in 0.5 mL of THF-$d_8$ in a quartz NMR tube and sealed under $N_2$. This tube was placed in the UV-chamber (300 nm) for 8 hours. White precipitate was observed and the clear solution was characterized by HRMS (EI) showing the formation of the trimer product. HR-ESIMS (m/z): $C_{36}H_{24}B_3N_3$, Calculated 531.2267; observed 531.2231. In addition, the patterns for both closely match one another.

Procedure for Photoelimination of BC-1 to its Trimer BC-1b

This procedure was done according to the Scheme 8a. BC-1 was loaded into a quartz NMR tube inside a glove box and dissolved in dry degassed $C_6D_6$. The NMR tube was brought out into the open environment with the cap tightly fastened and wrapped in many layers of PARAFILM™. The NMR tube was suspended in a UV reactor and 300 nm light irradiated the sample. The reaction was monitored by NMR over 2 weeks. The chemical shift of $H_2$ at 4.47 ppm was observed and the intensity of BC-1 peaks decreased gradually with irradiation time. Inside the NMR tube a colorless precipitate began to accumulate which was believed to be the trimer BC-1b.

Synthesis of Azaborine SM1-aza

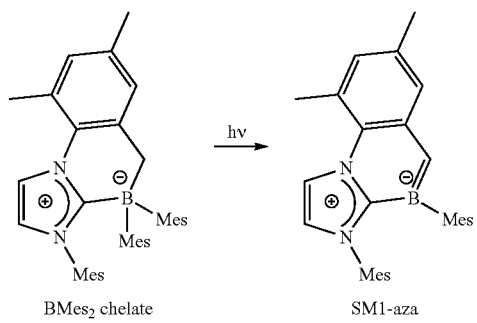

BMes$_2$ chelate (25 mg) was loaded into a quartz NMR tube in a nitrogen atmosphere glove box. Distilled $C_6D_6$ (0.7 mL) was added and the tube was capped and sealed with Teflon tape and Parafilm®. The tube was exposed to 300 nm UV light for 3 days with brief interruptions to monitor the NMR spectra. Once the starting material was present in equal amount to the product, by peak integration, the tube was reintroduced to the glovebox and the solution was allowed to slowly evaporate for about 24 hrs. A resulting residue was washed with a small amount of toluene and decanted to separate it from the remaining crystalline solid. 12 mg (48%) of the crystalline solid remained and was found to be the pure SM1-aza azaborine product. Single crystals were grown from a concentrated solution of THF which was allowed to evaporate slowly to half volume then chilled to −35° C. Synthesis of SM1-aza may also be performed on a large scale using freshly distilled THF as the solvent in a sealed flask Yields were near 50%, in line with expectations. The new azaborine compound SM1-aza was determined to be a blue fluorescent emitter with emission quantum efficiency=0.60.

$^1$H NMR ($C_6D_6$): δ=1.77 (s, 6H, ArCH$_3$), 2.04 (s, 3H, ArCH$_3$), 2.26 (s, 3H, ArCH$_3$), 2.30 (s, 6H, ArCH$_3$), 2.31 (s, 3H, ArCH$_3$), 2.54 (s, 3H, ArCH$_3$), 6.22 (d, 1H, $^3J_{HH}$=4.0 Hz, Imidazole-CH), 6.43 (s, 2H, ArH), 6.66 (s, 2H, ArH), 6.71 (s, 1H, ArH), 7.46 (s, 1H, B—CH), 7.60 (s, 1H, ArH), 8.04 (d, 1H, $^3J_{HH}$=4.0 Hz, Imidazole-CH). $^{11}$B [$^1$H] NMR ($C_6D_6$): δ=28.3.

Synthesis of DT1-aza

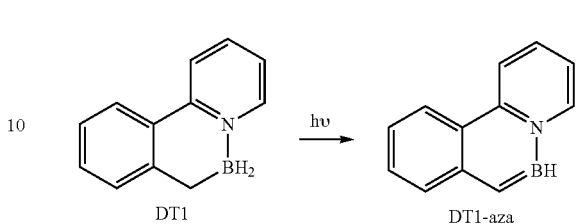

Photolysis was carried out in quartz J-Young NMR tube using a Rayonet Photochemical Reactor. Samples were dissolved in freshly distilled $C_6D_6$ (0.5 mL) and sealed under $N_2$. The reaction time was dependent on the concentration of the solution. For a sample concentration of about 1.0 mg in 0.5 mL solvent, the precursor compound DT1 can be converted to the corresponding azaborine compound DT1-aza under irradiation for 24 hours.

$^1$H NMR (400 MHz, $C_6D_6$) δ=8.29 (d, J=6.7 Hz, 1H), 8.18 (d, J=8.7 Hz, 1H), 8.04 (d, J=8.6 Hz, 1H), 7.87 (d, J=8.5 Hz, 1H), 7.65 (s, 1H), 7.42 (t, J=8.2 Hz, 1H), 7.16 (m, 1H), 6.86-6.77 (m, 2H), 6.37-6.28 (m, 2H). $^{11}$B NMR δ=(128 MHz, $C_6D_6$) δ 32.31 (J=138.8 Hz).

Example 3. Fabrication on EL Device

An OLED device was fabricated in a glove box under an inert atmosphere. 100 μL of 1,2-dicholorobenzene solution of 3 wt % of PVK with 5 wt % BN-3 as the dopant was placed onto freshly-treated ITO glass (UV and Ozone for 10 min) and spin-cast at 2,000 rpm for 2 min, 4,000 rpm for 1 min, and 9,000 rpm for 2 min. Films were dried at 50° C. for at least 2 h before UV-irradiation was applied. The thickness of the films was less than 100 nm. The films were then irradiated by UV light at 265 or 350 nm to convert the BN-3 dopant to BN-3a. A layer of Calcium metal (200 nm) was thermally evaporated as electrode under vacuum (<2.0× 10−6 torr). A Keithley 237 source measurement unit, a Keithley 2010 multimeter, and a Hamamatsu amplified photodiode were used to drive the devices and to measure the current-voltage-light intensity characteristics of the devices. The EL spectra of the devices are recorded by using an Ocean optics HR2000 high-resolution spectrometer. See FIG. 6E for a photo of electroluminescence from such a electroluminescent device.

Example 4. Synthesis of Elimination Products Via Thermoelimination

General Procedure for the Generation of Elimination Products (e.g., Azaborine Compounds) by Thermoelimination Pyrolysis was carried out in a sealed flask or a sealed Wilmad-lab Glass pressure/vacuum NMR tube. Solid samples of precursor compounds were placed inside the flask or the NMR tube and sealed under vacuum. An oil bath or a sand bath was placed on top of a hot plate and heated to the desired temperature as monitored by a thermometer. The flask or tube containing the precursor compound was then placed in either the oil bath or the sand bath. Conversion of the precursor compound to azaborine via heating to induce a thermoelimination reaction was monitored by appearance of bright fluorescence, which is characteristic of the azaborine compound. The reaction time required was dependent on the amount of sample used. After the reaction was completed, the product was isolated by crystallization from either toluene or THF and characterized by $^1H/^{11}B$ NMR spectra. Details of this general procedure are illustrated with BN-1a as a representative example.

In a NMR tube was placed ~10 mg of non-fluorescent precursor compound BN-1. The NMR tube was then evacuated under vacuum and the valve of the NMR tube was closed. An oil bath was heated to 230° C. on top of a Corning hot plate. After the temperature of the oil bath was stabilized, the NMR tube was placed in the oil bath and maintained for ~10 minutes. Bright green fluorescence was observed from the reaction mixture. After the tube and contents were cooled to ambient temperature, a fluorescent solid was observed. A sample of this product of pyrolysis was dissolved in $C_6D_6$ and $^1H$ and $^{11}B$ NMR spectra were recorded. The spectra confirmed the presence of azaborine product BN-1a. In addition, the NMR spectra showed evidence of a second azaborine product that was larger (higher molecular weight) than BN-1a. Although not wishing to be bound by theory, the inventors suggest that the second azaborine may be a dimer or trimer of BN-1a.

High resolution mass spectra (electron-spray ionization, ESI mode) for a sample of the pyrolysis mixture were recorded on an AB Sciex Qsar XL ESI Quadrupole Time of Flight Mass Spectrometer. Calculated {[BN-1a]+1} ion, 297.1765; observed: 298.1758. Other high MS peaks were observed: 418.2813, 440.2717 and 536.6386.

It will be understood by those skilled in the art that this description is made with reference to certain preferred embodiments and that it is possible to make other embodiments employing the principles of the invention which fall within its spirit and scope as defined by the claims.

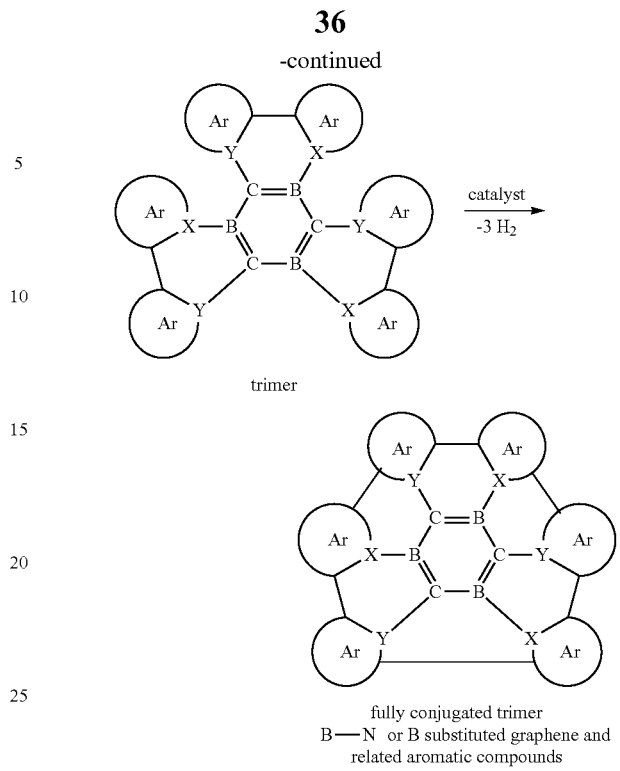

Formation of an organoboron trimer via photolysis and formation of a fully conjugated trimer (B—N or B substituted graphene and related aromatic molecules) via oxidative dehydrogenation process.

Schemes

Scheme 1.

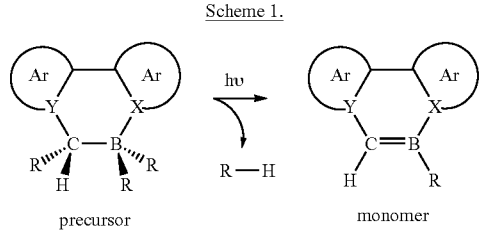

Photoelimination of a generic precursor to form a monomer (or a monoboron compound).

Scheme 2.

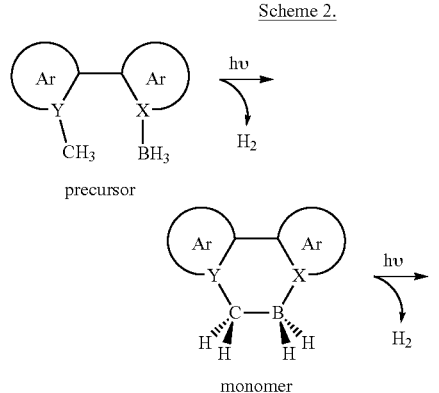

Scheme 2a.

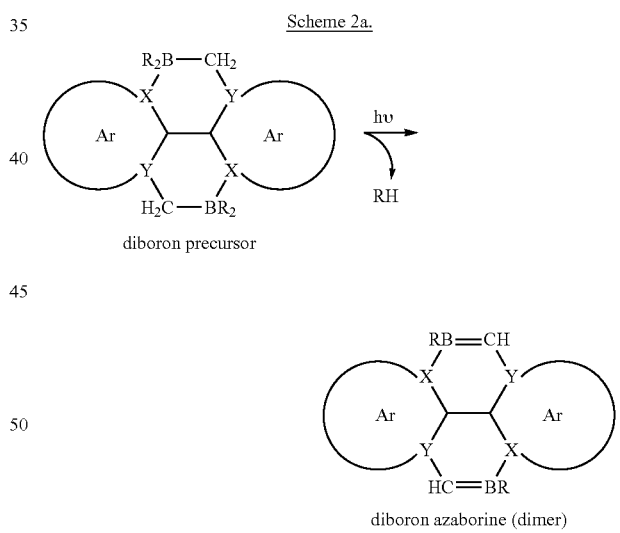

Showing the diboron precursor compounds and their photoelimination to form the diboron azaborine compounds.

Scheme 3

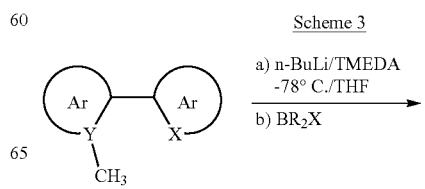

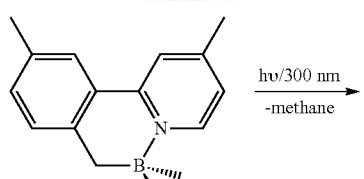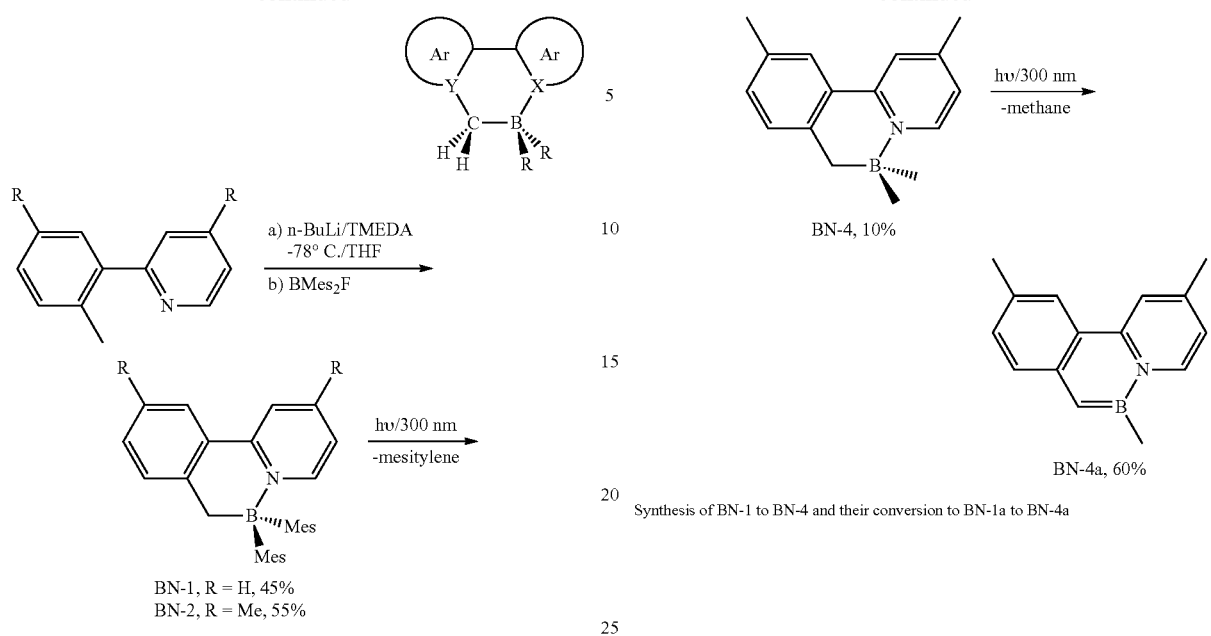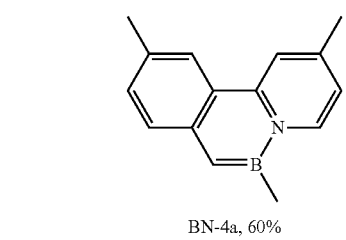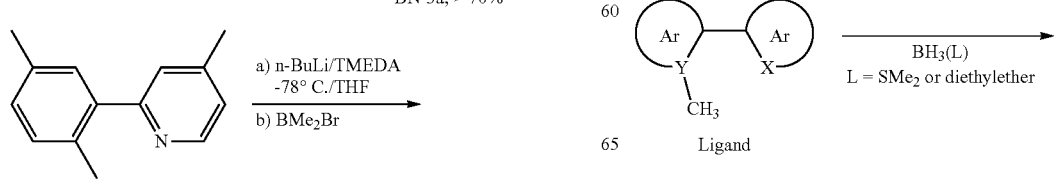

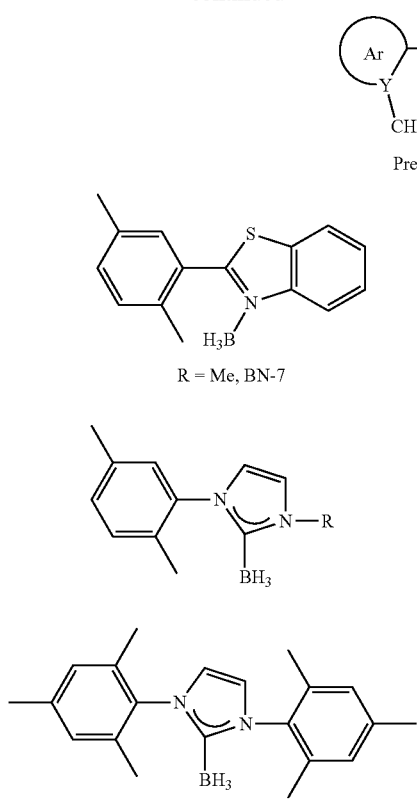
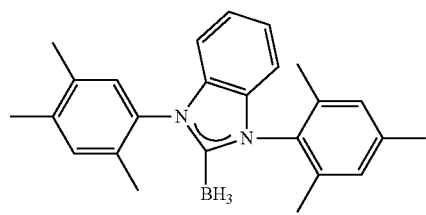
The synthetic procedure for BH₃-precursor compounds of Scheme 2.
Scheme 5.
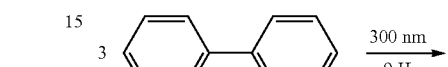
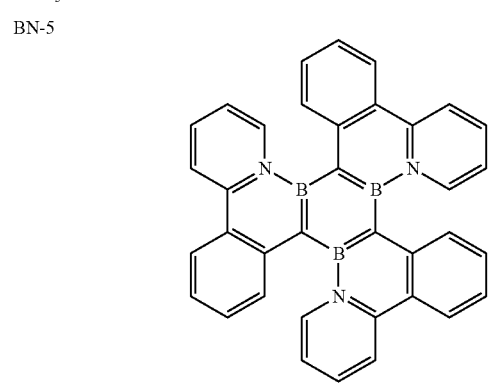
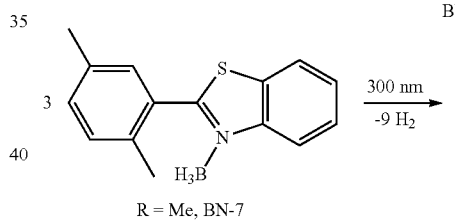
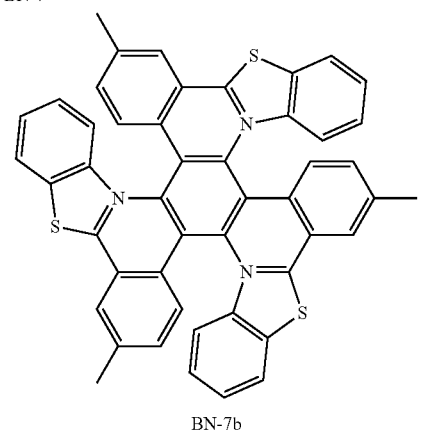
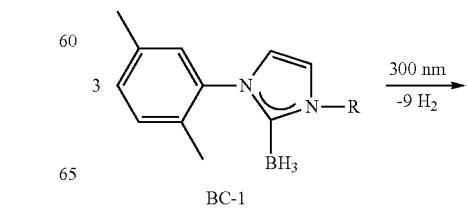

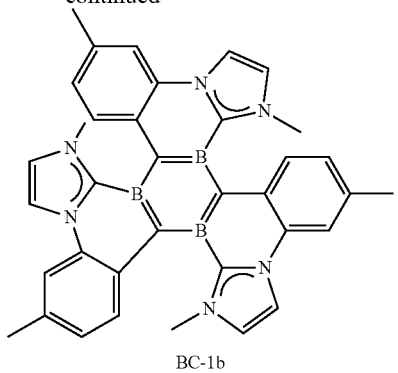

BC-1b

Structures of selected precursors and corresponding trimers.

Scheme 5a.

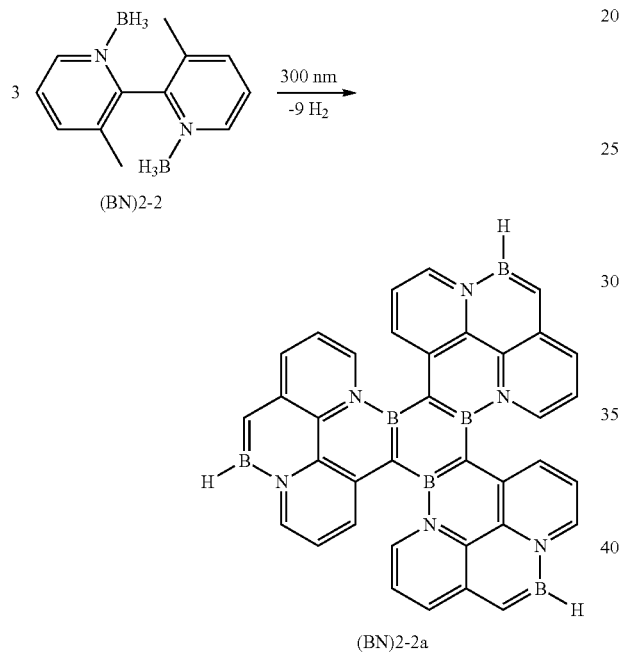

(BN)2-2

(BN)2-2a

Formation of (BN)2-2a from the photoelimination of (BN)2-2. Notably (BN)2-2a can further photoeliminate hydrogen molecules on the periphery of the molecule, leading to the formation of larger conjugated molecules.

Scheme 6.

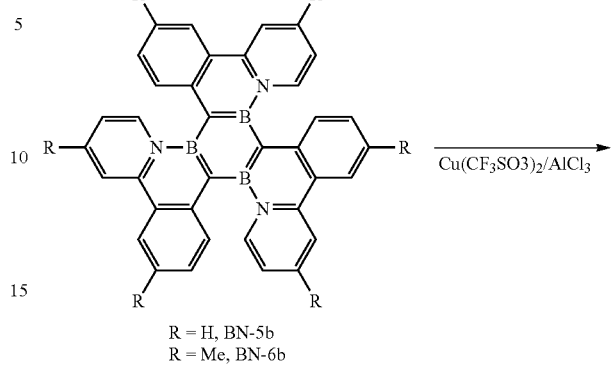

R = H, BN-5b
R = Me, BN-6b

R = H, BN-5c
R = Me, BN-6c

Conversion of the trimers BN-5b and BN-6b to the fully conjugated molecules BN-5c and BN-6c.

Scheme 7a.

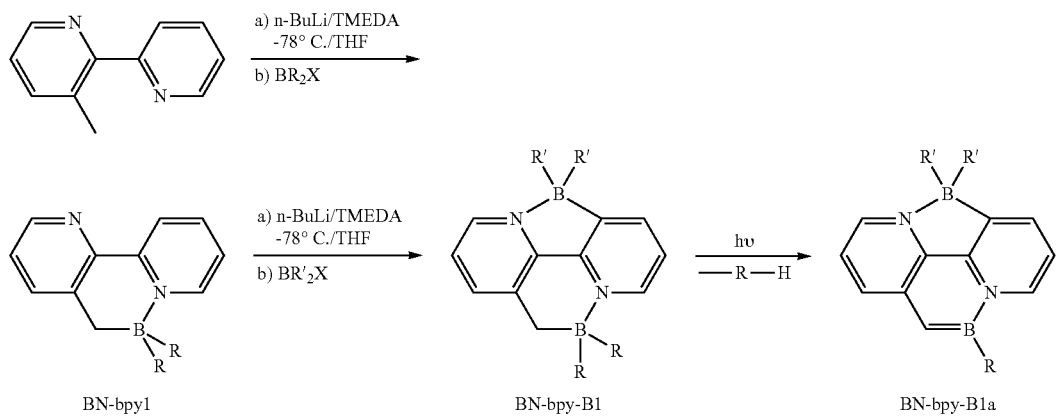

BN-bpy1     BN-bpy-B1     BN-bpy-B1a

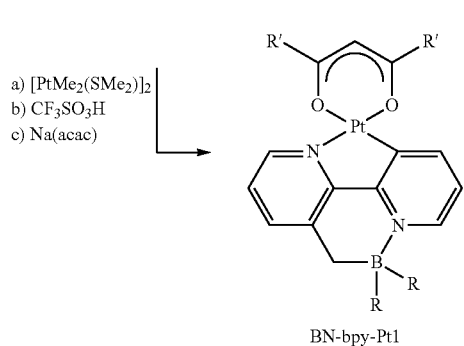
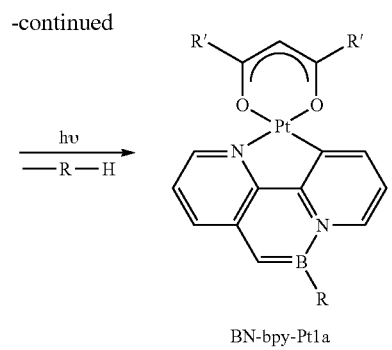
BN-bpy-Pt1    BN-bpy-Pt1a
R, R' = alkyl, aryl
Synthetic procedures of BN-bpy1, BN-bpy-B1, BN-bpy-B1a, BN-bpy-Pt1 and BN-bpy-Pt1a.
Scheme 7b.
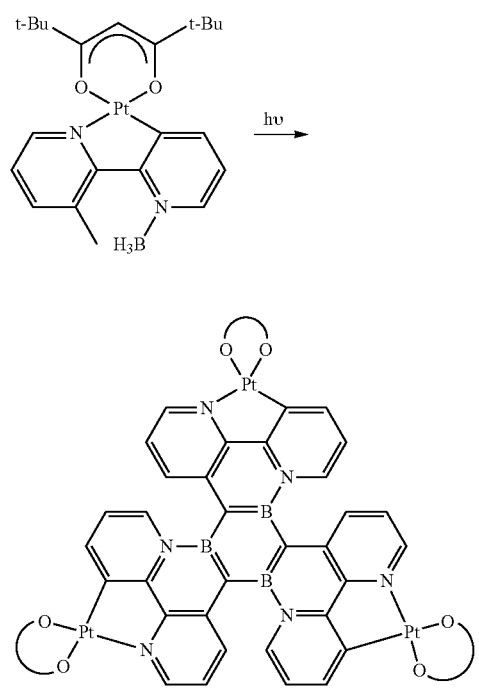
Synthetic procedure for the formation of BN-bpy-Pt1a trimer and the fully conjugated trimer.
Scheme 8a.
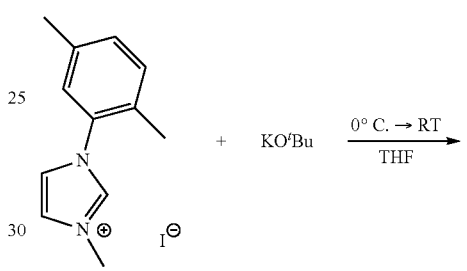
Synthetic procedure for BC-1.
Scheme 8b.
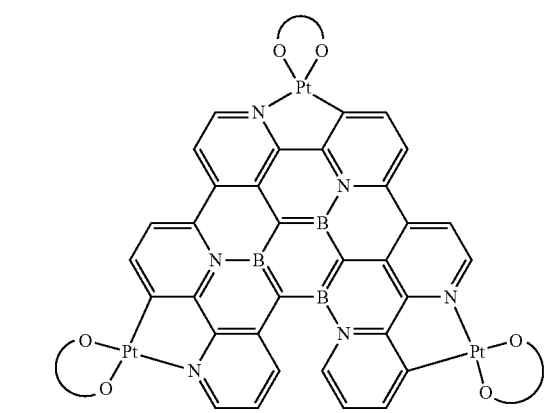

45
-continued
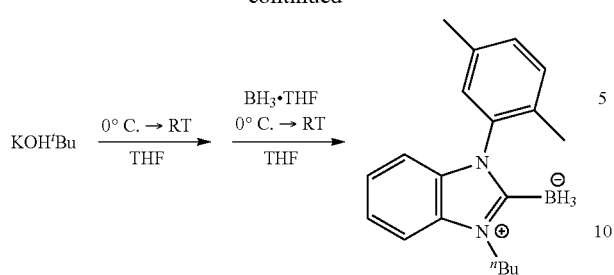
Synthetic procedure for BC-3-Bu.
46
-continued
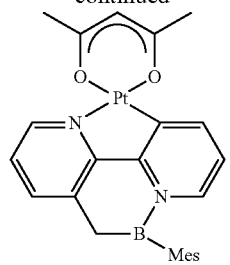
BN-bpy-Pt1
The synthetic procedure for BN-bpy1, BN-bpy-Pt1 and BN-bpy-Pt1a.
Scheme 8c.
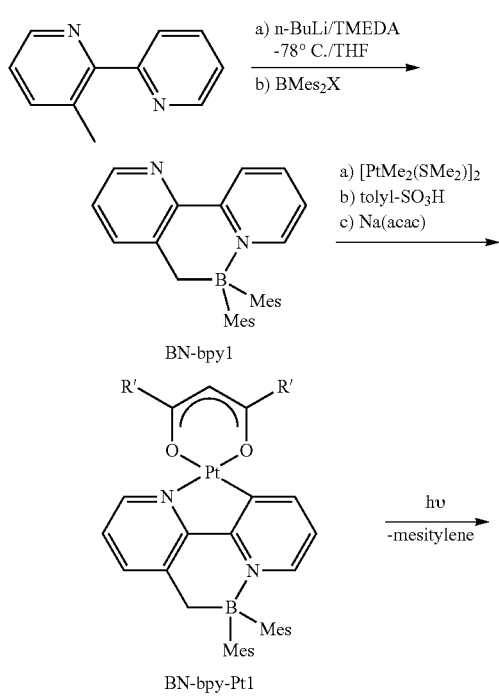
Scheme 8d.
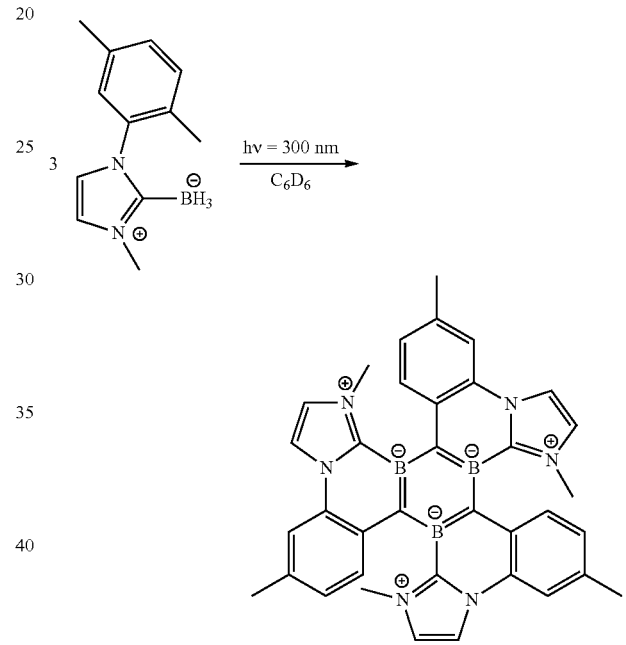
Synthetic procedure for the trimer of BC-1.

TABLE 1
Structural formulae of starting materials and photoelimination products.
| Ligand | Precursor | Elimination Product | Terms |
|---|---|---|---|
| 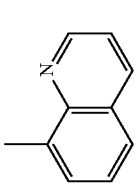 | 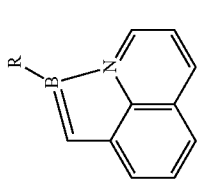 | 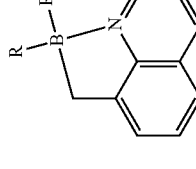 | R = aryl, alkyl, H |
| 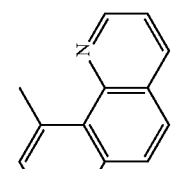 | 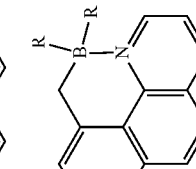 | 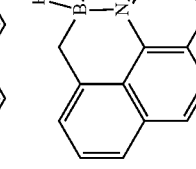 | R = aryl, alkyl, H |
| 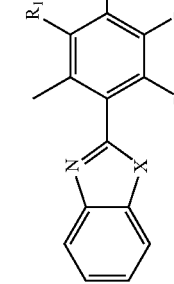 | 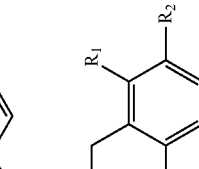 | 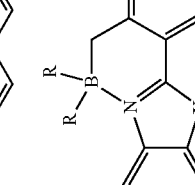 | $R$ = aryl, alkyl, H<br>$R_1$ = aryl, alkyl, H<br>$R_2$ = aryl, alkyl, H<br>$R_3$ = aryl, alkyl, H<br>$R_4$ = aryl, alkyl, H<br>X = O, S, N—R |
| 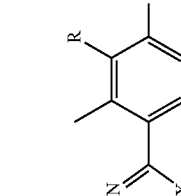 |  | 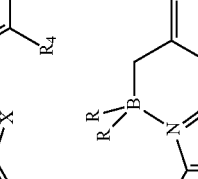 | R = aryl, alkyl, H<br>X = O, S, N—R |

TABLE 1-continued

Structural formulae of starting materials and photoelimination products.

| Ligand | Precursor | Elimination Product | Terms |
|---|---|---|---|
| (structure) | (structure) | (structure) | $R_1$ = aryl, alkyl, H $R_2$ = aryl, alkyl, H |

TABLE 1-continued
Structural formulae of starting materials and photoelimination products.
| Ligand | Precursor | Elimination Product | Terms |
|---|---|---|---|
| 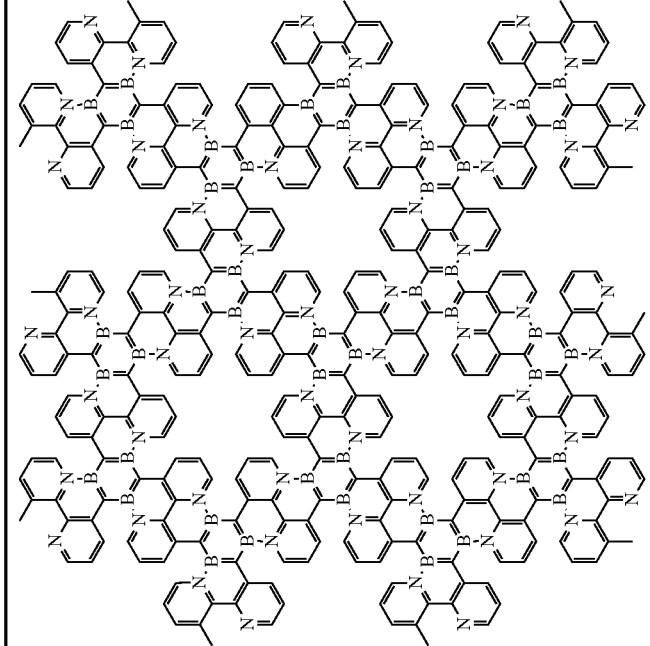 | 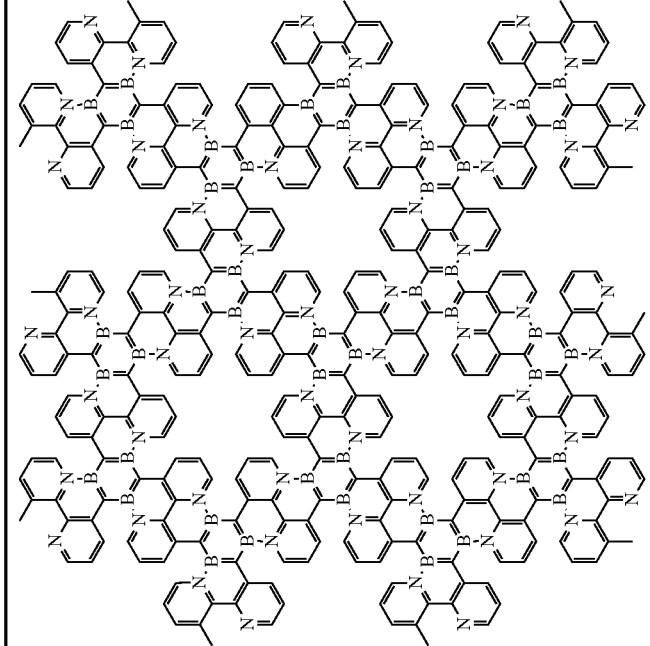 | 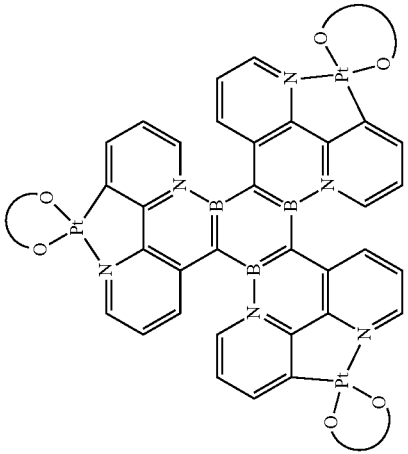 | |

TABLE 1-continued

Structural formulae of starting materials and photoelimination products.

| Ligand | Precursor | Elimination Product | Terms |
|---|---|---|---|
| | | | R = aryl, alkyl, H |
| | | | R' = aryl, alkyl<br>R = Aryl, alkyl, H |
| | | | R' = aryl, alkyl<br>R = Aryl, alkyl, H |
| | BN-1, R = H<br>BN-2, R = Me | BN-1a, R = H<br>BN-2a, R = Me | |

TABLE 1-continued
Structural formulae of starting materials and photoelimination products.
| Ligand | Precursor | Elimination Product | Terms |
|---|---|---|---|
| 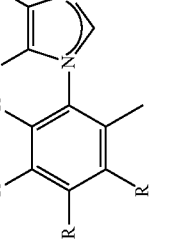 | 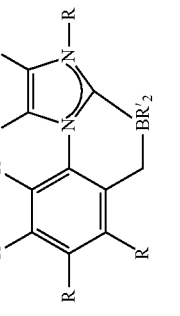 | 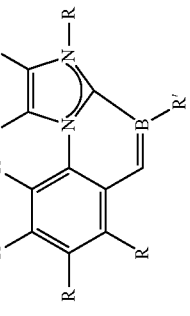 | R' = aryl, alkyl<br>R = Aryl, alkyl, H |
| 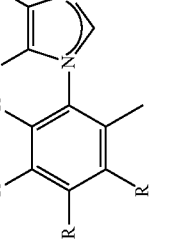 | 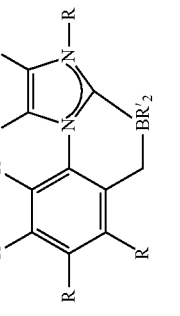 | 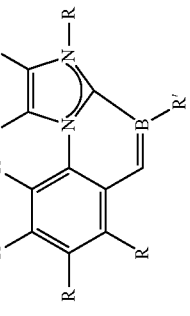 | R' = aryl, alkyl<br>R = Aryl, alkyl, H |
| 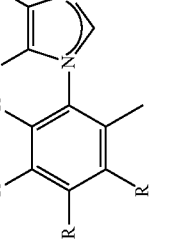 | 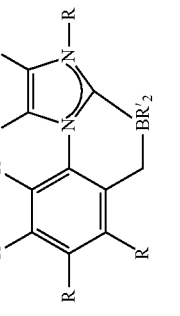 | 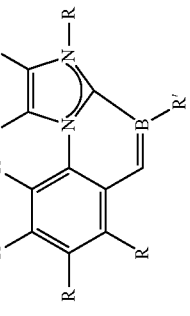 | R = aryl, alkyl, H |

TABLE 1-continued

Structural formulae of starting materials and photoelimination products.

| Ligand | Precursor | Elimination Product | Terms |
|---|---|---|---|
| | | | R = aryl, alkyl, H |
| | | | R = aryl, alkyl, H |

TABLE 1-continued

Structural formulae of starting materials and photoelimination products.

| Ligand | Precursor | Elimination Product | Terms |
|---|---|---|---|
| | | | R = aryl, alkyl, H |
| | | | R = aryl, alkyl, H |
| | | | $R_1$ = aryl, alkyl, H<br>$R_2$ = aryl, alkyl, H<br>$R_3$ = aryl, alkyl, H<br>$R_4$ = aryl, alkyl, H<br>X = O, S, N—R |

TABLE 1-continued
Structural formulae of starting materials and photoelimination products.
| Ligand | Precursor | Elimination Product | Terms |
|---|---|---|---|
| 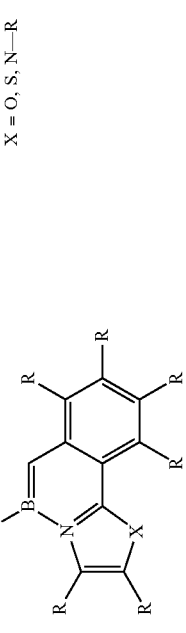 | 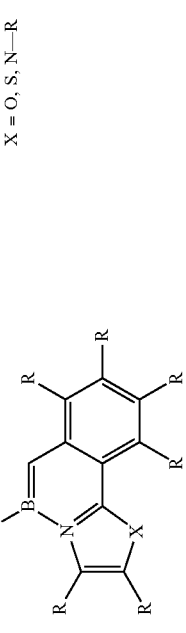 | 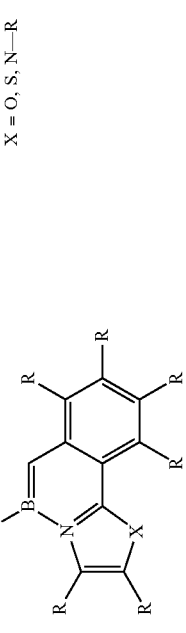 | R = aryl, alkyl, H<br>X = O, S, N—R |
| 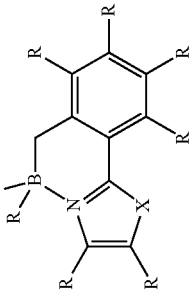 | 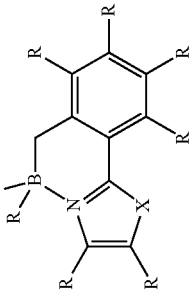 | 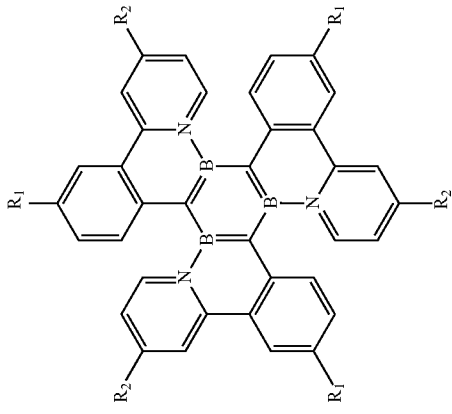 | $R_1$ = aryl, alkyl, H<br>$R_2$ = aryl, alkyl, H |

TABLE 1-continued

Structural formulae of starting materials and photoelimination products.

| Ligand | Precursor | Elimination Product | Terms |
|---|---|---|---|
| | | | R = aryl, alkyl, H |
| | | | R$_1$ = aryl, alkyl, H<br>R$_2$ = aryl, alkyl, H<br>R$_3$ = aryl, alkyl, H<br>R$_4$ = aryl, alkyl, H<br>R$_5$ = aryl, alkyl, H<br>R$_6$ = aryl, alkyl, H<br>R$_7$ = aryl, alkyl, H<br>R$_8$ = aryl, alkyl, H |

TABLE 1-continued
Structural formulae of starting materials and photoelimination products.
| Ligand | Precursor | Elimination Product | Terms |
|---|---|---|---|
| 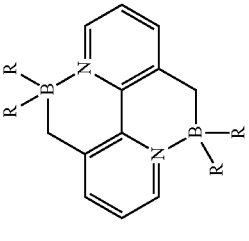 | 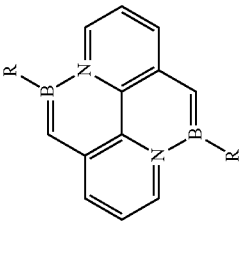 | 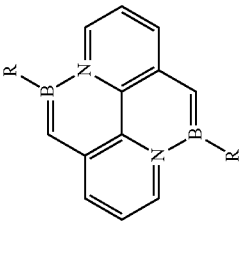 | R = aryl, alkyl, H |
| 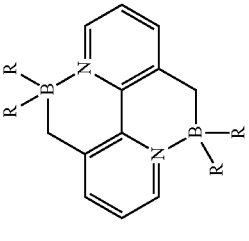 | 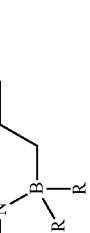 | 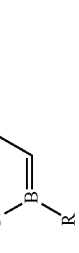 | R = aryl, alkyl, H |
| | | | R = aryl, alkyl, H |

TABLE 1-continued

Structural formulae of starting materials and photoelimination products.

| Ligand | Precursor | Elimination Product | Terms |
|---|---|---|---|
| (structure) | (structure) | (structure) | R = aryl, alkyl, H<br>$R_1$ = aryl, alkyl, H<br>$R_2$ = aryl, alkyl, H<br>$R_3$ = aryl, alkyl, H<br>$R_4$ = aryl, alkyl, H<br>$R_5$ = aryl, alkyl, H<br>$R_6$ = aryl, alkyl, H |
| (structure) | (structure) | (structure) | R = aryl, alkyl, H<br>$R_1$ = aryl, alkyl, H<br>$R_2$ = aryl, alkyl, H<br>$R_3$ = aryl, alkyl, H<br>$R_4$ = aryl, alkyl, H<br>$R_5$ = aryl, alkyl, H<br>$R_6$ = aryl, alkyl, H<br>$R_7$ = aryl, alkyl, H<br>$R_8$ = aryl, alkyl, H<br>$R_9$ = aryl, alkyl, H<br>$R_{10}$ = aryl, alkyl, H |
| (structure) | (structure) | (structure) | R = aryl, alkyl, H<br>$R_1$ = aryl, alkyl, H<br>$R_2$ = aryl, alkyl, H<br>$R_3$ = aryl, alkyl, H<br>$R_4$ = aryl, alkyl, H<br>$R_5$ = aryl, alkyl, H<br>$R_6$ = aryl, alkyl, H |

TABLE 1-continued

Structural formulae of starting materials and photoelimination products.

| Ligand | Precursor | Elimination Product | Terms |
|---|---|---|---|
| | | | R = aryl, alkyl, H<br>n ≥ 0 |
| | | R = H, the trimer can further form polymers. | R = aryl, alkyl, H<br>n ≥ 0 |
| | | R = H, the trimer can further form polymers. | R = aryl, alkyl, H |

TABLE 1-continued

Structural formulae of starting materials and photoelimination products.

| Ligand | Precursor | Elimination Product | Terms |
|---|---|---|---|
| (triaryl triazine) | (boron precursor, R groups) | (boron elimination product, R groups); R = H, the trimer can further form polymers. | R = aryl, alkyl, H |
| imidazolium chloride (Mes) | SM1 | SM1-aza | |
| 2-(o-tolyl)pyridine | SM1 (BH₂) | DT1-aza | |

TABLE 1-continued

Structural formulae of starting materials and photoelimination products.

| Ligand | Precursor | Elimination Product | Terms |
|---|---|---|---|
| | BN-3 | BN-3a | |
| | BN-4 | BN-4a | |
| | (BN)2-1 | (BN)2-1a | |

TABLE 1-continued
Structural formulae of starting materials and photoelimination products.
| Ligand | Precursor | Elimination Product | Terms |
|---|---|---|---|
|  | 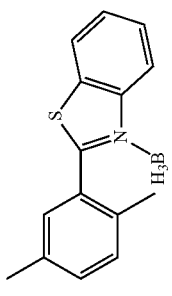 BN-5 | 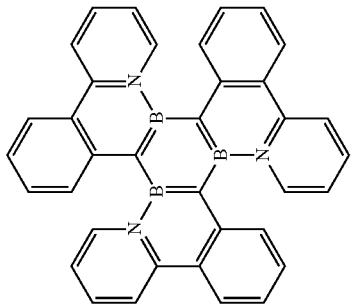 BN-5b |  |
|  |  R = Me, BN-7 | 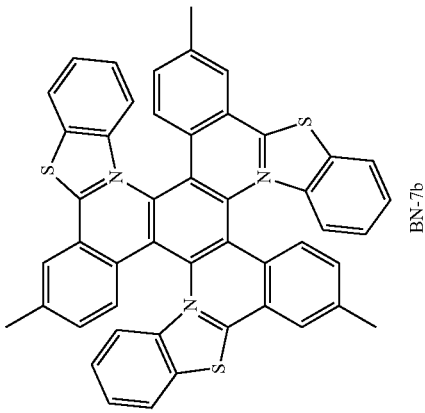 BN-7b |  |

TABLE 1-continued
Structural formulae of starting materials and photoelimination products.
| Ligand | Precursor | Elimination Product | Terms |
|---|---|---|---|
| | 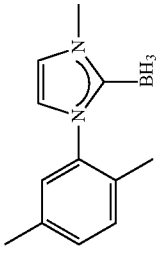 BC-1 | 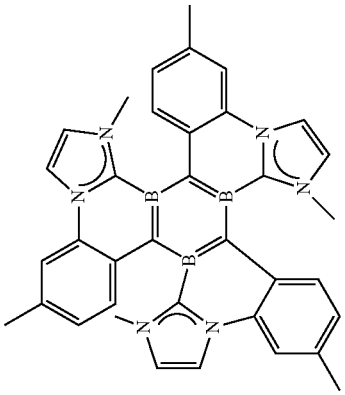 BC-1b | |
| | 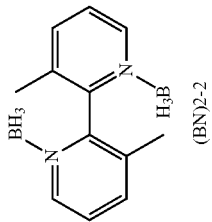 (BN)2-2 | 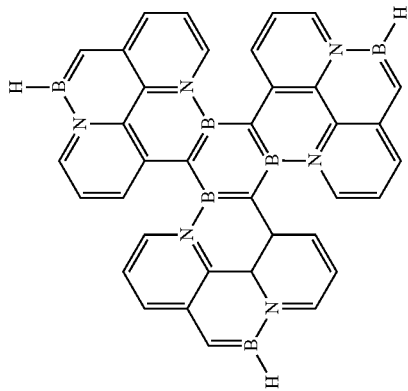 (BN)2-2a | |

TABLE 1-continued

Structural formulae of starting materials and photoelimination products.

| Ligand | Precursor | Elimination Product | Terms |
|---|---|---|---|
|  | BN-bpy-B1 | BN-bpy-B1a | R, R' = alkyl, aryl |
|  | BN-bpy-Pt1 | BN-bpy-Pt1a | R, R' = alkyl, aryl |

TABLE 2

Selective examples of fully conjugated molecules based on "trimer" compounds

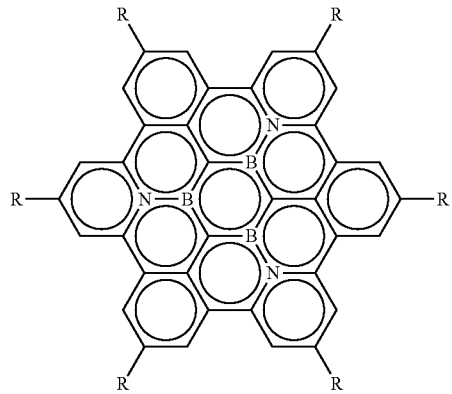

R = alkyl, OR

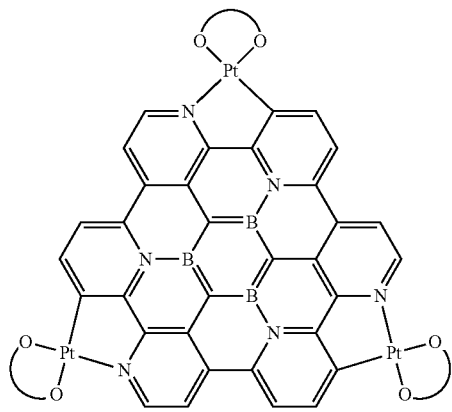

The O,O-chelate are acetylacetonate and derivative chelate ligands.

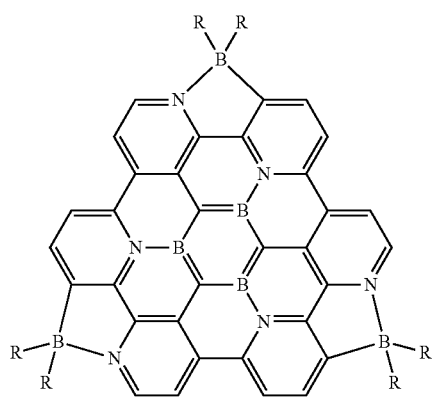

R = Aryl, Alkyl, F, OR

TABLE 2-continued

Selective examples of fully conjugated molecules based on "trimer" compounds

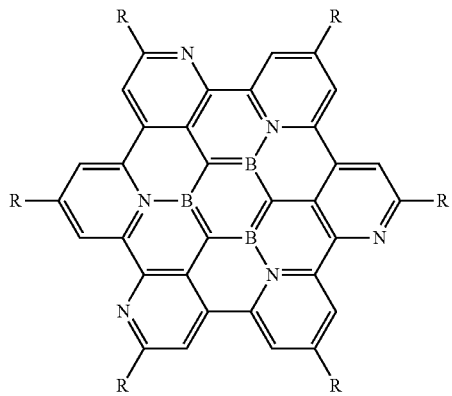

R = alkyl, OR

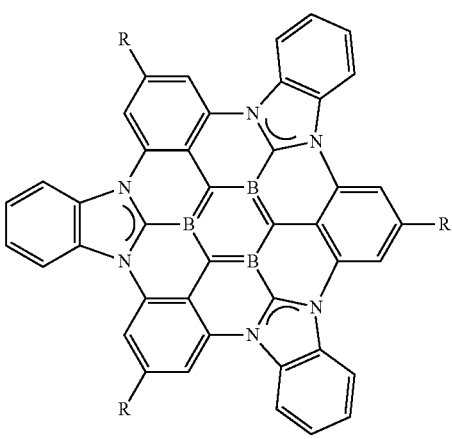

R = Alkyl, OR

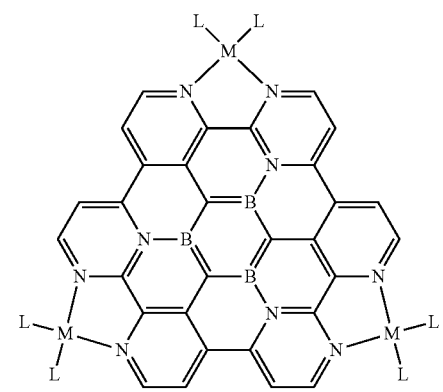

M = transition metal ion, main group elements or lanthanide metal ions
L = ligands

TABLE 2-continued

Selective examples of fully conjugated molecules based on "trimer" compounds

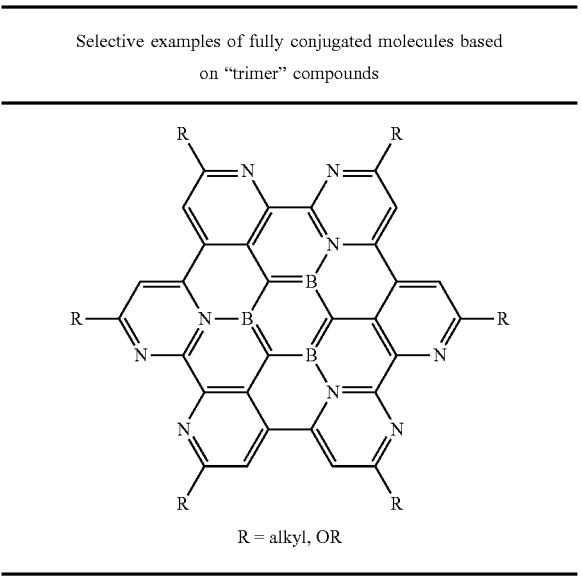

R = alkyl, OR

TABLE 3

Electronic and photophysical properties of selected azaborines

| | UV/Vis (nm)[a] | Fluorescence (nm)[a] | $\Phi_{FL}$[b] | UV/Vis in PMMA[c] (nm) | Fluorescence in PMMA[c] (nm) | $E_{1/2}^{red}$ (V)[d] |
|---|---|---|---|---|---|---|
| BN-1a | 422, 447, 470 | 493 513 | 0.27 | 447, 470 | 505 | −2.49 |
| BN-2a | 428, 455, 478 | 500 | ~1.00 | 452, 476 | 510 | −2.48 |
| BN-3a | 430, 455, 481 | 524 | 0.16 | 455, 483 | 514 | −2.44 |
| BN-4a | 425, 449, 474 | 509 | ~1.00 | 454, 479 | 507 | n/a[g] |

[a]$1.0 \times 10^{-5}$ in toluene.
[b]Determined using Ir(ppy)$_3$ as the standard ($\Phi$ = 0.92) in toluene.
[c]10 wt % PMMA films.
[d]Relative to the potential of FeCp$_2^{0/+}$, recorded in a CH$_3$CN-THF solvent mixture.

We claim:

1. A method of making aromatic azaborine compounds, comprising:
   photoirradiating a reactant; and
   obtaining an elimination product;
   wherein the reactant comprises:
   (i) a boron atom that is bonded at least to a first moiety and a second moiety, the first moiety being a terminal moiety, and the second moiety being a Lewis base comprising an aryl, heteroaryl, N-heterocyclic carbene, or a heteroatom;
   (ii) a carbon atom that is proximal to the boron and that is bonded to at least one hydrogen atom;
   wherein the elimination product differs from the reactant such that the elimination product:
   (a) has a bond between the boron and the carbon, which may be a single bond or an additional bond between the boron and the carbon; and
   (b) does not include the first moiety.

2. The method of claim 1, comprising a reaction:

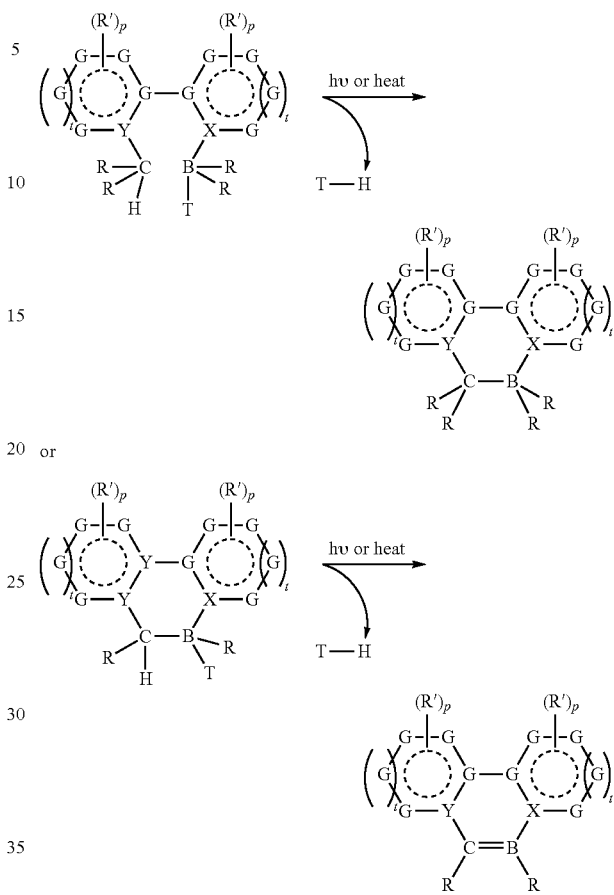

wherein G is independently carbon or a heteroatom;
X and Y are independently carbon or nitrogen;
T is a terminal moiety;
R is hydrogen, a linear, branched or cyclic aliphatic moiety, or an aryl (which includes heteroaryl) moiety, and may be further substituted;
R' is hydrogen, a linear, branched or cyclic aliphatic moiety, or an aryl (which includes heteroaryl) moiety, and may be further substituted, and is optionally a fused ring(s);
t is independently 0 or 1;
p is independently 0 to 10; and
a dotted circle represents optional aromaticity;
with the proviso that at least one moiety bonded to B, excluding the terminal moiety, is a Lewis base,
wherein each ring has 0-2 ring atoms that are heteroatoms, and at least one ring of the product is an aryl ring.

3. The method of claim 1, wherein the elimination product is photoluminescent or electroluminescent.

4. The method of claim 1, wherein the elimination product is an electron transport material.

5. The method of claim 2, wherein the reactant is: BN-1, BN-2, BN-3, BN-4, BN-7, (BN2)-1, (BN2)-2, BC-1, BC-2, BC-3, BC-4, BN-bpy1, SM1, DT1, or BN-Bpy-Pt1

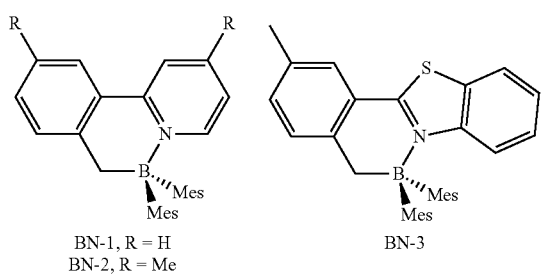
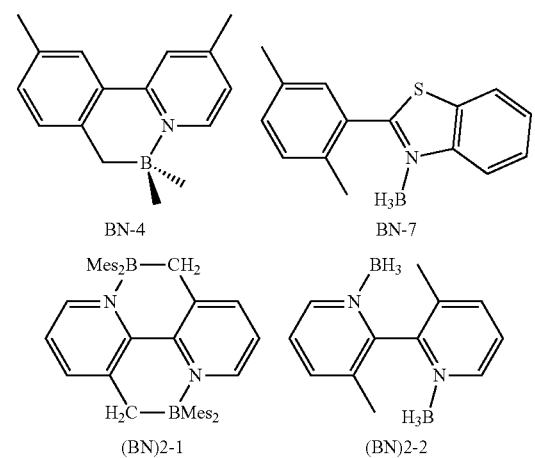
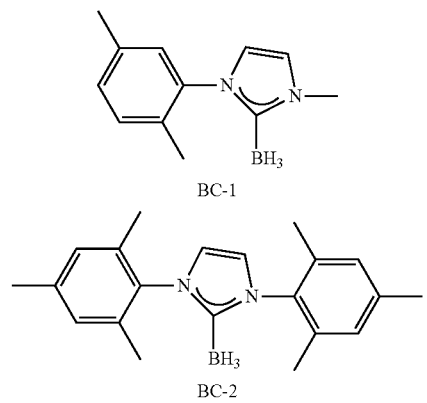
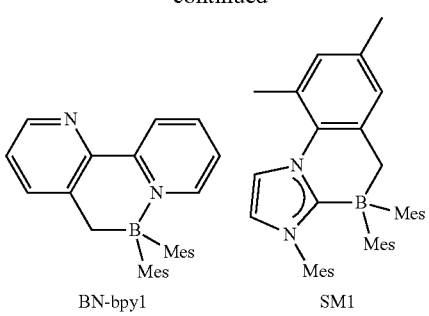
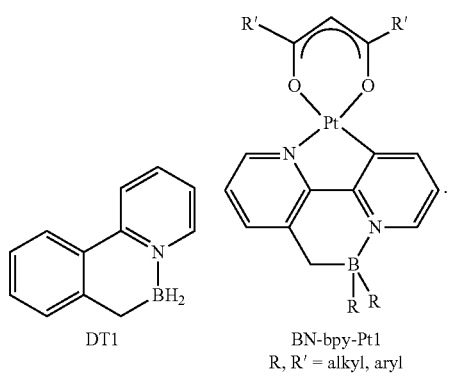
6. The method of claim 1, wherein the elimination product is: BN-1a, BN-2a, BN-3a, BN-4a, (BN2)-1a, SM1-aza, DT1-aza, or BN-5b
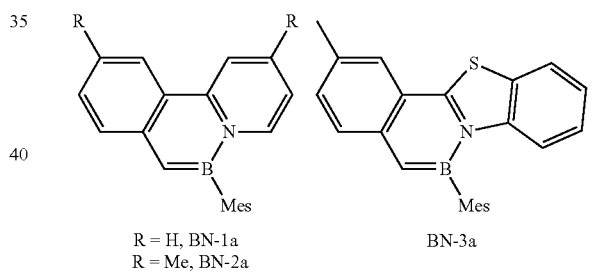
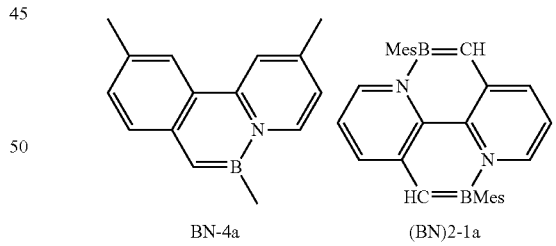
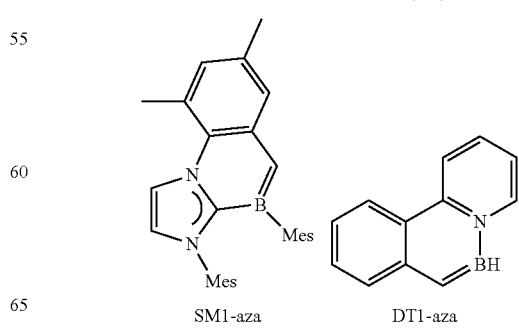

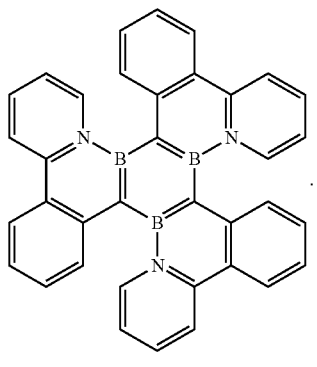
BN-5b
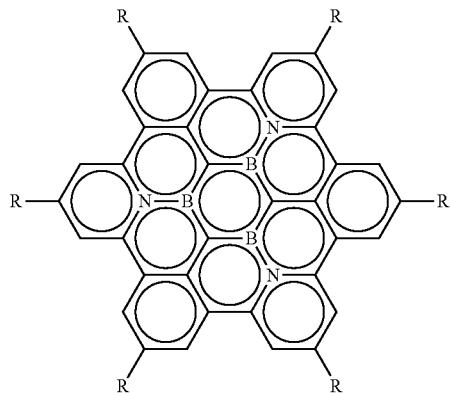
R = H, BN-5c
R = Me, BN-6c
7. The method of claim 1, wherein a final product is a triboron compound or a conjugated polycyclic compound comprising B—N moieties.
8. The method of claim 7, wherein the triboron compound is BN-5b, (BN)2-2a, BN-5c, BN-6c, BC-1b, BN-7b, BN-bpyB1a, BN-bpy-Pt1a, or BC-1
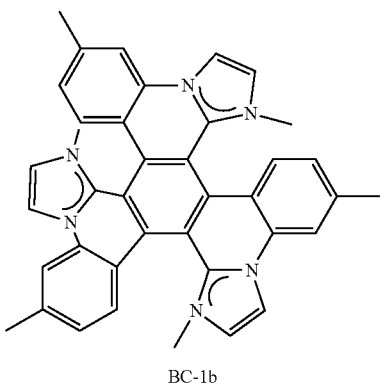
BC-1b
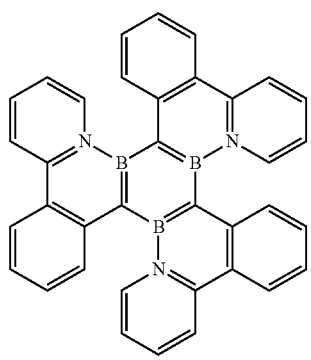
BN-5b
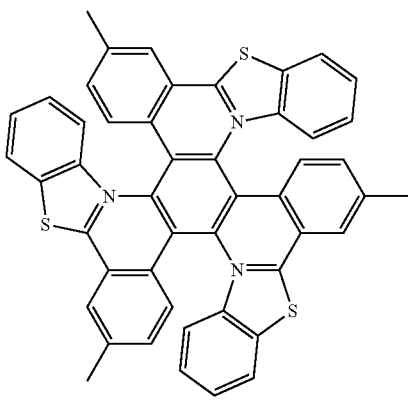
BN-7b
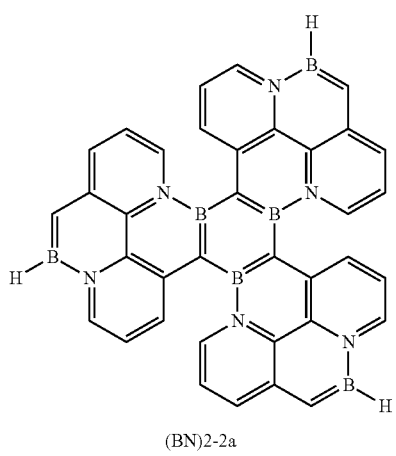
(BN)2-2a
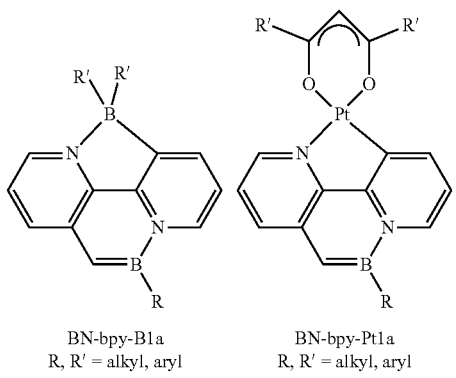
BN-bpy-B1a
R, R' = alkyl, aryl
BN-bpy-Pt1a
R, R' = alkyl, aryl -continued

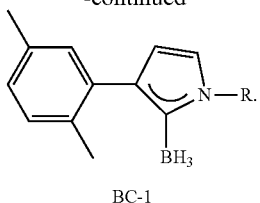

BC-1

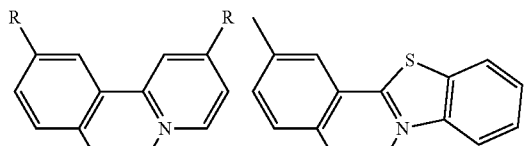

R = H, BN-1a
R = Me, BN-2a

BN-3a

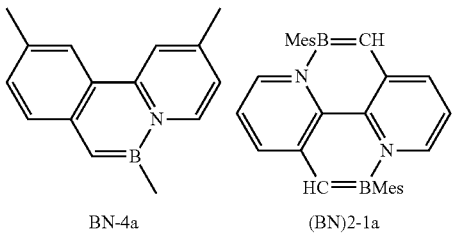

BN-4a (BN)2-1a

9. An electroluminescent device for use with an applied voltage, comprising:
a first electrode,
an emitter which is an electroluminescent elimination product of claim 1, optionally in a host layer, and
a second, transparent electrode,
wherein voltage is applied to the two electrodes to produce an electric field across the emitter so that the emitter electroluminesces.

10. A compound of general formula:

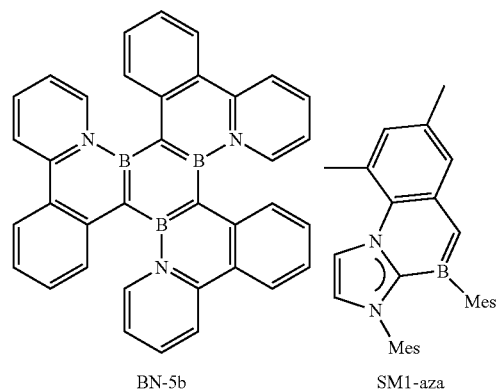

BN-5b

SM1-aza wherein G is independently carbon or a heteroatom (e.g., N, S, O, P);
X and Y are independently carbon or nitrogen;
R is an aliphatic or aryl (which includes heteroaryl) moiety that may be further substituted;
R' is an aliphatic or aryl (which includes heteroaryl) moiety that may be further substituted and is optionally a fused ring(s);
t is independently 0 or 1;
p is independently 0 to 10; and
a dotted circle represents optional aromaticity;
wherein each ring has 0-2 ring atoms that are heteroatoms, and at least one ring of the product is an aryl ring.

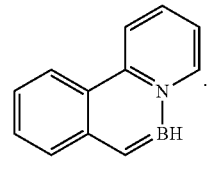

DT1-aza

16. A compound which comprises a structure of general formula:

11. The compound of claim 10, wherein for the ring comprising X, t is zero and at least one ring atom is a heteroatom, so that ring is a five-membered heterocycle.

12. The compound of claim 10, wherein X is nitrogen and Y is carbon.

13. The compound of claim 10, wherein the ring comprising Y is substituted phenyl.

14. The compound claim 10, wherein the R substituent on B is mesityl.

15. The compound of claim 10, wherein the compound is BN-1a, BN-2a, BN-3a, BN-4a, (BN2)-1a, BN-5b, SM1-aza, or DT1-aza

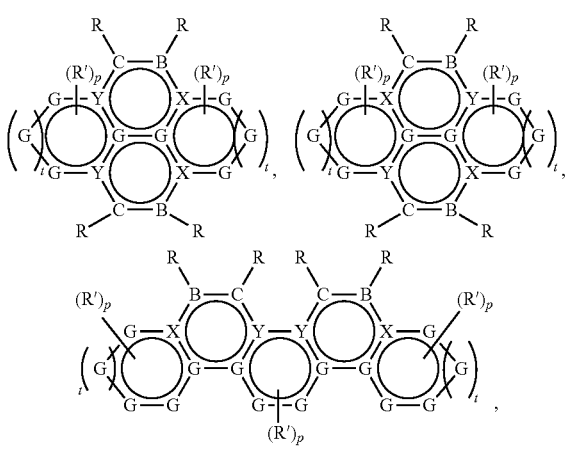

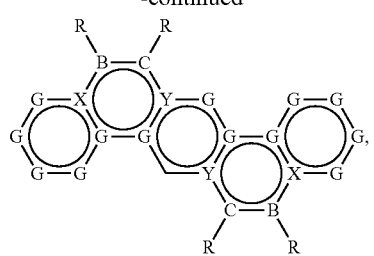

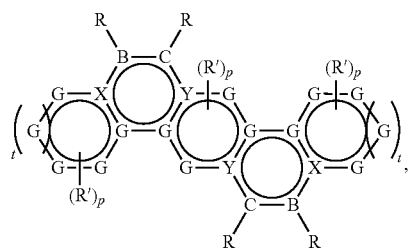

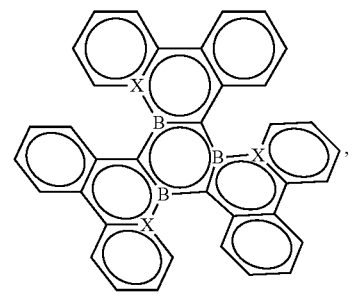

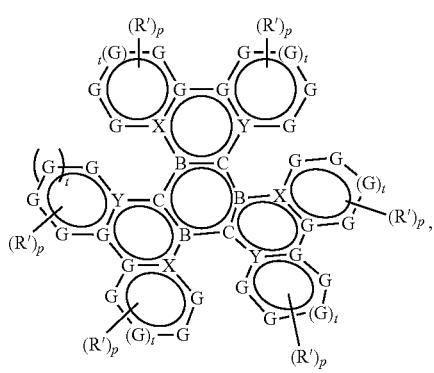

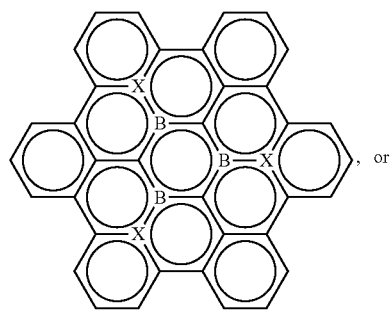, or

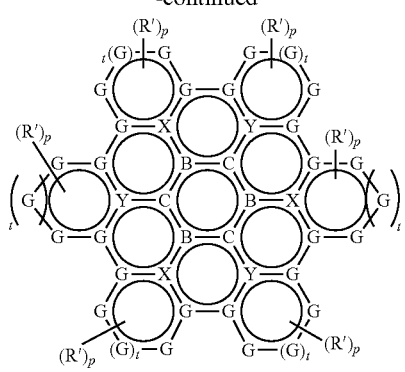

wherein G is independently carbon or a heteroatom (e.g., N, S, O, P;

X and Y are independently carbon or nitrogen;

T is a terminal moiety;

R is hydrogen, a linear, branched or cyclic aliphatic moiety, or an aryl (which includes heteroaryl) moiety, and may be further substituted;

R' is hydrogen, a linear, branched or cyclic aliphatic moiety, or an aryl (which includes heteroaryl) moiety, and may be further substituted, and is optionally a fused ring(s);

t is independently 0 or 1;

p is independently 0 to 10; and a dotted circle represents optional aromaticity;

wherein each ring has 0-2 ring atoms that are heteroatoms, and at least one ring of the product is an aryl ring, and with the proviso that at least one moiety bonded to B, excluding the terminal moiety, is a Lewis base, and wherein rings may be substituted or unsubstituted.

17. The compound of claim 16, wherein the compound is (BN)2-2, BN-5b, (BN)2-2a, BN-5c, BN-6c, BC-1b, BN-7b, BN-bpyB1a, BN-bpy-Pt1a, BC-1, BN-5, BN-6, BN-1a, BN-2a, BN-3a, BN-4a, (BN2)-1a, BN-5b, SM1-aza, or DT1-aza

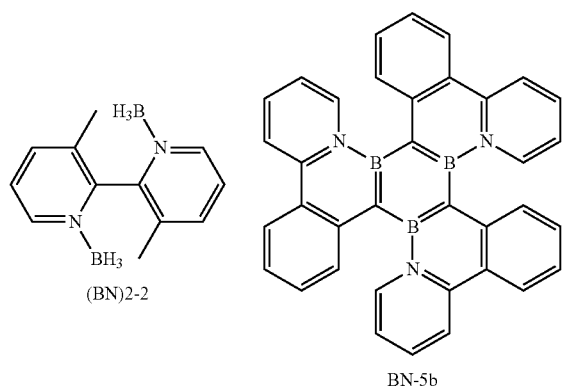

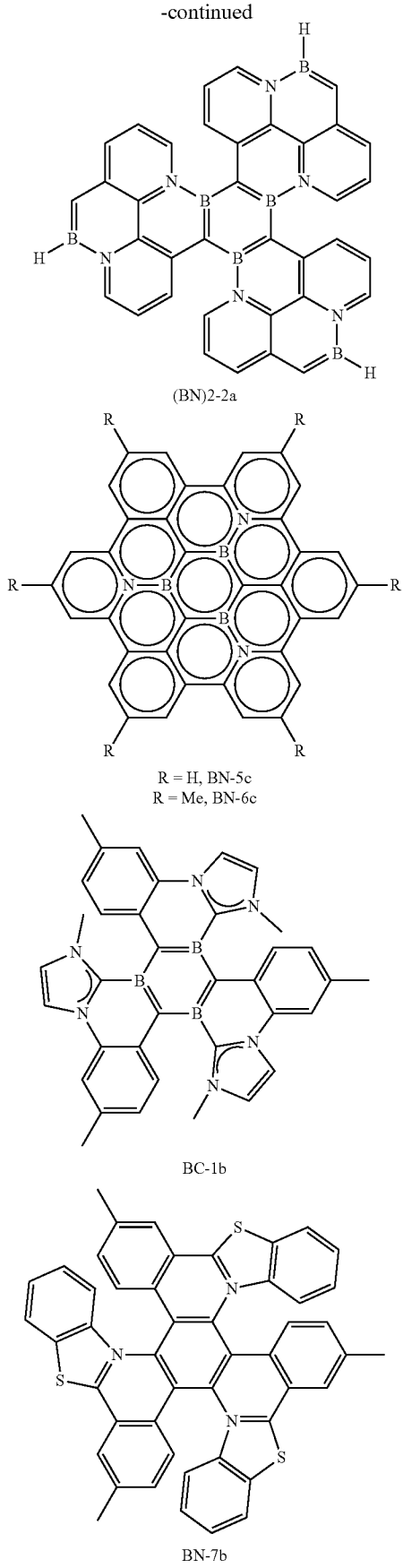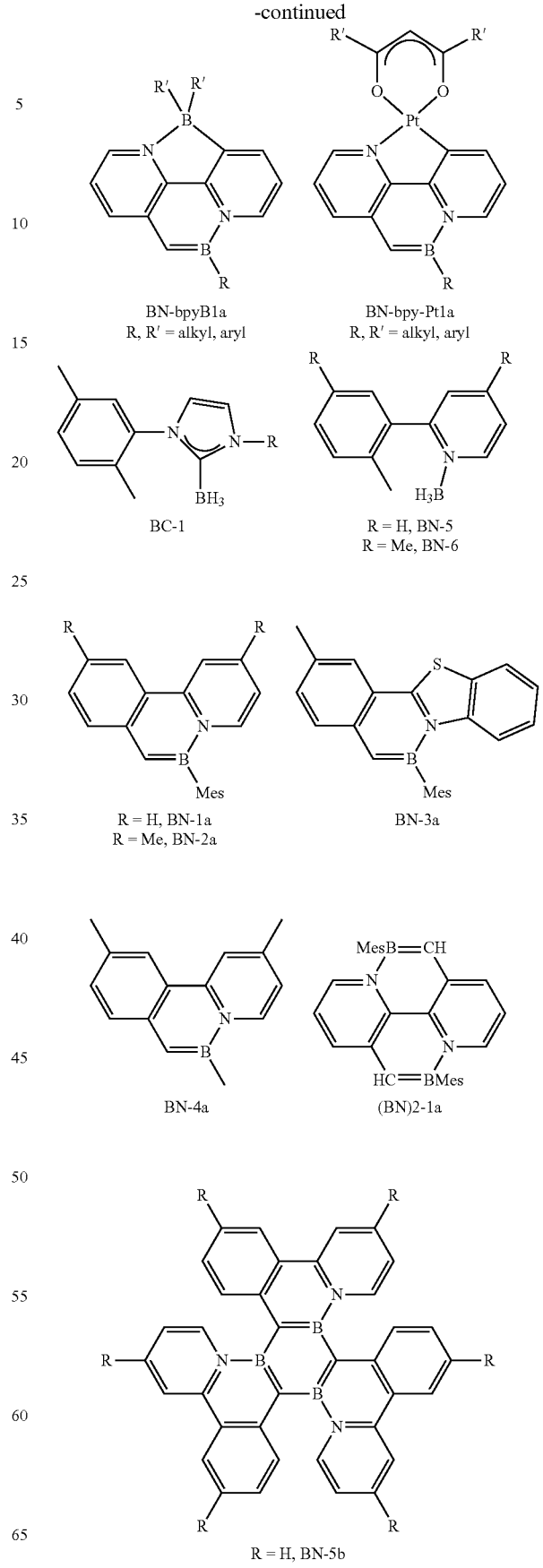

-continued
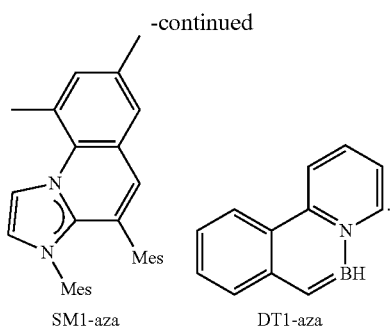
18. The method of claim 1, wherein the elimination product's boron atom can undergo one or more subsequent elimination reaction(s) involving the same carbon atom or a different carbon atom.
* * * * *